US011744250B2

(12) United States Patent
Bowen et al.

(10) Patent No.: US 11,744,250 B2
(45) Date of Patent: Sep. 5, 2023

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Arlene R. Howe, Clarkson Valley, MO (US); Jason S. Milligan, Troy, IL (US); Christina M. Taylor, St. Louis, MO (US); Monika R. VanGordon, St. Louis, MO (US); Kimberly M. Wegener, St. Louis, MO (US); Brian E. Weiner, Chapel Hill, NC (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

(21) Appl. No.: 17/559,857

(22) Filed: Dec. 22, 2021

(65) Prior Publication Data

US 2022/0192200 A1 Jun. 23, 2022

Related U.S. Application Data

(60) Provisional application No. 63/130,385, filed on Dec. 23, 2020.

(51) Int. Cl.

| | |
|---|---|
| ***A01N 63/50*** | (2020.01) |
| ***A01P 7/04*** | (2006.01) |
| ***C07K 14/32*** | (2006.01) |
| ***C12N 15/82*** | (2006.01) |
| ***C12Q 1/6895*** | (2018.01) |
| ***G01N 33/68*** | (2006.01) |

(52) U.S. Cl.

CPC ................ *A01N 63/50* (2020.01); *A01P 7/04* (2021.08); *C07K 14/32* (2013.01); *C12N 15/8286* (2013.01); *C12Q 1/6895* (2013.01); *G01N 33/68* (2013.01); *C12Q 2600/13* (2013.01)

(58) Field of Classification Search

None

See application file for complete search history.

(56) References Cited

U.S. PATENT DOCUMENTS

| | | | |
|---|---|---|---|
| 5,188,642 | A | 2/1993 | Shah et al. |
| 5,312,910 | A | 5/1994 | Kishore et al. |
| 5,500,365 | A | 3/1996 | Fischhoff et al. |
| 5,627,061 | A | 5/1997 | Barry et al. |
| 5,633,435 | A | 5/1997 | Barry et al. |
| 5,728,925 | A | 3/1998 | Herrera-Estrella et al. |
| 5,750,871 | A | 5/1998 | Moloney et al. |
| 5,880,275 | A | 3/1999 | Fischhoff et al. |
| 6,033,874 | A | 3/2000 | Baum et al. |
| 6,365,807 | B1 | 4/2002 | Christou et al. |
| 6,501,009 | B1 | 12/2002 | Romano |
| 6,551,962 | B1 | 4/2003 | Pershing et al. |
| 6,713,063 | B1 | 3/2004 | Malvar et al. |
| 6,752,992 | B2 * | 6/2004 | Schnepf et al. ..... C07K 14/325 424/246.1 |
| 6,780,408 | B1 | 8/2004 | Bosch et al. |
| 6,962,705 | B2 | 11/2005 | Malvar et al. |
| 7,026,528 | B2 | 4/2006 | Cheng et al. |
| 7,064,249 | B2 | 6/2006 | Corbin et al. |
| 7,070,982 | B2 | 7/2006 | Malvar et al. |
| 7,193,133 | B2 | 3/2007 | Lassner et al. |
| 7,510,878 | B2 | 3/2009 | Abad et al. |
| 7,772,465 | B2 | 8/2010 | Abad et al. |
| 7,812,129 | B1 | 10/2010 | Abad et al. |
| 8,344,207 | B2 | 1/2013 | Bogdanova et al. |
| 8,609,936 | B2 | 12/2013 | Baum et al. |
| 10,059,959 | B2 | 8/2018 | Baum et al. |

(Continued)

FOREIGN PATENT DOCUMENTS

| | | |
|---|---|---|
| EP | 0218571 | 2/1993 |
| EP | 0189707 | 8/1993 |

(Continued)

OTHER PUBLICATIONS

Szczesna-Skorupa et al. "Mutations int he NH2-terminal Domain of the Signal Peptide of Preproparathyroid Hormone Inhibit Translocation without Affecting Interaction with SignalR ecognition Particle" 1987 (J. Biol. Chem. 262(18):8896-8900) (Year: 1987).*

Lammertyn and Anne "Modi¢cations of Streptomyces signal peptides and their ejects on protein production and secretion" 1998 (FEMS Micro. Letters 160(1):1-10) (Year: 1998).*

Betts and Russell 2003 (Chapter 14: Amino Acid Properties and Consequences of Substitutions in Bioinformatics for Geneticists Eds. Barns and Gray; 28 total pages) (Year: 2003).*

Alphey, et al. Combining Pest Control and Resistance Management: Synergy of Engineered Insects With Bt Crops, Journal of Economic Entomology, vol. 102, Issue 2, pp. 717-732, 2009.

Arencibia, et al. An efficient protocol for sugarcane (*Saccharum spp.* L.) transformation mediated by Agrobacterium tumefaciens. Transgenic Res 7, 213-222 (1998).

(Continued)

*Primary Examiner* — Matthew R Keogh
*Assistant Examiner* — Rebecca Stephens
(74) *Attorney, Agent, or Firm* — Dentons US LLP; Timothy K. Ball

(57) ABSTRACT

Pesticidal proteins exhibiting inhibitory, suppressive, and toxic activity against Lepidopteran pest species are disclosed, and include, but are not limited to, TIC4064 and TIC4064 amino acid sequence variants. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Lepidopteran species pests using any of the TIC4064 and TIC4064 amino acid sequence variant pesticidal proteins are also provided.

18 Claims, No Drawings

Specification includes a Sequence Listing.

(56) References Cited

U.S. PATENT DOCUMENTS

| | | | |
|---|---|---|---|
| 10,155,960 | B2 | 12/2018 | Bowen et al. |
| 10,227,608 | B2 | 3/2019 | Barry et al. |
| 10,233,217 | B2 | 3/2019 | Baum et al. |
| 10,494,408 | B2 | 12/2019 | Baum et al. |
| 10,611,806 | B2 | 4/2020 | Baum et al. |
| 10,669,317 | B2 | 6/2020 | Baum et al. |
| 10,703,782 | B2 | 7/2020 | Baum et al. |
| 2001/0042257 | A1 | 11/2001 | Connor-Ward et al. |
| 2003/0105319 | A1 | 6/2003 | Schnepf et al. |
| 2003/0110531 | A1 | 6/2003 | Dan et al. |
| 2006/0021087 | A1 | 1/2006 | Baum et al. |
| 2006/0112447 | A1 | 5/2006 | Bogdanova et al. |
| 2006/0241043 | A1 | 10/2006 | Flannagan et al. |
| 2008/0172762 | A1 | 7/2008 | Cerf et al. |
| 2008/0256667 | A1 | 10/2008 | Dersch et al. |
| 2008/0280361 | A1 | 11/2008 | Calabotta et al. |
| 2008/0282432 | A1 | 11/2008 | Duncan et al. |
| 2009/0138985 | A1 | 5/2009 | Martinell et al. |
| 2009/0142837 | A1 | 6/2009 | Adams et al. |
| 2009/0313721 | A1 | 12/2009 | Abad et al. |
| 2010/0004176 | A1 | 1/2010 | Sampson et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0137216 | A1 | 6/2010 | Carozzi et al. |
| 2010/0160231 | A1 | 6/2010 | Sampson et al. |
| 2010/0192256 | A1 | 7/2010 | Abad et al. |
| 2010/0197592 | A1 | 8/2010 | Heinrichs |
| 2010/0269221 | A1 | 10/2010 | Abad et al. |
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0030096 | A1 | 2/2011 | Sampson et al. |
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0210462 | A1 | 8/2012 | Bermudez et al. |
| 2012/0233726 | A1 | 9/2012 | Abad et al. |
| 2013/0055469 | A1 | 2/2013 | Sampson et al. |
| 2013/0097735 | A1 | 4/2013 | Bowen et al. |
| 2013/0104259 | A1 | 4/2013 | Sampson et al. |
| 2013/0117884 | A1 | 5/2013 | Hargiss et al. |
| 2013/0167264 | A1 | 6/2013 | Sampson et al. |
| 2013/0219570 | A1 | 8/2013 | Lira et al. |
| 2013/0269060 | A1 | 10/2013 | Baum et al. |
| 2013/0303440 | A1 | 11/2013 | Sampson et al. |
| 2013/0310543 | A1 | 11/2013 | Sampson et al. |
| 2014/0007292 | A1 | 1/2014 | Cerf et al. |
| 2014/0033361 | A1 | 1/2014 | Altier et al. |
| 2014/0033363 | A1 | 1/2014 | Sampson |
| 2014/0196175 | A1 | 7/2014 | Sampson et al. |
| 2014/0223598 | A1 | 8/2014 | Sampson et al. |
| 2014/0223599 | A1 | 8/2014 | Sampson et al. |
| 2014/0245491 | A1 | 8/2014 | Sampson et al. |
| 2014/0298538 | A1 | 10/2014 | Heinrichs et al. |
| 2014/0366227 | A1 | 12/2014 | Gatehouse et al. |
| 2014/0373195 | A1 | 12/2014 | Sampson et al. |
| 2016/0366891 | A1 | 12/2016 | Diehn et al. |
| 2017/0174731 | A1 | 6/2017 | Kennedy et al. |
| 2020/0095603 | A1 | 3/2020 | Bowen et al. |
| 2020/0229445 | A1 | 7/2020 | Bowen et al. |

FOREIGN PATENT DOCUMENTS

| | | | |
|---|---|---|---|
| EP | 0508909 | | 8/1998 |
| EP | 0924299 | | 5/2004 |
| WO | 2013134523 | | 9/2013 |
| WO | 2014008054 | A2 | 1/2014 |
| WO | 2015195594 | A2 | 12/2015 |
| WO | 2016061391 | A2 | 4/2016 |
| WO | 2016061392 | | 4/2016 |
| WO | 2019178038 | | 9/2019 |
| WO | 2020055647 | A1 | 3/2020 |

OTHER PUBLICATIONS

Della-Cioppa, et al. Translocation of the precursor of 5-enolpyruvylshikimate-3-phosphate synthase into chloroplasts of higher plants in vitro. PNAS, vol. 83, No. 18 (1986).

Gleave, et al. Identification of an insecticidal crystal protein from Bacillus thuringiensis DSIR517 with significant sequence differences from previously described toxins. Journal of General Microbiology, vol. 138, Issue 1, pp. 55-62 (1992).

ISAAA, 2016. Global Status of Commercialized Biotech/ GM Crops: 2016. ISAAA Brief No. 52 ISAAA: Ithaca, NY.

Jin, et al. Engineered Female-Specific Lethality for Control of Pest Lepidoptera. ACS Synth. Biol. 2013, 2, 3, 160-166 (2013).

Klee, et al. Cloning of an *Arabidopsis thaliana* gene encoding 5-enolpyruvylshikimate-3-phosphate synthase: sequence analysis and manipulation to obtain glyphosate-tolerant plants. Mol Gen Genet 210, 437-442 (1987).

Thompson, et al. CLUSTAL W: improving the sensitivity of progressive multiple sequence alignment through sequence weighting, position-specific gap penalties and weight matrix choice. Nucleic Acids Research, vol. 22, Issue 22, pp. 4673-4680, (1994).

Zhou, et al. Combining the high-dose/refuge strategy and self-limiting transgenic insects in resistance management—A test in experimental mesocosms. Evolutionary Applications, vol. 11, Issue 5, pp. 727-738, (2018).

GenBank Accession No. CAA41425, dated Jul. 26, 2016.

GenBank Accession No. WP_087976765, dated Oct. 18, 2021.

International Search Report and Written Opinion regarding International App. No. PCT/US2021/064936, dated Sep. 27, 2022.

* cited by examiner

INSECT INHIBITORY PROTEINS

REFERENCE TO RELATED APPLICATION

This application claims the benefit of U.S. provisional application No. 63/130,385, filed Dec. 23, 2020, which is herein incorporated by reference in its entirety.

INCORPORATION OF SEQUENCE LISTING

The file named "BCS206472_US_01_SEQLISTING_ST25.txt" contains a computer-readable form of the Sequence Listing and was created on Dec. 22, 2021. The file is 346,131 bytes (measured in MS-Windows®), is filed contemporaneously along with this application by electronic submission (using the United States Patent Office EFS-Web filing system), and is incorporated herein by reference in its entirety.

FIELD OF THE INVENTION

The invention generally relates to the field of insect inhibitory proteins. A novel class of proteins are disclosed exhibiting insect inhibitory activity against agriculturally relevant pests of crop plants and seeds, particularly Lepidopteran species of insect plant pests. Provided are plants, plant parts, seed, cells including plant as well as bacterial cells, and vectors, each respectively containing a recombinant polynucleotide construct comprising in operable linkage a heterologous promoter and a polynucleotide segment encoding one or more of the disclosed toxin proteins.

BACKGROUND OF THE INVENTION

Improving crop yield from agriculturally significant plants including, among others, corn, soybean, sugarcane, rice, wheat, canola, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields over infested areas. Lepidopteran pest species which negatively impact agriculture include, but are not limited to, Black armyworm (*Spodoptera cosmioides*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Sugarcane borer (*Diatraea saccharalis*), Sunflower looper (*Rachiplusia nu*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*), *Paenibacillus popilliae* and *Paenibacillus lentimorbus*. In addition, insecticidal toxins have also been identified from a variety of non-bacterial sources including ferns, arachnid venoms, and delivery in a diet of a pest of dsRNA targeting an essential gene for suppression has been identified as an effective pest management strategy.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein(s).

The use of transgenic plants expressing insecticidal toxin proteins has been globally adapted. For example, in 2016, 23.1 million hectares were planted with transgenic crops expressing Bt toxins and 75.4 million hectares were planted with transgenic crops expressing Bt toxins stacked with herbicide tolerance traits (ISAAA. 2016. Global Status of Commercialized Biotech/GM Crops: 2016. ISAAA Brief No. 52. ISAAA: Ithaca, N.Y.). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action or alternatively two or more different modes of toxic action (for example, a transgene encoding a dsRNA targeting an essential gene for suppression coupled with a transgene that encodes a peptide or protein toxin, both toxic to the same insect species) reduces the probability of resistance in any single target insect species. Additionally, use of self-limiting technologies such as those provided by Oxitec Ltd, when used together with the proteins of the present invention, should improve durability of the traits imparted to transgenic crops expressing proteins of the present invention (Zhou et al. 2018, *Evol Appl* 11(5):727-738; Alphey et al., 2009, *Journal of Economic Enontogy,* 102: 717-732).

Thus, the inventors disclose herein a novel protein from *Bacillus thuringiensis*, along with engineered variant proteins, and exemplary recombinant proteins, that each exhibit insecticidal activity against target Lepidopteran species, particularly against Black armyworm (*Spodoptera cosmioides*), Black cutworm (*Agrotis ipsilon*), Corn earworm (*Helicoverpa zea*), European corn borer (*Ostrinia nubilalis*), South American pod worm (*Helicoverpa gelotopoeon*), Southern armyworm (*Spodoptera eridania*), Soybean looper (*Chrysodeixis includens*), Southwestern corn borer (*Diatraea grandiosella*), Tobacco budworm (*Heliothis virescens*), and Velvet bean caterpillar (*Anticarsia gemmatalis*).

SUMMARY OF THE INVENTION

Disclosed herein is a novel pesticidal protein, TIC4064, and engineered variants thereof with insect inhibitory activity which are shown to exhibit inhibitory activity against one or more pests of crop plants. The TIC4064 protein and variant proteins in the TIC4064 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or pesticidal fragment thereof, wherein the pesticidal protein comprises the amino acid sequence of SEQ ID NO:8, SEQ ID NO:10, SEQ ID NO:2, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, or SEQ ID NO:52; or the pesticidal protein comprises an amino acid sequence having at least 98% or 99%, or 99.5%, or about 100% identity to the amino acid sequence as set forth in SEQ ID NO:8, SEQ ID NO:10, SEQ ID NO:2, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, or SEQ ID NO:52; or the polynucleotide segment hybridizes under stringent hybridization conditions to a polynucleotide having the nucleotide sequence as set forth in SEQ ID NO:7, SEQ ID NO:9, SEQ ID NO:1, SEQ ID NO:3, SEQ ID NO:5, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51. The recombinant nucleic acid molecule can comprise a sequence that functions to express the pesticidal protein in a plant, and which when expressed in a plant cell, produces a pesticidally effective amount of the pesticidal protein or a pesticidal fragment thereof.

In another embodiment of this application the recombinant nucleic acid molecule is present within a bacterial or plant host cell. Contemplated bacterial host cells include at least the genus of *Agrobacterium, Rhizobium, Bacillus, Brevibacillus, Escherichia, Pseudomonas, Klebsiella, Pantoea*, and *Erwinia*. In certain embodiments, the *Bacillus* species is a *Bacillus cereus* or *Bacillus thuringiensis*, the *Brevibacillus* is a *Brevibacillus laterosporus*, or the *Escherichia* is a *Escherichia coli*. Contemplated plant host cells include a dicotyledonous plant cell and a monocotyledonous plant cell. Contemplated plant cells further include an alfalfa, banana, barley, bean, broccoli, cabbage, brassica (e.g. canola), carrot, cassava, castor, cauliflower, celery, chickpea, Chinese cabbage, citrus, coconut, coffee, corn (i.e. maize, such as sweet corn, or field corn), clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cell.

In another embodiment, the pesticidal protein exhibits activity against Lepidopteran insects, including at least, Black armyworm (*Spodoptera cosmioides*), Black cutworm (*Agrotis ipsilon*), Corn earworm (*Helicoverpa zea*), European corn borer (*Ostrinia nubilalis*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sunflower looper (*Rachiplusia nu*), Tobacco budworm (*Heliothis virescens*), and Velvet bean caterpillar (*Anticarsia gemmatalis*).

Also contemplated in this application are plants or plant parts comprising a recombinant nucleic acid molecule encoding a pesticidal protein or fragment thereof of the TIC4064 protein toxin class. Both dicotyledonous plants and monocotyledonous plants are contemplated. In another embodiment, the plant is further selected from the group consisting of an alfalfa, banana, barley, bean, broccoli, cabbage, brassica (e.g. canola), carrot, cassava, castor, cauliflower, celery, chickpea, Chinese cabbage, citrus, coconut, coffee, corn (i.e. maize, such as sweet corn or field corn), clover, cotton (e.g. *G. hirsutum, G. barbadense*), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat.

In certain embodiments, seed comprising the recombinant nucleic acid molecules are disclosed.

In still another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is, in one embodiment, selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC4029, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657, DIG-11 protein, IDP102Aa and homologs thereof, IDP110Aa and homologs thereof, TIC868, Cry1Da1_7, BCW003, TIC1100, TIC867, TIC867_23, TIC4029, TIC6757. TIC7941, IDP072Aa, TIC5290, TIC3668, TIC3669, TIC3670, IDP103 and homologs thereof, PIP-50 and PIP-65 and homologs thereof, PIP-83 and homologs thereof, and Cry1B.34.

Commodity products comprising a detectable amount of the recombinant nucleic acid molecules and toxin proteins disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising the recombinant nucleic acid molecules and toxin proteins from the TIC4064 protein toxin class. The method comprises planting at least one seed comprising the recombinant nucleic acid molecules disclosed in this application; growing a plant from the seed; and harvesting seed from the plant, wherein the harvested seed comprises the referenced recombinant nucleic acid molecules.

In another illustrative embodiment, a plant resistant to Lepidopteran insect infestation is provided wherein the cells of said plant comprise the recombinant nucleic acid molecule disclosed herein.

Also disclosed in this application are methods for controlling a Lepidopteran species pest and controlling a Lepidopteran species pest infestation of a plant, particularly a crop plant. The method comprises, in one embodiment, first contacting the pest with an insecticidally effective amount of a pesticidal protein as set forth in SEQ ID NO:8, SEQ ID NO:10, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32; or contacting the pest with an insecticidally effective amount of one or more pesticidal proteins comprising an amino acid sequence having at least 98%, or 99%, or 99.5%, or about 100% identity to the amino acid sequence as set forth in SEQ ID NO:8, SEQ ID NO:10, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32.

Further provided herein is a method of detecting the presence of a recombinant nucleic acid molecule of the TIC4064 class wherein the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:7, SEQ ID NO:9, SEQ ID NO:3, SEQ ID NO:5, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31, or a sequence that encodes a pesticidal protein comprising an amino acid sequence having at least 98%, or 99%, or 99.5%, or about 100% identity to the amino acid sequence as set forth in SEQ ID NO:7, SEQ ID NO:9, SEQ ID NO:3, SEQ ID NO:5, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; subjecting the sample and probe to stringent hybridization conditions; and detecting hybridization of the probe with DNA of the sample. In some embodiments a step of detecting the presence of a member of the TIC4064 toxin protein class may comprise an ELISA or a western blot.

Also provided herein are methods of detecting the presence of pesticidal protein or fragments thereof from the TIC4064 class wherein the method comprises contacting a sample suspected of containing a TIC4064 class toxin protein with an antibody that is specifically immunoreactive with a TIC4064 class protein toxin; and detecting the binding of the antibody to the TIC4064 class protein, thus confirming the presence of the protein. In some embodiments the step of detecting comprises an ELISA, or a western blot. Producing antibodies is well within the skill of the ordinary artisan in the field of plant molecular biology.

Also contemplated in this application is a method for controlling a Lepidopteran pest species or pest infestation in a field wherein the method comprises growing a crop plant which expresses an insecticidally effective amount of a pesticidal protein having the amino acid sequence as set forth in SEQ ID NO:8, SEQ ID NO:10, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32; or growing a crop plant which expresses an insecticidally effective amount of one or more pesticidal proteins comprising an amino acid sequence having at least 98%, or 99%, or 99.5%, or about 100% identity to the amino acid sequence as set forth in SEQ ID NO:7, SEQ ID NO:9, SEQ ID NO:3, SEQ ID NO:5, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; and releasing into the field with crops containing a gene encoding the toxin protein of the present invention, one or more transgenic Lepidopteran pest species each carrying a self-limiting gene, for the purpose of preventing or delaying the onset of resistance of the one or more Lepidopteran pest species to the toxin protein. In one embodiment, the crop plants can be monocotyledonous or dicotyledonous.

In another embodiment, the monocotyledonous crop plants can be corn, wheat, sorghum, rice, rye, or millet. In yet another embodiment, the dicotyledonous crop plant can be soybean, cotton, or canola.

BRIEF DESCRIPTION OF THE SEQUENCES

SEQ ID NO:1 is a nucleic acid sequence encoding a TIC4064 pesticidal protein obtained from *Bacillus thuringiensis* species EG9820.

SEQ ID NO:2 is the amino acid sequence of the TIC4064 pesticidal protein.

SEQ ID NO:3 is a synthetic coding sequence encoding a TIC4064_1 pesticidal protein designed for expression in a plant cell wherein an alanine codon is inserted as the second codon in the open reading frame, which starts at position number 1.

SEQ ID NO:4 is the amino acid sequence of TIC4064_1.

SEQ ID NO:5 is a synthetic coding sequence encoding a TIC4064_2 pesticidal protein designed for expression in a plant cell wherein an alanine codon is inserted as the second codon in the open reading frame, which starts at position number 1. TIC4064_2 is a truncation of TIC4064_1 wherein the sequence encoding the protoxin domain of TIC4064_1 has been deleted.

SEQ ID NO:6 is the amino acid sequence of TIC4064_2.

SEQ ID NO:7 is a synthetic coding sequence encoding a TIC4064_3 pesticidal protein designed for expression in a plant cell wherein an alanine codon is inserted immediately following the initiating methionine codon and a codon has been altered to introduce the amino acid change of S95T relative to TIC4064_1.

SEQ ID NO:8 is the amino acid sequence of TIC4064_3.

SEQ ID NO:9 is a synthetic coding sequence encoding a TIC4064_4 pesticidal protein designed for expression in a plant cell wherein an alanine codon is inserted as the second codon in the open reading frame, which starts at position number 1; and a codon has been altered to introduce the amino acid change of S95T relative to that position in TIC4064_1. TIC4064_4 is a truncation of TIC4064_3 wherein the coding sequence encoding the protoxin domain of TIC4064_3 has been deleted.

SEQ ID NO:10 is the amino acid sequence of TIC4064_4.

SEQ ID NO:11 is a synthetic coding sequence encoding a TIC4064_5 pesticidal protein designed for expression in a plant cell wherein an alanine codon is inserted as the second codon in the open reading frame, which starts at position number 1, and a codon has been altered to introduce the amino acid change of G88K relative to that position in TIC4064_1.

SEQ ID NO:12 is the amino acid sequence of TIC4064_5.

SEQ ID NO:13 is a synthetic coding sequence encoding a TIC4064_6 pesticidal protein designed for expression in a plant cell wherein an alanine codon is inserted as the second codon in the open reading frame, which starts at position number 1, and a codon has been altered to introduce the amino acid change of G88K relative to that position in TIC4064_1. TIC4064_6 is a truncation of TIC4064_5 wherein the coding sequence encoding the protoxin domain of TIC4064_5 has been deleted.

SEQ ID NO:14 is the amino acid sequence of TIC4064_6.

SEQ ID NO:15 is a synthetic coding sequence encoding a TIC4064_12_1 pesticidal protein designed for expression in a plant cell wherein an alanine codon is inserted as the second codon in the open reading frame, which starts at position number 1, and codons have been altered to introduce the amino acid changes of D85A, S95T, A511H, N513D, and R605N relative to those positions in TIC4064_1.

SEQ ID NO:16 is the amino acid sequence of TIC4064_12_1.

SEQ ID NO:17 is a synthetic coding sequence encoding a TIC4064_12_2 pesticidal protein designed for expression in a plant cell wherein an additional alanine codon is inserted as the second codon in the open reading frame, which starts at position number 1, and codons have been altered to introduce the amino acid changes of D85A and S95T relative to those positions in TIC4064_1.

SEQ ID NO:18 is the amino acid sequence of TIC4064_12_2.

SEQ ID NO:19 is a synthetic coding sequence encoding a TIC4064_13 pesticidal protein designed for expression in a plant cell wherein an additional alanine codon is inserted immediately following the initiating methionine codon and codons have been altered to introduce the amino acid changes of D85A, S95T, A511H, N513D, and R605N relative to TIC4064_1. TIC4064_13 is a truncation of TIC4064_12_1 wherein the coding sequence encoding the protoxin domain of TIC4064_12_1 has been deleted.

SEQ ID NO:20 is the amino acid sequence of TIC4064_13.

SEQ ID NO:21 is a synthetic coding sequence encoding a TIC4064_14 pesticidal protein designed for expression in a plant cell wherein an additional alanine codon is inserted immediately following the initiating methionine codon and codons have been altered to introduce the amino acid changes of S95T, R169K, and S332A relative to TIC4064_1.

SEQ ID NO:22 is the amino acid sequence of TIC4064_14.

SEQ ID NO:23 is a synthetic coding sequence encoding a TIC4064_15 pesticidal protein designed for expression in a plant cell wherein an alanine codon is inserted as the second codon in the open reading frame, which starts at position number 1, and codons have been altered to introduce the amino acid changes of S95T, R169K, and S332A relative to those positions in TIC4064_1. TIC4064_15 is a truncation of TIC4064_14 wherein the coding sequence encoding the protoxin domain of TIC4064_14 has been deleted.

SEQ ID NO:24 is the amino acid sequence of TIC4064_15.

SEQ ID NO:25 is a synthetic coding sequence encoding a TIC4064_16 pesticidal protein designed for expression in a plant cell wherein an alanine codon is inserted as the second codon in the open reading frame, which starts at position number 1, and codons have been altered to introduce the amino acid changes of S34G, G88K, I386S, G403Q, and R605N relative to those positions in TIC4064_1.

SEQ ID NO:26 is the amino acid sequence of TIC4064_16.

SEQ ID NO:27 is a synthetic coding sequence encoding a TIC4064_17 pesticidal protein designed for expression in a plant cell wherein an alanine codon is inserted as the second codon in the open reading frame, which starts at position number 1, and codons have been altered to introduce the amino acid changes of S34G, G88K, I386S, G403Q, and R605N relative to those positions in TIC4064_1. TIC4064_17 is a truncation of TIC4064_16 wherein the coding sequence encoding the protoxin domain of TIC4064_16 has been deleted.

SEQ ID NO:28 is the amino acid sequence of TIC4064_17.

SEQ ID NO:29 is a synthetic coding sequence encoding a TIC4064_18 pesticidal protein designed for expression in a plant cell wherein an alanine codon is inserted as the second codon in the open reading frame, which starts at position number 1, and codons have been altered to introduce the amino acid changes of G88K, W371L, H555N, and R586Q relative to those positions in TIC4064_1.

SEQ ID NO:30 is the amino acid sequence of TIC4064_18.

SEQ ID NO:31 is a synthetic coding sequence encoding a TIC4064_19 pesticidal protein designed for expression in a plant cell wherein an alanine codon is inserted as the second codon in the open reading frame, which starts at position number 1, and codons have been altered to introduce the amino acid changes of G88K, W371L, H555N, and R586Q relative to those positions in TIC4064_1. TIC4064_19 is a truncation of TIC4064_18 wherein the coding sequence encoding the protoxin domain of TIC4064_18 has been deleted.

SEQ ID NO:32 is the amino acid sequence of TIC4064_19.

SEQ ID NO:33 is a synthetic bacterial coding sequence encoding TIC4064_20 pesticidal protein wherein codons have been altered to introduce the amino acid changes of S94T, D84A, A510H, N512D, and D608A relative to those positions in TIC4064.

SEQ ID NO:34 is the amino acid sequence of TIC4064_20.

SEQ ID NO:35 is a synthetic bacterial coding sequence encoding TIC4064_21 wherein codons have been altered to introduce the amino acid changes of S94T, R168K, and S331A relative to those positions in TIC4064.

SEQ ID NO:36 is the amino acid sequence of TIC4064_21.

SEQ ID NO:37 is a synthetic bacterial coding sequence encoding TIC4064_22 wherein codons have been altered to introduce the amino acid changes of S33G and S94T relative to those positions in those positions in TIC4064.

SEQ ID NO:38 is the amino acid sequence of TIC4064_22.

SEQ ID NO:39 is a synthetic bacterial coding sequence encoding TIC4064_23 wherein codons have been altered to introduce the amino acid changes of S94T, E153D, Q436I, and S596Q relative to those positions in TIC4064.

SEQ ID NO:40 is the amino acid sequence of TIC4064_23.

SEQ ID NO:41 is a synthetic bacterial coding sequence encoding TIC4064_24 wherein codons have been altered to introduce the amino acid changes of G87K, W370L, H554N, and R585Q relative to those positions in TIC4064.

SEQ ID NO:42 is the amino acid sequence of TIC4064_24.

SEQ ID NO:43 is a synthetic bacterial coding sequence encoding TIC4064_25 wherein codons have been altered to introduce the amino acid changes of S33G, G87K, I385S, G402Q, and R604N relative to those positions in TIC4064.

SEQ ID NO:44 is the amino acid sequence of TIC4064_25.

SEQ ID NO:45 is a synthetic bacterial coding sequence encoding TIC4064_26 wherein codons have been altered to introduce the amino acid changes of G87K, F199Y, V325A, S331A, and Q631T relative to those positions in those positions in TIC4064.

SEQ ID NO:46 is the amino acid sequence of TIC4064_26.

SEQ ID NO:47 is a synthetic bacterial coding sequence encoding TIC4064_27 wherein codons have been altered to introduce the amino acid changes of G87S, I308C, V325A, S331A, and Q631T relative to those positions in TIC4064.

SEQ ID NO:48 is the amino acid sequence of TIC4064_27.

SEQ ID NO:49 is a synthetic bacterial coding sequence encoding TIC4064_10 wherein codons have been altered to introduce the amino acid change of S94T relative to that position in TIC4064.

SEQ ID NO:50 is the amino acid sequence of TIC4064_10.

SEQ ID NO:51 is a synthetic bacterial coding sequence encoding TIC4064_11 wherein codons have been altered to introduce the amino acid change of G87K relative to that position in TIC4064.

SEQ ID NO:52 is the amino acid sequence of TIC4064_11.

DETAILED DESCRIPTION OF THE INVENTION

One problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially on or in plants.

Novel pesticidal proteins exemplified by TIC4064 and engineered amino acid sequence variants are disclosed herein and address each of these problems in the art, particularly against a broad spectrum of Lepidopteran insect pests of crop plants, and for instance against Black armyworm (*Spodoptera cosmioides*), Black cutworm (*Agrotis ipsilon*), Corn earworm (*Helicoverpa zea*), European corn borer (*Ostrinia nubilalis*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sunflower looper (*Rachiplusia nu*), Tobacco budworm (*Heliothis virescens*), and Velvet bean caterpillar (*Anticarsia gemmatalis*).

Reference in this application to TIC4064, "TIC4064 protein", "TIC4064 protein toxin", "TIC4064 pesticidal protein", "TIC4064-related toxins", "TIC4064-related toxins", "TIC4064 class", "TIC4064 protein toxin class", "TIC4064 toxin protein class", and the like, which are substantially interchangeable terms, refer to any novel pesticidal protein or insect inhibitory protein, that comprises, that consists of, that is substantially homologous to, that is similar to, or that is derived from any pesticidal protein or insect inhibitory protein sequence of TIC4064 (SEQ ID NO:2), and the amino acid sequence variant TIC4064 toxin proteins, TIC40641 (SEQ ID NO:4), TIC4064_2 (SEQ ID NO:6), TIC4064_3 (SEQ ID NO:8), TIC4064_4 (SEQ ID NO:10), TIC4064_5 (SEQ ID NO:12), TIC4064_6 (SEQ ID NO:14), TIC4064_12_1 (SEQ ID NO:16), TIC4064_12_2 (SEQ ID NO:18), TIC4064_13 (SEQ ID NO:20), TIC4064_14 (SEQ ID NO:22), TIC4064_15 (SEQ ID NO:24), TIC4064_16 (SEQ ID NO:26), TIC4064_17 (SEQ ID NO:28), TIC4064_18 (SEQ ID NO:30), TIC4064_19 (SEQ ID NO:32), TIC4064_20 (SEQ ID NO:34), TIC4064_21 (SEQ ID NO:36), TIC4064_22 (SEQ ID NO:38), TIC4064_23 (SEQ ID NO:40), TIC4064_24 (SEQ ID NO:42), TIC4064_25 (SEQ ID NO:44), TIC4064_26 (SEQ ID NO:46). TIC4064_27 (SEQ ID NO:48), TIC4064_11 (SEQ ID NO:50), and TIC4064_11 (SEQ ID NO:52) and pesticidal or insect inhibitory segments, or combinations thereof, that confer activity against Lepidopteran pests, including any protein exhibiting pesticidal or insect inhibitory activity if alignment of such protein with TIC4064 results in an amino acid sequence of identity of any fraction percentage from about 98% to about 100% percent. The TIC4064 proteins include both the plastid-targeted and non-plastid targeted forms of the proteins.

The term "segment" or "fragment" is used in this application to describe consecutive amino acid or nucleic acid sequences that are shorter than the complete amino acid or nucleic acid sequence describing TIC4064 or a TIC4064 variant protein or the respective nucleotide sequences encoding such amino acid sequences. A segment or fragment exhibiting insect inhibitory activity is also disclosed in this application if alignment of such segment or fragment, with the corresponding section of the TIC4064 protein set forth in SEQ ID NO:2, the TIC4064_1 protein set forth in SEQ ID NO:4, the TIC4064_2 protein set forth in SEQ ID NO:6, the TIC4064_3 protein set forth in SEQ ID NO:8, the TIC4064_4 protein set forth in SEQ ID NO:10, the TIC4064_5 protein set forth in SEQ ID NO:12, the TIC4064_6 protein set forth in SEQ ID NO:14, the TIC4064_12_1 protein set forth in SEQ ID NO:16, the TIC4064_12_2 protein set forth in SEQ ID NO:18, the TIC4064_13 protein set forth in SEQ ID NO:20, the TIC4064_14 protein set forth in SEQ ID NO:22, the TIC4064_15 protein set forth in SEQ ID NO:24, the TIC4064_16 protein set forth in SEQ ID NO:26, the TIC4064_17 protein set forth in SEQ ID NO:28, the TIC4064_18 protein set forth in SEQ ID NO:30, the TIC4064_19 protein set forth in SEQ ID NO:32, the TIC4064_20 protein set forth in SEQ ID NO:34, the TIC4064_21 protein set forth in SEQ ID NO:36, the TIC4064_22 protein set forth in SEQ ID NO:38, the TIC4064_23 protein set forth in SEQ ID NO:40, the TIC4064_24 protein set forth in SEQ ID NO:42, the TIC4064_25 protein set forth in SEQ ID NO:44, the TIC4064_26 protein set forth in SEQ ID NO:46, the TIC4064_27 protein set forth in SEQ ID NO:48, the TIC4064_10 protein set forth in SEQ ID NO:50, or the TIC4064_11 protein set forth in SEQ ID NO:52, results in amino acid sequence identity of any fraction percentage from about 85 to about 100 percent between the segment or fragment and the corresponding segment of amino acids within the TIC4064, or TIC4064 amino acid sequence variant proteins. A fragment as described herein may comprise at least 50, at least 100, at least 250, at least 400, at least 500, at least 600, at least 800, or at least 1000 contiguous amino acid residues of TIC4064, or of a TIC4064 amino acid sequence variant protein. A fragment as described herein may display the pesticidal activity of any of TIC4064, or of a TIC4064 amino acid sequence variant protein.

Reference in this application to the terms "active" or "activity", "pesticidal activity" or "pesticidal" or "insecticidal activity", "insect inhibitory", "pesticidally effective" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop) containing an effective amount of the TIC4064 toxin protein class protein or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry, Vip, and Cyt proteins available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC4064 protein toxin class. However, reference to a pest can also include Coleopteran, Hemipteran and Homopteran insect pests of plants, as well as nematodes and fungi when toxic agents targeting these pests are co-localized or present together with the TIC4064 protein or the amino acid sequence variant TIC4064 proteins or a protein that is 85 to about 100 percent identical to TIC4064 protein or the amino acid sequence variant TIC4064 proteins. The phrases "present together" and "co-located" are intended to include any instance of which a target insect pest has been contacted by the TIC4064 protein toxin class as well as any other toxic agent also present in a pesticidally effective amount relative to the target insect pest. "Contacted" is intended to refer to being present in the diet of the target pest, and the diet is, at least in part, consumed or ingested by the target pest in an amount sufficient to deliver to the target pest a pesticidally effective amount of the toxic agent and TIC4064 class toxin protein.

The TIC4064 protein or amino acid sequence variant TIC4064 proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the family Noctuidae, e.g., Fall armyworm (*Spodoptera frugiperda*), Beet armyworm (*Spodoptera exigua*), Black armyworm (*Spodoptera cosmioides*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), Sugarcane borer (*Diatraea saccharalis*), Sunflower looper (*Rachiplusia nu*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), Sunflower looper (*Rachiplusia nu*), South American podworm (*Helicoverpa gelotopoeon*), western cutworm (*Agrotis orthogonia*); borers, casebearers, webworms, coneworms, cabbageworms and skeletonizers from the Family Pyralidae, e.g., European corn borer (*Ostrinia nubilalis*), navel orange worm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), surgarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean pod worm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leaf miner (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leaf miner (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism nor at the location within the genome in which it is naturally found. Similarly, a nucleotide sequence encoding an insecticidal protein or any naturally occurring insecticidal variant of that protein would be an isolated nucleotide sequence so long as the coding sequence was not within the DNA of the organism from which the sequence encoding the protein is naturally found. A synthetic or artificial nucleotide sequence encoding the amino acid sequence of the naturally occurring insecticidal protein or a variant sequence thereof would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium. A protein would be isolated if it were produced in a space in which it was not normally found to be produced in nature, i.e. in a transgenic or recombinant cell, in a transgenic or recombinant bacterium. Proteins and polynucleotide sequences/coding sequences can be isolated from the organism in which these are produced, i.e. any number of means known in the art, such as filtration, precipitation, capture (using various molecules which exhibit affinity specifically to the protein or nucleic acid structure), and the like, further "isolating" the molecules from constituents that create an impurity and the like. A recombinant cell, whether plant or bacterium, by its very nature is not naturally occurring, is isolated, and so is not a product of nature, and so is patentable in every territory in the world on this basis. Similarly, transgenic plants and plant products are not products of nature, not naturally occurring, and so are also isolated from other natural products and phenomenon and so are thus patentable subject matter in every territory.

Reference in this application to the term "self-limiting gene" refers to a gene that limits survival of the host, resulting in a reduction in the host population. Such technology is offered by Oxitech Ltd. and other unrelated entities. Transgenic male insects carrying one or more transgenic self-limiting genes are released and reproduce with wild females. As a result, the progeny inherit a copy of the self-limiting gene. The self-limiting gene disrupts the proper functioning of the insects' cells by over-producing a protein in them, interfering with the cells' ability to produce other essential proteins needed for development. By disrupting the insect's normal development, the gene prevents it from surviving to adulthood. For example, the self-limiting Diamondback Moth (*Plutella xylostella*) strain OX4319L was developed by Oxitech Ltd and carries a male-selecting gene that utilizes sequences from the sex determination gene doublesex (dsx). The gene expresses sex-alternate splicing, to engineer female-specific expression of the self-limiting gene which prevents survival of female offspring beyond the larval stage and allows for production of male only cohorts of self-limiting moths. After being released, males mate with pest females, leading to a reduction in the number of female offspring in the next generation, thereby locally suppressing *P. xylostella* populations. To facilitate the rearing of large numbers of males for release within diamondback moth production facilities, the expression of female-specific dsx within the OX4319L strain is repressed by the addition of tetracycline, or suitable analogs, into the larval feed. OX4319L also expresses the fluorescent protein, DsRed, to permit the effective monitoring of the presence of this strain in the field (Jin et al., 2013. Engineered female-specific lethality for control of pest Lepidoptera. ACS Synthetic Biology, 2: 160-166). This self-limiting technology, when applied in the field with plants containing the toxin genes of the present invention, can delay or prevent the onset of resistance of pest species targeted for control by the toxin genes and proteins of the present invention, thus giving a greater durability of any plant product containing the toxin genes and proteins of the present invention. Each of the insect species as set forth in this specification at paragraph [0086] are intended to be within the scope of those that are susceptible to, and thus amenable to reliance upon, the self-limiting technology described herein.

As described further in this application, an open reading frame (ORF) encoding TIC4064 (SEQ ID NO:1) was discovered in DNA obtained from *Bacillus thuringiensis* strain EG9820. The coding sequence was cloned and expressed in microbial host cells to produce recombinant proteins used in bioassays. Bioassay using microbial host cell-derived proteins of TIC4064 demonstrated activity against the Lepidopteran species Black cutworm (BCW, *Agrotis ipsilon*), Corn earworm (CEW, *Helicoverpa zea*), European corn borer (ECB, *Ostrinia nubilalis*), Southern armyworm (SAW, *Spodoptera eridania*), Soybean looper (SBL, *Chrysodeixis includens*), Southwestern corn borer (SWC, *Diatraea grandiosella*), Tobacco budworm (TBW, *Heliothis virescens*), Sunflower looper (SFL, *Rachiplusia nu*), and Velvet bean caterpillar (VBC, *Anticarsia gemmatalis*). Engineered bacterial expressed amino acid sequence variants were produced using the TIC4064 amino acid sequence resulting in the amino acid sequence variants TIC4064_20 (SEQ ID NO:34), TIC4064_21 (SEQ ID NO:36), TIC4064_22 (SEQ ID NO:38), TIC4064_23 (SEQ ID NO:40), TIC4064_24 (SEQ ID NO:42), TIC4064_25 (SEQ ID NO:44), TIC4064_26 (SEQ ID NO:46) TIC4064_27 (SEQ ID NO:48), TIC4064_10 (SEQ ID NO:50), and TIC4064_11 (SEQ ID NO:52) encoded by SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and SEQ ID NO:51, respectively.

Synthetic (artificial) coding sequences designed for use in a plant cell were produced to express TIC4064 and amino acid sequence variants of TIC4064 wherein an alanine codon has been inserted as the second codon in the open reading frame, resulting in TIC4064_1 (SEQ ID NO:4), and the amino acid sequence variants TIC4064_2 (SEQ ID NO:6), TIC4064_3 (SEQ ID NO:8), TIC4064_4 (SEQ ID NO:10), TIC4064_5 (SEQ ID NO:12), TIC4064_6 (SEQ ID NO:14), TIC4064_12_1 (SEQ ID NO:16), TIC4064_12_2 (SEQ ID NO:18), TIC4064_13 (SEQ ID NO:20), TIC4064_14 (SEQ ID NO:22), TIC4064_15 (SEQ ID NO:24), TIC4064_16 (SEQ ID NO:26), TIC4064_17 (SEQ ID NO:28), TIC4064_18 (SEQ ID NO:30), and TIC4064_19 (SEQ ID NO:32), encoded by the coding sequences SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31, encoding TIC4064_1 (SEQ ID NO:4), respectively.

Table 1 shows the bacterial and plant toxins and the amino acid sequence modifications relative to TIC4064 and TIC4064_1.

TABLE 1

TIC4064, TIC4064_1, and amino acid sequence variants.

| Toxin | DNA SEQ ID NO: | Protein SEQ ID NO: | Protein Sequence Type and Relationship to Others | Amino Acid Modifications Relative to TIC4064 (bacterial) | Amino Acid Modifications Relative to TIC4064_1 (plant) |
|---|---|---|---|---|---|
| TIC4064 | 1 | 2 | Bacterial sequence | | |
| TIC4064_1 | 3 | 4 | Plant sequence equivalent to TIC4064 | Insertion of A at position 2 | |
| TIC4064_2 | 5 | 6 | Plant sequence truncation of TIC4064_1 | | |
| TIC4064_3 | 7 | 8 | Plant sequence | S94T | S95T |
| TIC4064_4 | 9 | 10 | Plant sequence truncation of TIC4064_3 | S94T | S95T |
| TIC4064_5 | 11 | 12 | Plant sequence | G87K | G88K |
| TIC4064_6 | 13 | 14 | Plant sequence truncation of TIC4064_5 | G87K | G88K |
| TIC4064_12_1 | 15 | 16 | Plant sequence | D84A; S94T; A510H; N512D; R604N | D85A; S95T; A511H; N513D; R605N |
| TIC4064_12_2 | 17 | 18 | Plant sequence | D84A; S94T | D85A; S95T |
| TIC4064_13 | 19 | 20 | Plant sequence truncation of TIC4064_12_1 | D84A; S94T; A510H; N512D; R604N | D85A; S95T; A511H; N513D; R605N |
| TIC4064_14 | 21 | 22 | Plant sequence | S94T; R168K; S331A | S95T; R169K; S332A |

TABLE 1-continued

TIC4064, TIC4064_1, and amino acid sequence variants.

| Toxin | DNA SEQ ID NO: | Protein SEQ ID NO: | Protein Sequence Type and Relationship to Others | Amino Acid Modifications Relative to TIC4064 (bacterial) | Amino Acid Modifications Relative to TIC4064_1 (plant) |
|---|---|---|---|---|---|
| TIC4064_15 | 23 | 24 | Plant sequence truncation of TIC4064_14 | S94T; R168K; S331A | S95T; R169K; S332A |
| TIC4064_16 | 25 | 26 | Plant sequence | S33G; G87K; I385S; G402Q; R604N | S34G; G88K; I386S; G403Q; R605N |
| TIC4064_17 | 27 | 28 | Plant sequence truncation of TIC4064_16 | S33G; G87K; I385S; G402Q; R604N | S34G; G88K; I386S; G403Q; R605N |
| TIC4064_18 | 29 | 30 | Plant sequence | G87K; W370L; H554N; R585Q | G88K; W371L; H555N; R586Q |
| TIC4064_19 | 31 | 32 | Plant sequence truncation of TIC4064_18 | G87K; W370L; H554N; R585Q | G88K; W371L; H555N; R586Q |
| TIC4064_20 | 33 | 34 | Bacterial sequence | S94T; D84A; A510H; N512D; D608A | |
| TIC4064_21 | 35 | 36 | Bacterial sequence | S94T; R168K; S331A | |
| TIC4064_22 | 37 | 38 | Bacterial sequence | S33G; S94T | |
| TIC4064_23 | 39 | 40 | Bacterial sequence | S94T; E153D; Q436I; S596Q | |
| TIC4064_24 | 41 | 42 | Bacterial sequence | G87K; W370L; H554N; R585Q | |
| TIC4064_25 | 43 | 44 | Bacterial sequence | S33G; G87K; I385S; G402Q; R604N | |
| TIC4064_26 | 45 | 46 | Bacterial sequence | G87K; F199Y; V325A; S331A; Q631T | |
| TIC4064_27 | 47 | 48 | Bacterial sequence | G87S; I308C; V325A; S331A; Q631T | |
| TIC4064_10 | 49 | 50 | Bacterial sequence equivalent to TIC4064_3 | S94T | |
| TIC4064_11 | 51 | 52 | Bacterial sequence equivalent to TIC4064_5 | G87K | |

The bacterial TIC4064 amino acid sequence variants TIC4064_20, TIC4064_21, TIC4064_22, TIC4064_23, TIC4064_24, TIC4064_25, TIC4064_26, and TIC4064_27 were assayed only against CEW to determine if the amino acid modifications affected activity of the toxin protein. None of the amino acid modifications affected activity against CEW. The bacterial TIC4064 amino acid sequence variants TIC4064_10 and TIC4064_11 were assayed against BAW, CEW, SAW, SBL, and VBC and demonstrated activity against all five insect pest species.

The plant expressed toxins TIC4064_1, TIC4064_2, TIC4064_3, TIC4064_4, TIC4064_5, TIC4064_6, TIC4064_12_1, TIC4064_12_2, TIC4064_13, TIC4064_14, TIC4064_15, TIC4064_16, TIC4064_17, TIC4064_18, and TIC4064_19 demonstrated efficacy against SBL and VBC in leaf disc assays. In screenhouse trials, TIC4064_3 demonstrated efficacy against SBL and VBC, and suppression of SAW. TIC4064_3 and TIC4064_4 also demonstrated efficacy against SBL, VBC, and SFL (Sunflower looper, *Rachiplusia nu*), and suppression of SAPW (South American podworm, *Helicoverpa gelotopoeon*) when tested in screenhouse trails.

For expression in plant cells, the TIC4064_1 (SEQ ID NO:4), TIC4064_2 (SEQ ID NO:6), TIC4064_3 (SEQ ID NO:8), TIC4064_4 (SEQ ID NO:10), TIC4064_5 (SEQ ID NO:12), TIC4064_6 (SEQ ID NO:14), TIC4064_12_1 (SEQ ID NO:16), TIC4064_12_2 (SEQ ID NO:18), TIC4064_13 (SEQ ID NO:20), TIC4064_14 (SEQ ID NO:22), TIC4064_15 (SEQ ID NO:24), TIC4064_16 (SEQ ID NO:26), TIC4064_17 (SEQ ID NO:28), TIC4064_18 (SEQ ID NO:30), and TIC4064_19 (SEQ ID NO:32) proteins can be expressed to accumulate in the cytosol or in various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. Targeting peptides or transit peptides are known in the art and when attached to a protein of interest, direct the transport of the protein of interest to a specific region in the cell, including for example the nucleus, mitochondria, endoplasmic reticulum (ER), chloroplast, apoplast, peroxisome and plasma membrane. Some targeting peptides are cleaved from the protein of interest by signal peptidases after the protein is transported through a particular membrane. For targeting to the chloroplast, proteins contain transit peptides which are around 40-50 amino acids in length. For descriptions of the use of chloroplast transit peptides, see U.S. Pat. Nos. 5,188,642 and 5,728,925. Many naturally occurring chloroplast-localized proteins are expressed from nuclear genes as precursors and are targeted to the chloroplast by a chloroplast transit peptide (CTP). Examples of such isolated CTPs include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC4064 or the amino acid sequence variant TIC4064 toxin protein to the chloroplast, a sequence encoding a chloroplast transit peptide is placed 5' in operable linkage and in frame to a synthetic (artificial) coding sequence encoding the TIC4064 or the amino acid sequence variant TIC4064 toxin protein that has been designed for expression in plant cells.

It is contemplated that additional toxin protein sequences related to TIC4064 can be created using the amino acid sequence of TIC4064 to create novel proteins with novel properties. The TIC4064 toxin proteins can be aligned to combine differences at the amino acid sequence level into novel amino acid sequence variants and making appropriate changes to the recombinant nucleic acid sequence encoding such variants.

It is contemplated that improved variants of the TIC4064 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC4064 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC4064 or derived protein variants but should retain the insect inhibitory activity of at least TIC4064.

Proteins that resemble the TIC4064 proteins can be identified and compared to each other using various computer-based algorithms known in the art (see Tables 2 through 6). Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) *Nucleic Acids Research,* 22:4673-4680). Percent amino acid identity is further calculated by the formula: 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC4064 if the protein is used in a query, e.g., in a Clustal W alignment, and the proteins of the present invention as set forth as SEQ ID NO:2 are identified as hits in such alignment in which the query protein exhibits at least 98% to about 100% amino acid sequence identity along the length of the amino acids in the query protein that is about 98%, 99%, 100%, or any fraction percentage in this range.

Exemplary bacterial expressed TIC4064 protein and amino acid sequence variants were aligned with each other using a Clustal W algorithm. A pair-wise matrix of percent amino acid sequence identities for each of the full-length proteins was created, as reported in Tables 2 and 3.

TABLE 2

Pair-wise matrix display of exemplary bacterial expressed TIC4064 protein and amino acid sequence variants.

| Sequence | TIC4064_24 | TIC4064_11 | TIC4064_25 | TIC4064_23 | TIC4064_10 | TIC4064_20 |
|---|---|---|---|---|---|---|
| TIC4064_24 | — | 99.7 (1153) | 99.4 (1149) | 99.3 (1148) | 99.6 (1151) | 99.2 (1147) |
| TIC4064_11 | 99.7 (1153) | — | 99.7 (1152) | 99.6 (1151) | 99.8 (1154) | 99.5 (1150) |
| TIC4064_25 | 99.4 (1149) | 99.7 (1152) | — | 99.2 (1147) | 99.5 (1150) | 99.1 (1146) |
| TIC4064_23 | 99.3 (1148) | 99.6 (1151) | 99.2 (1147) | — | 99.7 (1153) | 99.4 (1149) |
| TIC4064_10 | 99.6 (1151) | 99.8 (1154) | 99.5 (1150) | 99.7 (1153) | — | 99.7 (1152) |
| TIC4064_20 | 99.2 (1147) | 99.5 (1150) | 99.1 (1146) | 99.4 (1149) | 99.7 (1152) | — |

TABLE 2-continued

Pair-wise matrix display of exemplary bacterial expressed TIC4064 protein and amino acid sequence variants.

| Sequence | TIC4064_24 | TIC4064_11 | TIC4064_25 | TIC4064_23 | TIC4064_10 | TIC4064_20 |
|---|---|---|---|---|---|---|
| TIC4064_21 | 99.2 (1147) | 99.5 (1150) | 99.1 (1146) | 99.4 (1149) | 99.7 (1152) | 100 (1156) |
| TIC4064_22 | 99.5 (1150) | 99.7 (1153) | 99.6 (1151) | 99.7 (1152) | 99.9 (1155) | 99.6 (1151) |
| TIC4064 | 99.7 (1152) | 99.9 (1155) | 99.6 (1151) | 99.7 (1152) | 99.9 (1155) | 99.6 (1151) |
| TIC4064_26 | 99.4 (1149) | 99.7 (1152) | 99.3 (1148) | 99.2 (1147) | 99.5 (1150) | 99.1 (1146) |
| TIC4064_27 | 99.3 (1148) | 99.6 (1151) | 99.2 (1147) | 99.2 (1147) | 99.5 (1150) | 99.1 (1146) |

TABLE 3

Pair-wise matrix display of exemplary bacterial expressed TIC4064 protein and amino acid sequence variants.

| Sequence | TIC4064_21 | TIC4064_22 | TIC4064 | TIC4064_26 | TIC4064_27 |
|---|---|---|---|---|---|
| TIC4064_24 | 99.2 (1147) | 99.5 (1150) | 99.7 (1152) | 99.4 (1149) | 99.3 (1148) |
| TIC4064_11 | 99.5 (1150) | 99.7 (1153) | 99.9 (1155) | 99.7 (1152) | 99.6 (1151) |
| TIC4064_25 | 99.1 (1146) | 99.6 (1151) | 99.6 (1151) | 99.3 (1148) | 99.2 (1147) |
| TIC4064_23 | 99.4 (1149) | 99.7 (1152) | 99.7 (1152) | 99.2 (1147) | 99.2 (1147) |
| TIC4064_10 | 99.7 (1152) | 99.9 (1155) | 99.9 (1155) | 99.5 (1150) | 99.5 (1150) |
| TIC4064_20 | 100 (1156) | 99.6 (1151) | 99.6 (1151) | 99.1 (1146) | 99.1 (1146) |
| TIC4064_21 | — | 99.6 (1151) | 99.6 (1151) | 99.1 (1146) | 99.1 (1146) |
| TIC4064_22 | 99.6 (1151) | — | 99.8 (1154) | 99.4 (1149) | 99.4 (1149) |
| TIC4064 | 99.6 (1151) | 99.8 (1154) | — | 99.6 (1151) | 99.6 (1151) |
| TIC4064_26 | 99.1 (1146) | 99.4 (1149) | 99.6 (1151) | — | 99.7 (1153) |
| TIC4064_27 | 99.1 (1146) | 99.4 (1149) | 99.6 (1151) | 99.7 (1153) | — |

Exemplary plant expressed TIC4064 protein and amino acid sequence variants were aligned with each other using a Clustal W algorithm. A pair-wise matrix of percent amino acid sequence identities for each of the full-length proteins was created, as reported in Tables 4 and 5. Table 4 shows alignment of the full-length plant expressed proteins. Table 5 shows alignment of the truncated plant expressed proteins in the absence of the protoxin domain.

TABLE 4

Pair-wise matrix display of exemplary full-length plant expressed TIC4064_1 protein and amino acid sequence variants.

| Sequence | TIC4064_3 | TIC4064_14 | TIC4064_12_1 | TIC4064_12_2 | TIC4064_1 | TIC4064_18 | TIC4064_5 | TIC4064_16 |
|---|---|---|---|---|---|---|---|---|
| TIC4064_3 | — | 99.8 (1155) | 99.7 (1153) | 99.9 (1156) | 99.9 (1156) | 99.6 (1152) | 99.8 (1155) | 99.5 (1151) |
| TIC4064_14 | 99.8 (1155) | — | 99.5 (1151) | 99.7 (1154) | 99.7 (1154) | 99.4 (1150) | 99.7 (1153) | 99.3 (1149) |
| TIC4064_12_1 | 99.7 (1153) | 99.5 (1151) | — | 99.7 (1154) | 99.6 (1152) | 99.2 (1148) | 99.5 (1151) | 99.1 (1147) |
| TIC4064_12_2 | 99.9 (1156) | 99.7 (1154) | 99.7 (1154) | — | 99.8 (1155) | 99.5 (1151) | 99.7 (1154) | 99.4 (1150) |
| TIC4064_1 | 99.9 (1156) | 99.7 (1154) | 99.6 (1152) | 99.8 (1155) | — | 99.7 (1153) | 99.9 (1156) | 99.6 (1152) |
| TIC4064_18 | 99.6 (1152) | 99.4 (1150) | 99.2 (1148) | 99.5 (1151) | 99.7 (1153) | — | 99.7 (1154) | 99.4 (1150) |
| TIC4064_5 | 99.8 (1155) | 99.7 (1153) | 99.5 (1151) | 99.7 (1154) | 99.9 (1156) | 99.7 (1154) | — | 99.7 (1153) |

TABLE 4-continued

Pair-wise matrix display of exemplary full-length plant expressed TIC4064_1 protein and amino acid sequence variants.

| Sequence | TIC4064_3 | TIC4064_14 | TIC4064_12_1 | TIC4064_12_2 | TIC4064_1 | TIC4064_18 | TIC4064_5 | TIC4064_16 |
|---|---|---|---|---|---|---|---|---|
| TIC4064_16 | 99.5 (1151) | 99.3 (1149) | 99.1 (1147) | 99.4 (1150) | 99.6 (1152) | 99.4 (1150) | 99.7 (1153) | — |

TABLE 5

Pair-wise matrix display of exemplary truncated plant expressed TIC4064_1 protein and amino acid sequence variants.

| Sequence | TIC4064_13 | TIC4064_15 | TIC4064_4 | TIC4064_2 | TIC4064_17 | TIC4064_19 | TIC4064_6 |
|---|---|---|---|---|---|---|---|
| TIC4064_13 | — | 99.1 (657) | 98.5 (653) | 98.3 (652) | 98.5 (653) | 98.6 (654) | 98.2 (651) |
| TIC4064_15 | 99.1 (657) | — | 98.8 (655) | 98.6 (654) | 98.8 (655) | 98.9 (656) | 98.5 (653) |
| TIC4064_4 | 99.4 (653) | 99.7 (655) | — | 99.8 (656) | 99.1 (651) | 99.2 (652) | 99.7 (655) |
| TIC4064_2 | 99.2 (652) | 99.5 (654) | 99.8 (656) | — | 99.2 (652) | 99.4 (653) | 99.8 (656) |
| TIC4064_17 | 98.5 (653) | 98.8 (655) | 98.2 (651) | 98.3 (652) | — | 98.9 (656) | 98.5 (653) |
| TIC4064_19 | 98.6 (654) | 98.9 (656) | 98.3 (652) | 98.5 (653) | 98.9 (656) | — | 98.6 (654) |
| TIC4064_6 | 99.1 (651) | 99.4 (653) | 99.7 (655) | 99.8 (656) | 99.4 (653) | 99.5 (654) | — |

In addition to percent identity, TIC4064 and the amino acid sequence variants of TIC4064 can also be related by primary structure (conserved amino acid motifs), by length and by other characteristics. Characteristics of the TIC4064 protein toxin class are reported in Table 6.

TABLE 6

Selected characteristics of TIC4064 and amino acid sequence variant protein toxins.

| Protein | Molecular Weight (in Daltons) | Amino Acid Length | Isoelectric Point | Charge at PH 7.0 | No. of Hydrophobic Amino Acids | No. of Polar Amino Acids | No. of Strongly Basic (−) Amino Acids | No. of Strongly Acidic Amino Acids |
|---|---|---|---|---|---|---|---|---|
| TIC4064 | 129589.10 | 1156 | 5.5324 | −15.0 | 569 | 587 | 130 | 131 |
| TIC4064_1 | 129660.18 | 1157 | 5.5324 | −15.0 | 570 | 587 | 130 | 131 |
| TIC4064_2 | 73313.27 | 657 | 8.3133 | 8.5 | 337 | 320 | 70 | 56 |
| TIC4064_3 | 129674.20 | 1157 | 5.5324 | −15.0 | 570 | 587 | 130 | 131 |
| TIC4064_4 | 73327.30 | 657 | 8.3133 | 8.5 | 337 | 320 | 70 | 56 |
| TIC4064_5 | 129731.30 | 1157 | 5.6047 | −14.0 | 569 | 588 | 131 | 131 |
| TIC4064_6 | 73384.40 | 657 | 8.4925 | 9.5 | 336 | 321 | 71 | 56 |
| TIC4064_12_1 | 129653.23 | 1157 | 5.6679 | −13.5 | 571 | 586 | 131 | 130 |
| TIC4064_12_2 | 129630.19 | 1157 | 5.6033 | −14.0 | 571 | 586 | 130 | 130 |
| TIC4064_13 | 73989.10 | 663 | 8.6576 | 11.0 | 340 | 323 | 73 | 56 |
| TIC4064_14 | 129630.19 | 1157 | 5.5324 | −15.0 | 571 | 586 | 130 | 130 |
| TIC4064_15 | 73966.06 | 663 | 8.4917 | 9.5 | 340 | 323 | 72 | 57 |
| TIC4064_16 | 129704.19 | 1157 | 5.5324 | −15.0 | 568 | 589 | 130 | 131 |
| TIC4064_17 | 74040.06 | 663 | 8.4917 | 9.5 | 337 | 326 | 72 | 57 |
| TIC4064_18 | 129607.15 | 1157 | 5.4687 | −15.0 | 569 | 588 | 129 | 131 |
| TIC4064_19 | 73943.02 | 663 | 8.4899 | 9.0 | 338 | 325 | 71 | 57 |
| TIC4064_20 | 129582.15 | 1156 | 5.6679 | −13.5 | 570 | 586 | 131 | 130 |
| TIC4064_21 | 129582.15 | 1156 | 5.6679 | −13.5 | 570 | 586 | 131 | 130 |
| TIC4064_22 | 129573.10 | 1156 | 5.5324 | −15.0 | 570 | 586 | 130 | 131 |
| TIC4064_23 | 129615.18 | 1156 | 5.5315 | −15.0 | 570 | 586 | 130 | 131 |
| TIC4064_24 | 129536.07 | 1156 | 5.4687 | −15.5 | 568 | 588 | 129 | 131 |
| TIC4064_25 | 129633.11 | 1156 | 5.5324 | −15.0 | 567 | 589 | 130 | 131 |
| TIC4064_26 | 129605.14 | 1156 | 5.6047 | −14.0 | 569 | 587 | 131 | 131 |
| TIC4064_27 | 129538.02 | 1156 | 5.5324 | −15.0 | 569 | 587 | 130 | 131 |
| TIC4064_10 | 129603.12 | 1156 | 5.5324 | −15.0 | 569 | 587 | 130 | 131 |
| TIC4064_11 | 129660.22 | 1156 | 5.6047 | −14.0 | 568 | 588 | 131 | 131 |

As described further in the Examples of this application, synthetic nucleic acid molecule sequences encoding TIC4064_1, TIC4064_2, TIC4064_3, TIC4064_4, TIC4064_5, TIC4064_6, TIC4064_12_1, TIC4064_12_2, TIC4064_13, TIC4064_14, TIC4064_15, TIC4064_16, TIC4064_17, TIC4064_18, and TIC4064_19 were designed for use in plants, encoded by SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, SEQ ID NO:23, SEQ ID NO:25, SEQ ID NO:27, SEQ ID NO:29, and SEQ ID NO:31, respectively. Each of the variant proteins has an alanine amino acid added at position two (2) of the amino acid sequence, immediately following the initiating methionine relative to the TIC4064 protein.

Expression cassettes and vectors containing a recombinant nucleic acid molecule sequence can be constructed and introduced into plants, in particular corn, soybean or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), in U.S. Pat. No. 5,750,871 (canola), 7,026,528 (wheat), and 6,365,807 (rice), and in Arencibia et al. (1998) *Transgenic Res.* 7:213-222 (sugarcane)) all of which are incorporated herein by reference in their entirety. Transformed cells can be regenerated into transformed plants that express TIC4064 and amino acid sequence variant proteins and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode bacterial and plant expressed TIC4064, TIC4064_1 or TIC4064 amino acid sequence variant proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC4064_1 protein or protein variant encoding sequence for expression of the protein in plants or a Bt-functional promoter operably linked to a TIC4064 protein or TIC4064 protein variant encoding sequence for expression of the protein in a Bt bacterium or other *Bacillus* species. Other elements can be operably linked to the TIC4064 protein toxin class protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and SEQ ID NO:51 that encodes the respective polypeptides or proteins having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:52. A heterologous promoter can also be operably linked to synthetic DNA coding sequences encoding a plastid targeted TIC4064_1 or TIC4064_1 protein variant. The codons of a recombinant nucleic acid molecule encoding for proteins disclosed herein can be substituted by synonymous codons (known in the art as a silent substitution).

A recombinant DNA construct comprising a sequence encoding one or more proteins from the TIC4064 protein toxin class can further comprise a region of DNA that encodes for one or more insect inhibitory agents which can be configured to concomitantly express or co-express with another protein from the TIC4064 protein toxin class, another insect control protein toxin, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecule is under separate promoter control or some combination thereof. The proteins of this invention can be expressed from a multi-gene expression system in which one or more proteins of the TIC4064 protein toxin class are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC4064 protein toxin class encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC4064 protein toxin class encoding sequence in a host cell, or subsequent expression of the encoded polypeptide. An exogenous recombinant polynucleotide or recombinant DNA construct that comprises a TIC4064 protein toxin class encoding sequence and that is introduced into a host cell is referred in this application as a "transgene".

Transgenic bacteria, transgenic plant cells, transgenic plants, and transgenic plant parts that contain a recombinant polynucleotide that expresses any one or more of TIC4064. TIC4064_1, or the amino acid sequence variants thereof, or a related family toxin protein encoding sequence are provided herein. The term "bacterial cell" or "bacterium" can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, brassica (e.g. canola), carrot, cassava, castor, cauliflower, celery, chickpea, Chinese cabbage, citrus, coconut, coffee, corn (i.e. maize such as sweet corn or field corn), clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insecticidally effective Lepidoptera-inhibitory amounts of a protein from the TIC4064 protein toxin class are provided. Such plants can be made by introducing a recombinant polynucleotide that encodes any of the proteins provided in this application into a plant cell, and selecting a plant derived from said plant cell that expresses an insecticidally effective Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC4064 toxin protein class protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC4064 protein.

Plants expressing proteins from the TIC4064 protein toxin class can be crossed by breeding with transgenic events expressing other toxin proteins and/or expressing other transgenic traits such as herbicide tolerance genes, genes conferring yield or stress tolerance traits, and the like, or such traits can be combined in a single stacked vector so that the traits are all linked.

As further described in the Examples, TIC4064 protein toxin class encoding sequences and sequences having a substantial percentage identity to the TIC4064 protein toxin class can be identified using methods known to those of ordinary skill in the art such as polymerase chain reaction (PCR), thermal amplification, and hybridization. For example, the proteins from the TIC4064 protein toxin class can be used to produce antibodies that bind specifically to related proteins and can be used to screen for and to find other protein members that are closely related.

Furthermore, nucleotide sequences encoding proteins in the TIC4064 toxin protein class can be used as probes and primers for screening to identify other members of the class using thermal-cycle or isothermal amplification and hybridization methods. For example, oligonucleotides derived from sequences as set forth in SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31 can be used to determine the presence or absence of a protein from the TIC4064 protein toxin class in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 can be used to detect a TIC4064_1, TIC4064_2, TIC4064_3, TIC4064_4, TIC4064_5, TIC4064_6, TIC4064_12_1, TIC4064_12_2, TIC4064_13, TIC4064_14, TIC4064_15, TIC4064_16, TIC4064_17, TIC4064_18, or TIC4064_19 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and SEQ ID NO:51. Such "mutagenesis" oligonucleotides are useful for identification of TIC4064 protein toxin class amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC4064 and TIC4064 amino acid sequence variants. This application contemplates the use of these and other identification methods known to those of ordinary skill in the art, to identify TIC4064 and TIC4064 amino acid sequence variant protein-encoding sequences and sequences having a substantial percentage identity to TIC4064 and TIC4064 amino acid sequence variants protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC4064 or TIC4064 amino acid sequence variant proteins to derive additional useful embodiments including assembly of segments of TIC4064 or TIC4064 amino acid sequence variant proteins with segments of diverse proteins different from TIC4064 or TIC4064 amino acid sequence variant proteins and related proteins. The TIC4064 or TIC4064 amino acid sequence variant proteins may be subjected to alignment to each other and to other *Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC4064 or TIC4064 amino acid sequence variant proteins are disclosed in this application. Such methods can comprise growing a plant comprising an insect- or Lepidoptera-inhibitory amount of a TIC4064 or TIC4064 amino acid sequence variant toxin protein. In certain embodiments, such methods can further comprise any one or more of: (i) applying any composition comprising or encoding a TIC4064 or TIC4064 amino acid sequence variant toxin protein to a plant or a seed that gives rise to a plant; and (ii) transforming a plant or a plant cell that gives rise to a plant with a polynucleotide encoding a TIC4064 or TIC4064 amino acid sequence variant toxin protein. In general, it is contemplated that a TIC4064 or TIC4064 amino acid sequence variant toxin protein can be provided in a composition, provided in a microorganism, or provided in a transgenic plant to confer insect inhibitory activity against Lepidopteran insects.

In certain embodiments, a recombinant nucleic acid molecule of TIC4064 or TIC4064 amino acid sequence variant toxin protein is the insecticidally active ingredient of an insect inhibitory composition prepared by culturing recombinant *Bacillus* or any other recombinant bacterial cell transformed to express a TIC4064 or TIC4064 amino acid sequence variant toxin protein under conditions suitable to express the TIC4064 or TIC4064 amino acid sequence variant toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC4064 or TIC4064 amino acid sequence variant protein can further comprise at least one additional polypeptide that exhibits insect inhibitory activity against the same Lepidopteran insect species, but which is different from the TIC4064 or TIC4064 amino acid sequence variant toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Ser. No. 10/525, 318), Cry1C (U.S. Pat. No. 6,033,874), Cry1D, Cry1 Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NOs:2 or 4 and derivatives thereof as described in U.S. Pat. No. 7,510,878(B2), SEQ ID NO:2 or 4 and derivatives thereof as described in U.S. Pat. No. 7,812,129(B1); IPD110Aa and homologs (International Application Publication WO2019/178038 A2); TIC868 (U.S. patent Ser. No. 10/233,217), Cry1Da1_7 (U.S. patent Ser. No. 10/059,959), BCW003 (U.S. patent Ser. No. 10/703,782), TIC1100 (U.S. Pat. No. 10,494,408), TIC867 (U.S. patent Ser. No. 10/669,317), TIC867_23 (U.S. patent Ser. No. 10/611,806), TIC6757 (U.S. patent Ser. No. 10/155, 960), TIC7941 (U.S. Patent Publication 2020-0229445 A1), fern toxins toxic to lepidopteran species such as those disclosed in U.S. Pat. No. 10,227,608, and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI -220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), *Pseudomonas* toxin DP072Aa (US Patent Application Publication No. 2014/055128), and ω-Hexatoxin-Hv1a (U.S. Patent Application Publication US2014-0366227 A1).

Additional polypeptides for the control of Coleopteran, Lepidopteran, and Hemipteran insect pests, which can be combined with the insect inhibitory proteins of the TIC4064 family, can be found on the *Bacillus thuringiensis* toxin nomenclature website maintained by Neil Crickmore (on the world wide web at btnomenclature.info). Broadly, it is contemplated that any insect inhibitory protein known to those of skill in the art can be used in combination with the TIC4064 family in both in planta (combined through breeding or molecular stacking) or in a composition or formulation as a biopesticide or combination of biopesticides.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC4064 and TIC4064 amino acid sequence variant pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC4064 and Engineered Amino Acid Sequence Variants of TIC4064

A sequence encoding a novel *Bacillus thuringiensis* (Bt) pesticidal protein was identified, cloned, sequence confirmed, and tested in insect bioassay. The pesticidal protein, TIC4064, was isolated from Bt species EG9820 and represents a novel Cry9Aa-related protein. Bt strain EG9820 was initially identified as a spore forming, crystal and plasmid containing strain of Bt or Bt-like bacteria. DNA was isolated from EG9820 and sequenced. The assembled sequence was then analyzed and an open reading frame encoding the TIC4064 protein was identified by pfam analysis to hits of endotoxin domains and identity to known Cry9Aa toxins. The full length TIC4064 protein amino acid sequence exhibits 98.1% identity to GenBank accession WP_087976765 annotated as a hypothetical protein which has not been assayed against insect pest species. GenBank accession CAA41425 is 97.58% identical to the full length TIC4064 protein. CAA41425 demonstrated 70% mortality in diet bioassay to first instar larvae of *Epiphyas postvittana* (light brown apple moth), however the authors were unable to isolate sufficient amounts of protein to assay other insect pests (Gleave et al., *Journal of General Microbiology* 138: 55-62, 1992). Polymerase chain reaction (PCR) primers were designed to amplify a full length copy of the coding region for TIC4064 from total genomic DNA isolated from the Bt species EG9820. The PCR amplicon also included the translational initiation and termination codons of the coding sequence.

The TIC4064 coding sequence was cloned using methods known in the art into a Bt expression vector in operable linkage with a Bt expressible promoter. Spore and soluble protein preparations were used in bioassay. In addition, variants of TIC4064 were produced which comprised selected amino acid substitutions. The coding sequences encoding these TIC4064 amino acid sequence variants were synthesized and cloned into a bacterial expression vector used for expression of the protein in *E. coli*. Protein preparations of the TIC4064 amino acid sequence variants were used in bioassay. Table 7 shows the bacterial TIC4064 amino acid sequence variants and the amino acid substitutions that were introduced relative to the bacterial TIC4064 protein sequence.

TABLE 7

TIC4064 amino acid sequence variants and amino acid substitutions.

| Toxin | SEQ ID NO: | Amino Acid Modifications Relative to TIC4064 (SEQ ID NO: 2) | Percent Identity to WP_ 087976765 |
|---|---|---|---|
| TIC4064_20 | 34 | S94T; D84A; A510H; N512D; D608A | 97.66% |
| TIC4064_21 | 36 | S94T; R168K; S331A | 97.66% |
| TIC4064_22 | 38 | S33G; S94T | 97.92% |
| TIC4064_23 | 40 | S94T; E153D; Q4361; S596Q | 97.75% |
| TIC4064_24 | 42 | G87K; W370L; H554N; R585Q | 97.75% |
| TIC4064_25 | 44 | S33G; G87K; I385S; G402Q; R604N | 97.66% |
| TIC4064_26 | 46 | G87K; F199Y; V325A; S331A; Q631T | 97.66% |

TABLE 7-continued

| TIC4064 amino acid sequence variants and amino acid substitutions. | | | |
|---|---|---|---|
| Toxin | SEQ ID NO: | Amino Acid Modifications Relative to TIC4064 (SEQ ID NO: 2) | Percent Identity to WP_ 087976765 |
| TIC4064_27 | 48 | G87S; I308C; V325A; S331A; Q631T | 97.66% |
| TIC4064_10 | 50 | S94T | 98.01% |
| TIC4064_11 | 52 | G87K | 98.01% |

Example 2

TIC4064 and the TIC4064 Amino Acid Sequence Variants Demonstrates Lepidopteran Activity in Insect Bioassay The pesticidal proteins TIC4064, and the TIC4064 amino acid sequence variants TIC4064_20, TIC4064_21, TIC4064_22, TIC4064_23, TIC4064_24, TIC4064_25, TIC4064_26, TIC4064_27, TIC4064_10, and TIC4064_11 were expressed in either Bt or *E. coli* and assayed for toxicity to various species of Lepidoptera. TIC4064 was also assayed for toxicity to various species of Coleoptera, Hemiptera, and Diptera.

TIC4064 was assayed for toxicity to the Lepidopteran insect species Black cutworm (BCW, *Agrotis ipsilon*), Corn earworm (CEW, *Helicoverpa zea*, also known as Soybean podworm), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Southwestern corn borer (SWC, *Diatraea grandiosella*), Tobacco budworm (TBW, *Heliothis virescens*), Sunflower looper (SFL, *Rachiplusia nu*), and Velvet bean caterpillar (VBC, *Anticarsia gemmatalis*); the Coleopteran species Colorado potato beetle (CPB, *Leptinotarsa decemlineata*) and Western Corn Rootworm (WCR, *Diabrotica virgifera*); the Hemipteran species Neotropical Brown Stink Bug (NBSB, *Euschistus heros*); and the Dipteran species Yellow Fever Mosquito (YFM, *Aedes aegypti*). Bioassay using microbial host cell-derived proteins of TIC4064 demonstrated activity against the Lepidopteran species BCW, CEW, ECB, SAW, SBL, SWC, SFL, TBW, and VBC. Activity was also observed against the Dipteran species YFM.

The bacterial TIC4064 amino acid sequence variants TIC4064_20, TIC4064_21, TIC4064_22, TIC4064_23, TIC4064_24, TIC4064_25, TIC4064_26, and TIC4064_27 were assayed only against CEW to determine if the amino acid modifications affected CEW activity. All of the TIC4064 amino acid sequence variants retained activity against CEW. TIC4064_10 and TIC4064_11 were assayed against CEW, SAW, SBL and VBC and demonstrated activity against each pest species. In addition, TIC4064_10 and TIC4064_11 were assayed against Black armyworm (BAW, *Spodoptera cosmioides*) in a dilution assay. Both TIC4064_10 and TIC4064_11 demonstrated activity against BAW.

Example 3

Design of Synthetic Coding Sequences for TIC4064 and TIC4064 Amino Acid Sequence Variants for Use in Expression in Plants Synthetic (artificial) coding sequences were designed for expression in plant cells encoding TIC4064 and amino acid sequence variants of TIC4064. In addition, coding sequences were also designed which encoded TIC4064 and TIC4064 amino acid sequence variants comprising a deletion of the protoxin domain.

The synthetic sequences were synthesized, according to methods generally described in U.S. Pat. No. 5,500,365, to avoid certain inimical problem sequences such as ATTTA and A/T rich plant polyadenylation sequences while preserving the amino acid sequence of the native *Bacillus* protein. TIC4064_1 (SEQ ID NO:3) is the plant synthetic coding sequence of TIC4064, and encodes a TIC4064_1 protein (SEQ ID NO:4) which includes an additional alanine residue immediately following the initiating methionine relative to the TIC4064 protein. Synthetic coding sequences were also synthesized encoding amino acid sequence variants of TIC4064_1 wherein specific amino acids were substituted. In addition, synthetic coding sequences encoding truncations of the protoxin domain of the TIC4064_1 amino acid sequence variants were synthesized. All of the TIC4064_1 amino acid sequence variants comprised an additional alanine residue immediately following the initiating methionine. Table 8 shows each of the TIC4064_1 variants and the corresponding amino acid changes relative to both TIC4064_1 and bacterial TIC4064.

Binary plant transformation vectors comprising targeted and untargeted TIC4064_1 and the TIC4064_1 amino acid sequence variant synthetic coding sequences were constructed using methods known in the art. The resulting transformation vectors comprised a first transgene cassette for expression of the TIC4064_1 and the TIC4064_1 amino acid sequence variant pesticidal proteins which comprised a constitutive promoter, operably linked 5' to a leader, operably linked 5' to a synthetic coding sequence encoding a plastid targeted or untargeted TIC4064_1 or TIC4064_1 amino acid sequence variant protein, which was in turn operably linked 5' to a 3' UTR and; a second transgene cassette for the selection of transformed plant cells using spectinomycin selection.

TABLE 8

| Synthetic coding sequences encoding TIC4064_1, TIC4064_1 amino acid sequence variants, and truncations. | | | | | |
|---|---|---|---|---|---|
| Toxin | Synthetic Coding SEQ ID NO: | Protein SEQ ID NO: | Protein Sequence Relationship | Amino Acid Modifications Relative to TIC4064_1 (plant; SEQ ID NO: 4) | Amino Acid Modifications Relative to TIC4064 (bacterial; SEQ ID NO: 2) |
| TIC4064_1 | 3 | 4 | | | Alanine inserted at position 2 |
| TIC4064_2 | 5 | 6 | Truncation of TIC4064_1 | | |
| TIC4064_3 | 7 | 8 | | S95T | S94T |
| TIC4064_4 | 9 | 10 | Truncation of TIC4064_3 | S95T | S94T |
| TIC4064_5 | 11 | 12 | | G88K | G87K |
| TIC4064_6 | 13 | 14 | Truncation of TIC4064_5 | G88K | G87K |

TABLE 8-continued

Synthetic coding sequences encoding TIC4064_1, TIC4064_1 amino acid sequence variants, and truncations.

| Toxin | Synthetic Coding SEQ ID NO: | Protein SEQ ID NO: | Protein Sequence Relationship | Amino Acid Modifications Relative to TIC4064_1 (plant; SEQ ID NO: 4) | Amino Acid Modifications Relative to TIC4064 (bacterial; SEQ ID NO: 2) |
|---|---|---|---|---|---|
| TIC4064_12_1 | 15 | 16 | | D85A; S95T; A511H; N513D; R605N | D84A; S94T; A510H; N512D; R604N |
| TIC4064_12_2 | 17 | 18 | | D85A; S95T | D84A; S94T |
| TIC4064_13 | 19 | 20 | Truncation of TIC4064_12_1 | D85A; S95T; A511H; N513D; R605N | D84A; S94T; A510H; N512D; R604N |
| TIC4064_14 | 21 | 22 | | S95T; R169K; S332A | S94T; R168K; S331A |
| TIC4064_15 | 23 | 24 | Truncation of TIC4064_14 | S95T; R169K; S332A | S94T; R168K; S331A |
| TIC4064_16 | 25 | 26 | | S34G; G88K; I386S; G403Q; R605N | S33G; G87K; I385S; G402Q; R604N |
| TIC4064_17 | 27 | 28 | Truncation of TIC4064_16 | S34G; G88K; I386S; G403Q; R605N | S33G; G87K; I385S; G402Q; R604N |
| TIC4064_18 | 29 | 30 | | G88K; W371L; H555N; R586Q | G87K; W370L; H554N; R585Q |
| TIC4064_19 | 31 | 32 | Truncation of TIC4064_18 | G88K; W371L; H555N; R586Q | G87K; W370L; H554N; R585Q |

Example 4

TIC4064_1 and the TIC4064_1 Amino Acid Sequence Variants Demonstrate Lepidopteran Activity in Stably Transformed Soybean Plants Binary plant transformation vectors comprising transgene cassettes designed to express both plastid targeted and untargeted TIC4064_1 and TIC4064_1 amino acid sequence variant pesticidal proteins were cloned using methods known in the art. The resulting vectors were used to stably transform soybean plants. Tissues were harvested from the transformants and used in insect bioassay against various Lepidopteran insect species.

Soybean plants were transformed with the binary transformation vectors described in Example 3 using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed soybean plant was used to obtain tissue to be used as a negative control. Multiple transformation $R_0$ single-copy insertion events from each binary vector were assessed against Southern armyworm (SAW, *Spodoptera eridania*), Soybean looper (SBL, *Chrysodeixis includens*), Soybean podworm (SPW, *Helicoverpa zea*,), and Velvet bean caterpillar (VBC, *Anticarsia gemmatalis*). An efficacy rating score which ranged from 0 to 3 was assigned to each event based upon the percent leaf damage in the bioassay for each event and the percent events that shared the lowest percent range of damage (Penetrance) as shown in Table 9.

TABLE 9

Efficacy rating scores.

| Efficacy score | Percent Leaf Damage | Penetrance |
|---|---|---|
| 0 | >50% | ≥80% |
| 1 | <50% | ≥20% |
| 2 | <30% | ≥20% |
| 3 | ≤10% | ≥50% |

Table 10 shows the efficacy scores for $R_0$ stably transformed soybean plants expressing the TIC4064_1 or TIC4064_1 amino acid sequence variants described in Example 3, Table 8. The numbers in parenthesis represent the number of events that shared the lowest percent range of damage/total number of events assayed. For TIC4064_3, TIC4064_4, TIC4064_5, TIC4064_13, TIC4064_14, TIC4064_5, TIC4064_17, TIC4064_18, and TIC4064_19 multiple constructs were used to transform plants, each comprising different expression elements. The constructs expressing the toxin proteins TIC4064_3, TIC4064_4, TIC4064_13, TIC4064_14, TIC4064_15, TIC4064_17, TIC4064_18, and TIC4064_19 each included an amino terminal chloroplast transit peptide linked to the pesticidal protein for the purpose of targeting the respective protein to the chloroplast.

As can be seen in Table 10, stably transformed $R_0$ soybean plants expressing TIC4064_1 and the TIC4064_1 amino acid sequence variants demonstrated efficacy against SBL and VBC. The majority of the $R_0$ stably transformed soybean plants demonstrated efficacy or suppression of SAW.

TABLE 10

Efficacy rating scores for $R_0$ soybean plants expressing TIC4064_1 and TIC4064_1 amino acid sequence variants.

| Toxin | Construct | Plastid-targeted | SAW | SBL | SPW | VBC |
|---|---|---|---|---|---|---|
| TIC4064_1 | | No | 3 (14/19) | 3 (18/19) | 2 (7/19) | 3 (19/19) |
| TIC4064_2 | | No | 3 (15/20) | 3 (16/20) | 2 (6/20) | 3 (18/20) |
| TIC4064_3 | Construct-1 | No | 0 (16/17) | 3 (16/17) | 0 (17/17) | 3 (15/17) |
| TIC4064_3 | Construct-2 | No | 0 (19/19) | 3 (18/19) | 0 (19/19) | 3 (18/19) |
| TIC4064_3 | Construct-2 | No | 0 (19/20) | 3 (15/20) | 0 (20/20) | 3 (15/20) |
| TIC4064_3 | Construct-3 | No | 1 (6/20) | 3 (16/20) | 0 (20/20) | 3 (17/20) |
| TIC4064_3 | Construct-4 | No | 2 (9/20) | 3 (16/20) | 0 (20/20) | 3 (16/20) |

TABLE 10-continued

Efficacy rating scores for $R_0$ soybean plants expressing TIC4064_1 and TIC4064_1 amino acid sequence variants.

| Toxin | Construct | Plastid-targeted | SAW | SBL | SPW | VBC |
|---|---|---|---|---|---|---|
| TIC4064_3 | Construct-5 | Yes | 3 (11/15) | 3 (11/15) | 0 (15/15) | 3 (11/15) |
| TIC4064_3 | Construct-6 | No | 2 (16/20) | 3 (18/20) | 0 (18/20) | 3 (18/20) |
| TIC4064_3 | Construct-6 | No | 2 (13/15) | 3 (13/15) | 0 (15/15) | 3 (14/15) |
| TIC4064_4 | Construct-1 | Yes | 3 (15/15) | 3 (15/15) | 0 (15/15) | 3 (14/15) |
| TIC4064_4 | Construct-2 | No | 2 (9/20) | 3 (17/20) | 0 (20/20) | 3 (18/20) |
| TIC4064_4 | Construct-2 | No | 2 (11/15) | 3 (12/15) | 0 (15/15) | 3 (13/15) |
| TIC4064_5 | Construct-1 | No | 0 (13/16) | 3 (14/16) | 0 (16/16) | 3 (14/16) |
| TIC4064_5 | Construct-2 | No | 1 (8/20) | 3 (19/20) | 0 (20/20) | 3 (18/20) |
| TIC4064_5 | Construct-3 | No | 2 (11/20) | 3 (17/20) | 0 (20/20) | 3 (17/20) |
| TIC4064_5 | Construct-4 | No | 2 (4/7) | 3 (5/7) | 0 (7/7) | 3 (5/7) |
| TIC4064_6 | | No | 2 (5/22) | 3 (16/22) | 0 (21/22) | 3 (16/22) |
| TIC4064_12_1 | | No | 3 (13/15) | 3 (15/15) | 1 (4/15) | 3 (15/15) |
| TIC4064_12_2 | | No | 3 (11/11) | 3 (11/11) | 0 (11/11) | 3 (11/11) |
| TIC4064_13 | Construct-1 | Yes | 3 (15/15) | 3 (14/15) | 0 (12/15) | 3 (14/15) |
| TIC4064_13 | Construct-2 | No | 2 (8/10) | 3 (10/10) | 0 (10/10) | 3 (10/10) |
| TIC4064_14 | Construct-1 | Yes | 3 (4/6) | 3 (4/6) | 0 (6/6) | 3 (4/6) |
| TIC4064_14 | Construct-2 | No | 3 (9/15) | 3 (10/15) | 0 (15/15) | 3 (10/15) |
| TIC4064_15 | Construct-1 | Yes | 3 (12/15) | 3 (14/15) | 0 (15/15) | 3 (14/15) |
| TIC4064_15 | Construct-2 | No | 3 (13/15) | 3 (13/15) | 0 (15/15) | 3 (13/15) |
| TIC4064_16 | | No | 0 (15/15) | 3 (13/15) | 0 (15/15) | 3 (13/15) |
| TIC4064_17 | Construct-1 | Yes | 3 (12/15) | 3 (15/15) | 0 (14/15) | 3 (14/15) |
| TIC4064_17 | Construct-2 | No | 0 (14/14) | 3 (12/14) | 0 (14/14) | 3 (12/14) |
| TIC4064_18 | Construct-1 | Yes | 3 (10/13) | 3 (12/13) | 0 (12/13) | 3 (12/13) |
| TIC4064_18 | Construct-2 | No | 0 (10/12) | 3 (10/12) | 0 (12/12) | 3 (9/12) |
| TIC4064_19 | Construct-1 | Yes | 3 (8/9) | 3 (9/9) | 0 (9/9) | 3 (8/9) |
| TIC4064_19 | Construct-2 | No | 1 (6/15) | 3 (14/15) | 0 (15/15) | 3 (14/15) |

Selected $R_0$ events expressing TIC4064_1, TIC4064_2, TIC4064_3, TIC4064_4, and TIC4064_6 were allowed to self-pollinate and produce $R_1$ seed. The $R_1$ seed was used to grow $R_1$ plants. $R_1$ plants homozygous for the pesticidal protein expression cassette were selected for leaf disc bioassay against SAW, SBL, SPW and VBC. As can be seen in Table 11 below, $R_1$ plants expressing TIC4064_1, TIC4064_2, TIC4064_3, TIC4064_4, and TIC4064_6 demonstrated efficacy against SBL and VBC, and suppression of SAW.

TABLE 11

Efficacy rating scores for $R_1$ soybean plants expressing TIC4064_1 and TIC4064_1 amino acid sequence variants.

| Toxin | Construct | Plastid-targeted | SAW | SBL | SPW | VBC |
|---|---|---|---|---|---|---|
| TIC4064_1 | | No | 2 (7/10) | 3 (9/10) | 0 (10/10) | 3 (9/10) |
| TIC4064_2 | | No | 1 (7/10) | 3 (9/10) | 0 (10/10) | 3 (9/10) |
| TIC4064_3 | Construct-6 | No | 3 (7/13) | 3 (9/13) | 0 (13/13) | 3 (11/13) |
| TIC4064_4 | Construct-2 | No | 2 (11/14) | 3 (8/14) | 0 (14/14) | 3 (14/14) |
| TIC4064_6 | | No | 2 (4/6) | 3 (6/6) | 0 (6/6) | 3 (6/6) |

TIC4064_1, TIC4064_2, TIC4064_3, TIC4064_4, TIC4064_5, TIC4064_6, TIC4064_12_1, TIC4064_12_2, TIC4064_13, TIC4064_14, TIC4064_15, TIC4064_16, TIC4064_17, TIC4064_18, and TIC4064_19 are efficacious against SBL and VBC. TIC4064_1 and TIC4064_2 are efficacious against SAW. The majority of the TIC4064_1 amino acid sequence variants demonstrated suppression of SAW.

Example 5

TIC4064_3 and TIC4064_4 are Efficacious Against Soybean Looper, Sunflower Looper, and Velvet Bean Caterpillar and Provide Suppression of South American Podworm, Southern Armyworm, and Sunflower Looper in Screenhouse Trials Soybean plants expression TIC4064_3 and the truncated TIC4064_3, TIC4064_4 were assayed for protection against selected insect pest species in screenhouse trials in the United States and in Argentina.

In the United States, Soybean plants expressing TIC4064_3 were assayed in several locations in screenhouse trials against Southern armyworm (SAW, *Spodoptera eridania*), Soybean looper (SBL, *Chrysodeixis includens*), Soybean podworm (SPW, *Helicoverpa zea*,), and Velvet bean caterpillar (VBC, *Anticarsia gemmatalis*) in several locations. Screenhouse trials were conducted in Jerseyville, Ill. against SAW and SBL, in Union City, Tenn. against SBL, and against VBC and SPW in Waterman, Ill. The events were evaluated using a randomized complete block design. Each plot was planted in a single six (6) foot row with approximately eight (8) seeds per foot. Each event was represented in the screenhouse by three (3) separate plots, randomly located within the screenhouse. A non-transformed event served as a negative control, and this even was also assigned randomly to locations within the screenhouse.

Infestation of SPW and VBC was accomplished using adult moths. The insects were reared to pupae in an insectary in adult emergence cages, and maintained in climate-controlled incubators. The pupae were shipped to specific locations for release in the screenhouses. Approximately one thousand two hundred (1,200) to two thousand (2,000) adults were used for each release in the screenhouses. For SPW, adults were released in the screenhouse each week from the R1 to R2 stage of soybean development. With respect to VBC, adults were released in the screenhouse bi-weekly between the developmental stages of V4 to R3. Adult moths required continuous access to a ten percent (10%) sucrose solution for normal longevity and fecundity. Plastic food containers were filled with absorbent cotton and then the sugar solution was poured into the container to completely saturate the cotton. The sugar solution was replenished daily until adult activity subsided which was usually around two weeks after the final release of adults. Direct egg infestation was used for SAW since this insect does not oviposit preferentially or uniformly on soybean. Approximately two hundred fifty thousand (250,000) to three hundred twenty thousand (320,000) eggs were used for each infestation, and applied bi-weekly from R1 to R3 stage of development. Pieces of paper containing equal numbers of SAW eggs were attached to plants by folding the paper over a sturdy leaf petiole in the upper canopy and stapling the paper together securely. One paper was placed on a plant within one (1) foot of the front end of the plot, a second paper was placed on a plant in the middle of the plot, and a third paper was placed on a plant within one (1) foot of the back end of the plot.

The percent defoliation was assessed at different stages of plant development. For SAW, percent defoliation was assessed at the R2.8, R4.1, R4.8, and R6.0 developmental stages at Jerseyville, Ill. For SBL, percent defoliation was determined at the R2.0, R3.1, R4.2, and R5.5 developmental stages Union City, Tenn., and at the R5.4 and R5.8 developmental stages at Jerseyville, Ill. For VBC, percent defoliation was assessed at the R3.9, R5.0, and R5.4 developmental stages at Waterman, Ill. For SPW, percent defoliation was assessed at the R4.1, R4.7, R5.4, and R5.8 developmental stages at Waterman, Ill. A maximum percent defoliation was derived from the highest percent defoliation observed amongst the different developmental stages for each insect. Table 12 shows the average maximum percent defoliation for plants expressing TIC4064_3 for SAW, SBL, and VBC. The average maximum percent defoliation for SPW was similar to the negative control and is not presented in Table 12.

TABLE 12

Average maximum percent defoliation for soybean plants expressing TIC4064_3 in United States screenhouse trials.

| | SAW | | SBL | | VBC | |
|---|---|---|---|---|---|---|
| Location | Neg | TIC4064_3 | Neg | TIC4064_3 | Neg | TIC4064_3 |
| Jerseyville, IL | 56.5 | 9.9 | 25.0 | 0.0 | | |
| Union City, TN | | | 71.5 | 0.5 | | |
| Waterman, IL | | | | | 50.3 | 0.1 |

As can be seen in Table 12, plants expressing TIC4064_3 were efficacious in controlling SBL and VBC. In addition, plants expressing TIC4064_3 demonstrated suppression of SAW.

Screenhouse trials were also conducted in Argentina at two locations, Fran Luis, B A and Pergamino, BA for soybean plants expressing TIC4064_3 and TIC4064_4. Screenhouse trials were conducted in a similar manner as those in the United States. Each plot in the screenhouse comprised a row of forty-two (42) seeds in a two (2) meter row. Each event was represented in the screenhouse by three (3) randomly located separate plots. Screenhouse trials were conducted against the specified Lepidopteran insect pests.

The percent defoliation was assessed at different stages of plant development. For SBL, percent defoliation was assessed at the R5.0, R5.5, and R6.0 developmental stages at Fran Luis, BA and at the R4.0, R5.1, and R5.6 developmental stages at Pergamino, BA. For VBC, percent defoliation was assessed at the R5.5, R6.0, and R6.5 developmental stages at Fran Luis, BA and at the R5.0, R5.6, and R6.0 developmental stages at Pergamino, BA. For SFL, percent defoliation was assessed at the R5.0, R5.3, R5.5, and R6.0 developmental stages at Fran Luis, BA and at the R3.0, R4.0, R5.2, and R6.2 developmental stages at Pergamino, BA. For SAPW, percent defoliation was assessed at the R4.4, R5.1, R5.5, and R6.0 developmental stages at Fran Luis, BA and at the R3.0, R4.0, R5.1, R6.2 developmental stages at Pergamino, BA. A maximum percent defoliation was determined as above for each of the insect pests in each location. Table 13 shows the average maximum percent defoliation for plants expressing TIC4064_3 and TIC4064_4.

TABLE 13

Average maximum percent defoliation for soybean plants expressing TIC4064_3 and TIC4064_4 in Argentina screenhouse trials.

| Insect | Transgene | Fran Luis, BA, ARG | Pergamino, BA, ARG |
|---|---|---|---|
| SBL | Neg | 82.5 | 62.0 |
| | TIC4064_3 | 3.6 | 2.0 |
| | TIC4064_4 | 4.5 | 2.2 |
| VBC | Neg | 32.0 | 88.0 |
| | TIC4064_3 | 5.5 | 3.7 |
| | TIC4064_4 | 5.2 | 3.4 |
| SFL | Neg | 47.2 | 37.5 |
| | TIC4064_3 | 7.5 | 1.8 |
| | TIC4064_4 | 5.8 | 1.6 |
| SAPW | Neg | 18.9 | 42.7 |
| | TIC4064_3 | 5.4 | 21.3 |
| | TIC4064_4 | 3.3 | 22.8 |

As can be seen in Table 13, soybean plants expressing TIC4064_3 and TIC4064_4 were efficacious against SBL, VBC, and SFL, and demonstrated suppression of SAPW.

TIC4064_3 TIC4064_4 are efficacious against SBL, VBC, and SFL and provide suppression of SAW and SAPW.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein, wherein:

a. said pesticidal protein comprises the amino acid sequence as set forth in SEQ ID NO:8; or b. said polynucleotide segment comprises the nucleotide sequence as set forth in SEQ ID NO:7.

2. The recombinant nucleic acid molecule of claim 1:

a. expressed in a plant cell to produce a pesticidally effective amount of the pesticidal protein; or b. in operable linkage with a vector, and said vector is selected from the group consisting of a plasmid, phagemid, bacmid, cosmid, and a bacterial or yeast artificial chromosome.

3. The recombinant nucleic acid molecule of claim 1, present within a host cell, wherein said host cell is selected from the group consisting of a bacterial cell and a plant cell.

4. The recombinant nucleic acid molecule of claim 3, wherein said bacterial host cell is from a genus of bacteria selected from the group consisting of: *Agrobacterium, Rhizobium, Bacillus, Brevibacillus, Escherichia, Pseudomonas, Klebsiella, Pantoea*, and *Erwinia.*

5. The recombinant nucleic acid molecule of claim 4, wherein said *Bacillus* is *Bacillus cereus* or *Bacillus thuringiensis*, said *Brevibacillus* is a *Brevibacillus laterosporus*, and said *Escherichia* is a *Escherichia coli.*

6. The recombinant nucleic acid of claim 2, wherein said plant cell is a dicotyledonous or a monocotyledonous plant cell.

7. The recombinant nucleic acid of claim 6, wherein said plant cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said protein exhibits activity against a Lepidopteran insect.

9. The recombinant nucleic acid molecule of claim 8, wherein said Lepidopteran insect is selected from the group consisting of: Black armyworm (*Spodoptera cosmioides*), Black cutworm (*Agrotis ipsilon*), Corn earworm (*Helicoverpa zea*), European corn borer (*Ostrinia nubilalis*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sunflower looper (*Rachiplusia nu*), Tobacco budworm (*Heliothis virescens*), and Velvet bean caterpillar (*Anticarsia gemmatalis*).

10. A plant comprising the recombinant nucleic acid molecule of claim 1.

11. The plant of claim 10, wherein said plant is a monocot plant or a dicot plant, or part thereof.

12. The plant of claim 10, wherein the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

13. The plant of claim 10, wherein the part of the plant thereof is a seed and wherein said seed comprises said recombinant nucleic acid molecule.

14. An insect inhibitory composition comprising the recombinant nucleic acid molecule of claim 1.

15. The insect inhibitory composition of claim 14, defined as comprising a plant cell that expresses an insecticidally effective amount of the pesticidal protein.

16. A commodity product produced from the plant, or part thereof, of claim 10, wherein the commodity product comprises a detectable amount of said recombinant nucleic acid molecule, said pesticidal protein, or a fragment thereof.

17. The commodity product of claim 16, selected from the group consisting of corn flakes, corn cakes, corn flour, corn meal, corn silage, corn starch, corn cereal, whole or processed cotton seed, whole or processed soybean seed, soybean protein, soybean meal, soybean flour, soybean flakes, soybean bran, soybean milk, soybean cheese, and soybean wine.

18. A plant resistant to insect infestation, wherein the cells of said plant comprise the recombinant nucleic acid molecule of claim 1.

* * * * *

SEQUENCE LISTING

```
<160> NUMBER OF SEQ ID NOS: 52

<210> SEQ ID NO 1
<211> LENGTH: 3471
<212> TYPE: DNA
<213> ORGANISM: Bacillus thuringiensis
<220> FEATURE:
<221> NAME/KEY: misc_feature
<222> LOCATION: (1)..(3471)
<223> OTHER INFORMATION: Nucleic acid sequence encoding a TIC4064
      pesticidal protein obtained from Bacillus thuringiensis species
      EG9820.

<400> SEQUENCE: 1

atgaatcaaa ataaacacgg aattattggc gcttccaatt gtggttgtac gtcagataat     60

gttgcgaaat atcctttagc caacaatcca tattcatctg ctttaaattt aaattcttgt    120

caaaatagta gtattctcaa ctggattaac ataataggcg atgcagcaaa agaagcagta    180

tctattggga caacaatagt ctctcttatc acagcacctt ctcttactgg attaatttca    240

atagtatatg accttatagg taaagtacta ggaggtagta gtggacaatc catatcagat    300

ttgtctatat gtgacttatt atctattatt gatttacggg taagtcagag tgttttaaat    360

gatgggattg cagattttaa tggttctgta ctcttataca ggaactattt agaggctctg    420

gatagctgga ataagaatcc taattctgct tctgctgaag aactccgtac tcgttttaga    480

atcgctgact cagaatttga tagaatttta acacgagggt ctttaacgaa tggtggctcg    540

ttagctagac aaaatgccca aatattatta ttaccttctt ttgcgagtgc tgcatttttc    600

catttattac tactaaggga tgctactaga tatggcacta attgggggct atacaatgct    660

acacctttta taaattatca atcaaaacta gtagagctta ttgaactata tactgattat    720

tgcgtacatt ggtataatcg aggtttcaac gaactaaggc aacgaggcac tagtgctaca    780

gcttggttag aatttcatag atatcgtaga gagatgacat tgatggtatt agatatagta    840

gcatcatttt caagtcttga tattactaat tacccaatag aaacagattt tcagttgagt    900

agggtcattt atacagatcc aattggtttt gtacatcgta gtagtcttag gggagaaagt    960

tggtttagct ttgttaatag agctaatttc tcagatttag aaaatgcaat acctaatcct   1020

agaccgtctt ggtttttaaa taatatgatt atatctactg gttcacttac attgccggtt   1080

agcccaagta ctgatagagc gagggtatgg tatggaagtc gagatcgaat ttcccctgct   1140

aattcacaat ttattactga actaatctct ggacaacata cgactgctac acaaactatt   1200

ttagggcgaa atatatttag agtagattct caagcttgta atttaaatga taccacatat   1260

ggagtgaata gggcggtatt ttatcatgat gcgagtgaag gttctcaaag atccgtgtac   1320

gaggggtata ttcgaacaac tgggatagat aaccctagag ttcaaaatat taacacttat   1380

ttacctggag aaaattcaga tatcccaact ccagaagact atactcatat attaagcaca   1440

acaataaatt taacaggagg acttagacaa gtagcatcta atcgccgttc atctttagta   1500
```

```
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
ttaaattcga ctgtagacca gggaatctgg gcgatcttta aagttcgaac aacagatggt   2700
tatgcgacgt taggaaatct tgaattggta gagatcggac cgttatcggg tgaatctcta   2760
gaacgtgaac aaagggataa tgcaaaatgg agtgcagagc taggaagaaa gcgtgcagaa   2820
acagatcgcg tgtatcaaga tgccaaacaa tccatcaatc atttatttgt ggattatcaa   2880
gatcaacaat taaatccaga aatagggatg gcagatatta tggacgctca aaatcttgtc   2940
gcatcaattt cagatgtata tagcgatgca gtactgcaaa tccctggaat taactatgag   3000
atttacacag agctatccaa tcgcttacaa caagcatcgt atctgtatac gtctcgaaat   3060
gcggtgcaaa atggggactt taacagcggt ctagatagtt ggaatgcaac agcgggtgct   3120
acggtacaac aggatggtaa tacgcatttc ttagttcttt ctcattggga tgcacaagtt   3180
tctcaacaat ttagagtgca gccaaattgt aaatatgtat tacgtgtaac agcagagaaa   3240
gtaggcggcg gagacggata cgtgacaatc cgggatggtg ctcatcatac agaaacgctt   3300
acatttaatg catgtgatta tgatataaat ggcacgtacg tgactgataa tacgtatcta   3360
acaaaagaag tggtattcta ttcacataca gaacacatgt gggtagaggt aagtgaaaca   3420
gaaggtgttt tccatataga cagtgttgag ttcatggaaa cccaacagta g            3471
```

<210> SEQ ID NO 2
<211> LENGTH: 1156
<212> TYPE: PRT
<213> ORGANISM: Bacillus thuringiensis
<220> FEATURE:
<221> NAME/KEY: MISC_FEATURE
<222> LOCATION: (1)..(1156)
<223> OTHER INFORMATION: The amino acid sequence of the TIC4064
      pesticidal protein.

<400> SEQUENCE: 2

-continued

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
```

```
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845
```

```
Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020

Asn Gly  Asp Phe Asn Ser Gly  Leu Asp Ser Trp Asn  Ala Thr Ala
    1025                1030                1035

Gly Ala  Thr Val Gln Gln Asp  Gly Asn Thr His Phe  Leu Val Leu
    1040                1045                1050

Ser His  Trp Asp Ala Gln Val  Ser Gln Gln Phe Arg  Val Gln Pro
    1055                1060                1065

Asn Cys  Lys Tyr Val Leu Arg  Val Thr Ala Glu Lys  Val Gly Gly
    1070                1075                1080

Gly Asp  Gly Tyr Val Thr Ile  Arg Asp Gly Ala His  His Thr Glu
    1085                1090                1095

Thr Leu  Thr Phe Asn Ala Cys  Asp Tyr Asp Ile Asn  Gly Thr Tyr
    1100                1105                1110

Val Thr  Asp Asn Thr Tyr Leu  Thr Lys Glu Val Val  Phe Tyr Ser
    1115                1120                1125

His Thr  Glu His Met Trp Val  Glu Val Ser Glu Thr  Glu Gly Val
    1130                1135                1140

Phe His  Ile Asp Ser Val Glu  Phe Met Glu Thr Gln  Gln
    1145                1150                1155
```

<210> SEQ ID NO 3
<211> LENGTH: 3474
<212> TYPE: DNA
<213> ORGANISM: Artificial
<220> FEATURE:
<223> OTHER INFORMATION: Synthetic coding sequence encoding a TIC4064_1 pesticidal protein designed for expression in a plant cell wherein an additional alanine codon is inserted immediately following the initiating methionine codon.

<400> SEQUENCE: 3

```
atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180
```

```
gtgagcatcg ggacaaccat cgtttcgctt atcacagctc cctcgctgac gggcctcatc    240
tcaatcgttt atgacctcat tgggaaggtg ctcggcggct cgtccggcca atccattagc    300
gacctttcca tctgcgatct gctctccata attgacctgc gggtgtcgca gtcggtcctg    360
aacgacggga tagcggactt caacggcagc gtcctcctgt accgcaacta cctggaggca    420
ctggactcct ggaacaagaa tcccaacagc gccagcgcgg aggagctgcg gacgcgcttt    480
cgcatcgctg attctgagtt tgaccgaatc ctgacacgcg gctcccttac caacggcggt    540
agcctggctc gccagaacgc ccagattctg ttgctgccca gtttcgcgtc agccgcattc    600
tttcacctac ttctccttcg ggacgcaacg cgctacggga ccaattgggg attgtacaac    660
gcgacgccct tcatcaacta tcagtctaag ctcgtcgaac tgatcgaact ctacacggac    720
tactgcgtcc actggtacaa tcgtggcttt aacgagttgc gtcaacgcgg aacttctgct    780
acggcgtggc ttgagtttca cagataccgt cgtgagatga cgctaatggt cctcgacatc    840
gtggcgtcgt tcagctcgct tgacatcacc aactacccta tcgagaccga ctttcaactt    900
agccgtgtga tctacactga cccaatcggc ttcgtccatc gaagttcact ccgtggcgag    960
tcctggttct cgttcgtgaa ccgcgccaac ttcagtgacc ttgagaatgc gatccctaac   1020
ccacgcccta gctggttcct gaacaacatg attatctcta cagggagcct gaccttaccc   1080
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg gcgcgcaaca acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggatctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagg aagaccttga ggctaccaag aaggcggtgg cgagcctgtt tacccgcact   2040
cgtgacggcc tccaagtaaa tgtcacggac taccaagtgg accaggcggc caacctcgta   2100
agctgcctat cagacgagca gtacgcccac gacaagaaga tgcttctgga agccgtcaga   2160
gccgccaaac ggctatcgcg cgagcgcaac ctgctccaag atcccgactt caacactatc   2220
aacagcaccg aggagaatgg ctggaaagcc agcaacggcg tgacgattag cgagggcggc   2280
ccgttctaca agggccgcgc actacagctt gcctccgcaa gggagaacta ccctacctac   2340
atctaccaga aggtcgatgc gtcggaactt aaaccataca cacggtatcg tctcgacggg   2400
ttcgtcaaat ccagccaaga cctagagatc gacctcatcc accatcacaa agtacatctc   2460
gtcaagaatg cgcccgacaa tcttgtctct gacacttacc cggacgattc ctgttcgggt   2520
```

-continued

```
attaacagat gccaggagca gcagatggtg aacgcccaac tcgaaaccga gcaccatcac   2580

ccaatggact gctgcggtgc ggctcagacc cacgagttta gcagttacat cgacaccggc   2640

gacctgaact cgacggtgga ccagggcatc tgggcgatct tcaaggttcg taccaccgac   2700

ggctacgcga ctctcgggaa tctggaactg gtcgagatcg gcccgttgag cggcgagtcg   2760

ctggagcggg agcagaggga caacgcaaag tggtctgccg agctgggccg aaagcgagcg   2820

gagactgacc gcgtgtacca ggatgctaag caaagtatca accacctctt cgtggactat   2880

caagatcaac agctcaaccc tgagatcggg atggctgaca tcatggacgc gcagaacctg   2940

gtggcgtcga tctccgatgt gtactccgac gccgtgctcc aaatccctgg cattaactac   3000

gagatctaca cggagctgtc gaaccgcctc caacaagcga gctaccttta cacgagccgg   3060

aacgccgtac agaacggcga cttcaactcc gggctcgact catggaacgc cactgcgggc   3120

gctaccgtcc aacaagacgg caacacccac tttctcgtcc ttagccactg ggacgcccaa   3180

gtctcgcagc agtttcgcgt tcagccgaac tgcaagtatg tcctgcgcgt gaccgccgag   3240

aaggtgggcg gtggtgacgg ctacgtcacc ataagggatg gtgcccacca cacggagacc   3300

ttaacgttta acgcctgtga ttatgacatc aacggcacct atgtgacgga caatacctac   3360

ctcactaagg aagtcgtgtt ctattcccat accgagcaca tgtgggtcga ggtttcggag   3420

acggagggcg tattccacat cgacagtgtg gagttcatgg agacccagca gtga         3474
```

<210> SEQ ID NO 4
<211> LENGTH: 1157
<212> TYPE: PRT
<213> ORGANISM: Artificial
<220> FEATURE:
<223> OTHER INFORMATION: Amino acid sequence of TIC4064_1 wherein an additional alanine amino acid is inserted immediately following the initiating methionine.

<400> SEQUENCE: 4

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Gly Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190
```

-continued

```
Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605
```

```
Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                1015                1020

Gln Asn  Gly Asp Phe Asn Ser  Gly Leu Asp Ser Trp  Asn Ala Thr
```

```
    1025                1030                1035

Ala Gly  Ala Thr Val Gln Gln  Asp Gly Asn Thr His  Phe Leu Val
    1040                1045                1050

Leu Ser  His Trp Asp Ala Gln  Val Ser Gln Gln Phe  Arg Val Gln
    1055                1060                1065

Pro Asn  Cys Lys Tyr Val Leu  Arg Val Thr Ala Glu  Lys Val Gly
    1070                1075                1080

Gly Gly  Asp Gly Tyr Val Thr  Ile Arg Asp Gly Ala  His His Thr
    1085                1090                1095

Glu Thr  Leu Thr Phe Asn Ala  Cys Asp Tyr Asp Ile  Asn Gly Thr
    1100                1105                1110

Tyr Val  Thr Asp Asn Thr Tyr  Leu Thr Lys Glu Val  Val Phe Tyr
    1115                1120                1125

Ser His  Thr Glu His Met Trp  Val Glu Val Ser Glu  Thr Glu Gly
    1130                1135                1140

Val Phe  His Ile Asp Ser Val  Glu Phe Met Glu Thr  Gln Gln
    1145                1150                1155


<210> SEQ ID NO 5
<211> LENGTH: 1974
<212> TYPE: DNA
<213> ORGANISM: Artificial
<220> FEATURE:
<223> OTHER INFORMATION: Synthetic coding sequence encoding a TIC4064_2
      pesticidal protein designed for expression in a plant cell wherein
      an additional alanine codon is inserted immediately following the
      initiating methionine codon and protoxin truncation.

<400> SEQUENCE: 5

atggctaacc agaacaagca cggcatcatt ggcgcatcca actgcgggtg taccagtgac      60

aacgtggcga aatacccgct cgccaataac ccatactcat cagccctgaa cctcaacagt     120

tgtcagaaca gctccatcct gaattggatc aacatcatcg gcgacgcggc gaaggaggcg     180

gtgagcatcg ggacaaccat cgtttcgctt atcacagctc cctcgctgac gggcctcatc     240

tcaatcgttt atgacctcat tgggaaggtg ctcggcggct cgtccggcca atccattagc     300

gacctttcca tctgcgatct gctctccata attgacctgc gggtgtcgca gtcggtcctg     360

aacgacggga tagcggactt caacggcagc gtcctcctgt accgcaacta cctggaggca     420

ctggactcct ggaacaagaa tcccaacagc gccagcgcgg aggagctgcg gacgcgcttt     480

cgcatcgctg attctgagtt tgaccgaatc ctgacacgcg gctcccttac caacggcggt     540

agcctggctc gccagaacgc ccagattctg ttgctgccca gtttcgcgtc agccgcattc     600

tttcacctac ttctccttcg ggacgcaacg cgctacggga ccaattgggg attgtacaac     660

gcgacgccct tcatcaacta tcagtctaag ctcgtcgaac tgatcgaact ctacacggac     720

tactgcgtcc actggtacaa tcgtggcttt aacgagttgc gtcaacgcgg aacttctgct     780

acggcgtggc ttgagtttca cagataccgt cgtgagatga cgctaatggt cctcgacatc     840

gtggcgtcgt tcagctcgct tgacatcacc aactacccta tcgagaccga ctttcaactt     900

agccgtgtga tctacactga cccaatcggc ttcgtccatc gaagttcact ccgtggcgag     960

tcctggttct cgttcgtgaa ccgcgccaac ttcagtgacc ttgagaatgc gatccctaac    1020

ccacgcccta gctggttcct gaacaacatg attatctcta cagggagcct gaccttaccc    1080

gtcagtccca gcacagatcg cgcgagagtc tggtacggga gtcgggaccg gatctcgccc    1140

gccaactctc agttcattac tgagcttatc tccgggcagc acaccaccgc cacccagaca    1200
```

-continued

```
atactcggtc gcaacatctt ccgcgtggat tcacaggcgt gcaacctaaa cgacaccacg   1260

tacggcgtca accgcgccgt gttctaccat gacgcctcgg agggctcgca gcgtagcgtt   1320

tatgagggct acatcaggac gacgggtatc gacaacccga gagtgcagaa catcaacacc   1380

tatttgccag gcgagaacag cgacatcccg acgcccgaag actacaccca catcctcagc   1440

acaaccatca acctcacggg cgggctccgc caagttgcct cgaaccggcg gagcagcctc   1500

gttatgtacg gctggaccca caagtctctg gcgcgcaaca acaccatcaa tccagatcga   1560

atcacccaga taccactcac gaaggtggat acccgaggga ctggcgttag ttacgtcaac   1620

gatcctggat tcatcggcgg cgcgcttctc caacgcacgg accacgggtc gctgggcgtc   1680

cttcgggtac agtttccgct acacttgcgc cagcaatacc ggataagggt tcggtacgcc   1740

tcaacaacga acatcagact gtctgtcaac ggctccttcg gcaccatctc ccagaacctt   1800

ccctccacca tgcgcctcgg tgaggatctg cgctacggct ctttcgctat ccgcgagttt   1860

agcacttcaa tacgcccaac cgcgtcacct gaccagatac gcctgaccat tgaaccgtcc   1920

ttcatccggc aagaggtgta cgtggacaga atcgagttca taccagtcaa ctga         1974
```

<210> SEQ ID NO 6
<211> LENGTH: 657
<212> TYPE: PRT
<213> ORGANISM: Artificial
<220> FEATURE:
<223> OTHER INFORMATION: Amino acid sequence of TIC4064_2 wherein an additional alanine amino acid is inserted immediately following the initiating methionine, and a truncation of the protoxin domain.

<400> SEQUENCE: 6

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Gly Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
```

-continued

```
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640
```

Phe Ile Arg Gln Glu Val Tyr Val Asp Arg Ile Glu Phe Ile Pro Val
645 650 655

Asn

<210> SEQ ID NO 7
<211> LENGTH: 3474
<212> TYPE: DNA
<213> ORGANISM: Artificial
<220> FEATURE:
<223> OTHER INFORMATION: Plant synthetic coding sequence encoding a TIC4064_3 pesticidal protein designed for expression in a plant cell wherein an additional alanine codon is inserted immediately following the initiating methionine codon and comprising a mutations at S95T.

<400> SEQUENCE: 7
atggctaacc agaacaagca cggcatcatt ggcgcatcca actgcgggtg taccagtgac 60
aacgtggcga aatacccgct cgccaataac ccatactcat cagccctgaa cctcaacagt 120
tgtcagaaca gctccatcct gaattggatc aacatcatcg gcgacgcggc gaaggaggcg 180
gtgagcatcg ggacaaccat cgtttcgctt atcacagctc cctcgctgac gggcctcatc 240
tcaatcgttt atgacctcat tgggaaggtg ctcggcggct cgaccggcca atccattagc 300
gacctttcca tctgcgatct gctctccata attgacctgc gggtgtcgca gtcggtcctg 360
aacgacggga tagcggactt caacggcagc gtcctcctgt accgcaacta cctggaggca 420
ctggactcct ggaacaagaa tcccaacagc gccagcgcgg aggagctgcg gacgcgcttt 480
cgcatcgctg attctgagtt tgaccgaatc ctgacacgcg gctcccttac caacggcggt 540
agcctggctc gccagaacgc ccagattctg ttgctgccca gtttcgcgtc agccgcattc 600
tttcacctac ttctccttcg ggacgcaacg cgctacggga ccaattgggg attgtacaac 660
gcgacgccct tcatcaacta tcagtctaag ctcgtcgaac tgatcgaact ctacacggac 720
tactgcgtcc actggtacaa tcgtggcttt aacgagttgc gtcaacgcgg aacttctgct 780
acggcgtggc ttgagtttca cagataccgt cgtgagatga cgctaatggt cctcgacatc 840
gtggcgtcgt tcagctcgct tgacatcacc aactacccta tcgagaccga ctttcaactt 900
agccgtgtga tctacactga cccaatcggc ttcgtccatc gaagttcact ccgtggcgag 960
tcctggttct cgttcgtgaa ccgcgccaac ttcagtgacc ttgagaatgc gatccctaac 1020
ccacgcccta gctggttcct gaacaacatg attatctcta cagggagcct gaccttaccc 1080
gtcagtccca gcacagatcg cgcgagagtc tggtacggga gtcgggaccg gatctcgccc 1140
gccaactctc agttcattac tgagcttatc tccgggcagc acaccaccgc cacccagaca 1200
atactcggtc gcaacatctt ccgcgtggat tcacaggcgt gcaacctaaa cgacaccacg 1260
tacggcgtca accgcgccgt gttctaccat gacgcctcgg agggctcgca gcgtagcgtt 1320
tatgagggct acatcaggac gacgggtatc gacaacccga gagtgcagaa catcaacacc 1380
tatttgccag gcgagaacag cgacatcccg acgcccgaag actacaccca catcctcagc 1440
acaaccatca acctcacggg cgggctccgc caagttgcct cgaaccggcg gagcagcctc 1500
gttatgtacg gctggaccca caagtctctg gcgcgcaaca acaccatcaa tccagatcga 1560
atcacccaga taccactcac gaaggtggat acccgaggga ctggcgttag ttacgtcaac 1620
gatcctggat tcatcggcgg cgcgcttctc caacgcacgg accacgggtc gctgggcgtc 1680
cttcgggtac agtttccgct acacttgcgc cagcaatacc ggataagggt tcggtacgcc 1740
tcaacaacga acatcagact gtctgtcaac ggctccttcg gcaccatctc ccagaacctt 1800

```
ccctccacca tgcgcctcgg tgaggatctg cgctacggct ctttcgctat ccgcgagttt   1860

agcacttcaa tacgcccaac cgcgtcacct gaccagatac gcctgaccat tgaaccgtcc   1920

ttcatccggc aagaggtgta cgtggacaga atcgagttca taccagtcaa cccgacgcgg   1980

gaggcgaagg aagaccttga ggctaccaag aaggcggtgg cgagcctgtt tacccgcact   2040

cgtgacggcc tccaagtaaa tgtcacggac taccaagtgg accaggcggc caacctcgta   2100

agctgcctat cagacgagca gtacgcccac gacaagaaga tgcttctgga agccgtcaga   2160

gccgccaaac ggctatcgcg cgagcgcaac ctgctccaag atcccgactt caacactatc   2220

aacagcaccg aggagaatgg ctggaaagcc agcaacggcg tgacgattag cgagggcggc   2280

ccgttctaca agggccgcgc actacagctt gcctccgcaa gggagaacta ccctacctac   2340

atctaccaga aggtcgatgc gtcggaactt aaaccataca cacggtatcg tctcgacggg   2400

ttcgtcaaat ccagccaaga cctagagatc gacctcatcc accatcacaa agtacatctc   2460

gtcaagaatg cgcccgacaa tcttgtctct gacacttacc cggacgattc ctgttcgggt   2520

attaacagat gccaggagca gcagatggtg aacgcccaac tcgaaaccga gcaccatcac   2580

ccaatggact gctgcggtgc ggctcagacc cacgagttta gcagttacat cgacaccggc   2640

gacctgaact cgacggtgga ccagggcatc tgggcgatct tcaaggttcg taccaccgac   2700

ggctacgcga ctctcgggaa tctggaactg gtcgagatcg gcccgttgag cggcgagtcg   2760

ctggagcggg agcagaggga caacgcaaag tggtctgccg agctgggccg aaagcgagcg   2820

gagactgacc gcgtgtacca ggatgctaag caaagtatca accacctctt cgtggactat   2880

caagatcaac agctcaaccc tgagatcggg atggctgaca tcatggacgc gcagaacctg   2940

gtggcgtcga tctccgatgt gtactccgac gccgtgctcc aaatccctgg cattaactac   3000

gagatctaca cggagctgtc gaaccgcctc caacaagcga gctaccttta cacgagccgg   3060

aacgccgtac agaacggcga cttcaactcc gggctcgact catggaacgc cactgcgggc   3120

gctaccgtcc aacaagacgg caacacccac tttctcgtcc ttagccactg ggacgcccaa   3180

gtctcgcagc agtttcgcgt tcagccgaac tgcaagtatg tcctgcgcgt gaccgccgag   3240

aaggtgggcg gtggtgacgg ctacgtcacc ataagggatg gtgcccacca cacggagacc   3300

ttaacgttta acgcctgtga ttatgacatc aacggcacct atgtgacgga caatacctac   3360

ctcactaagg aagtcgtgtt ctattcccat accgagcaca tgtgggtcga ggtttcggag   3420

acggagggcg tattccacat cgacagtgtg gagttcatgg agacccagca gtga         3474
```

<210> SEQ ID NO 8
<211> LENGTH: 1157
<212> TYPE: PRT
<213> ORGANISM: Artificial
<220> FEATURE:
<223> OTHER INFORMATION: Amino acid sequence of TIC4064_3 wherein an additional alanine amino acid is inserted immediately following the initiating methionine and comprising a mutation at S95T.

<400> SEQUENCE: 8

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
```

```
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Gly Lys Val Leu Gly Gly Ser Thr Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480
```

```
Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895
```

```
Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                 1015                 1020

Gln Asn  Gly Asp Phe Asn Ser  Gly Leu Asp Ser Trp  Asn Ala Thr
    1025                 1030                 1035

Ala Gly  Ala Thr Val Gln Gln  Asp Gly Asn Thr His  Phe Leu Val
    1040                 1045                 1050

Leu Ser  His Trp Asp Ala Gln  Val Ser Gln Gln Phe  Arg Val Gln
    1055                 1060                 1065

Pro Asn  Cys Lys Tyr Val Leu  Arg Val Thr Ala Glu  Lys Val Gly
    1070                 1075                 1080

Gly Gly  Asp Gly Tyr Val Thr  Ile Arg Asp Gly Ala  His His Thr
    1085                 1090                 1095

Glu Thr  Leu Thr Phe Asn Ala  Cys Asp Tyr Asp Ile  Asn Gly Thr
    1100                 1105                 1110

Tyr Val  Thr Asp Asn Thr Tyr  Leu Thr Lys Glu Val  Val Phe Tyr
    1115                 1120                 1125

Ser His  Thr Glu His Met Trp  Val Glu Val Ser Glu  Thr Glu Gly
    1130                 1135                 1140

Val Phe  His Ile Asp Ser Val  Glu Phe Met Glu Thr  Gln Gln
    1145                 1150                 1155
```

<210> SEQ ID NO 9
<211> LENGTH: 1974
<212> TYPE: DNA
<213> ORGANISM: Artificial
<220> FEATURE:
<223> OTHER INFORMATION: Plant synthetic coding sequence encoding a TIC4064_4 pesticidal protein designed for expression in a plant cell with a truncation of the protoxin domain and a mutation at S95T.

<400> SEQUENCE: 9

```
atggctaacc agaacaagca cggcatcatt ggcgcatcca actgcgggtg taccagtgac      60

aacgtggcga aatacccgct cgccaataac ccatactcat cagccctgaa cctcaacagt     120

tgtcagaaca gctccatcct gaattggatc aacatcatcg gcgacgcggc gaaggaggcg     180

gtgagcatcg ggacaaccat cgtttcgctt atcacagctc cctcgctgac gggcctcatc     240

tcaatcgttt atgacctcat tgggaaggtg ctcggcggct cgaccggcca atccattagc     300

gacctttcca tctgcgatct gctctccata attgacctgc gggtgtcgca gtcggtcctg     360

aacgacggga tagcggactt caacggcagc gtcctcctgt accgcaacta cctggaggca     420

ctggactcct ggaacaagaa tcccaacagc gccagcgcgg aggagctgcg gacgcgcttt     480
```

cgcatcgctg attctgagtt tgaccgaatc ctgacacgcg gctcccttac caacggcggt 540
agcctggctc gccagaacgc ccagattctg ttgctgccca gtttcgcgtc agccgcattc 600
tttcacctac ttctccttcg ggacgcaacg cgctacggga ccaattgggg attgtacaac 660
gcgacgccct tcatcaacta tcagtctaag ctcgtcgaac tgatcgaact ctacacggac 720
tactgcgtcc actggtacaa tcgtggcttt aacgagttgc gtcaacgcgg aacttctgct 780
acggcgtggc ttgagtttca cagataccgt cgtgagatga cgctaatggt cctcgacatc 840
gtggcgtcgt tcagctcgct tgacatcacc aactacccta tcgagaccga ctttcaactt 900
agccgtgtga tctacactga cccaatcggc ttcgtccatc gaagttcact ccgtggcgag 960
tcctggttct cgttcgtgaa ccgcgccaac ttcagtgacc ttgagaatgc gatccctaac 1020
ccacgcccta gctggttcct gaacaacatg attatctcta cagggagcct gaccttaccc 1080
gtcagtccca gcacagatcg cgcgagagtc tggtacggga gtcgggaccg gatctcgccc 1140
gccaactctc agttcattac tgagcttatc tccgggcagc acaccaccgc cacccagaca 1200
atactcggtc gcaacatctt ccgcgtggat tcacaggcgt gcaacctaaa cgacaccacg 1260
tacggcgtca accgcgccgt gttctaccat gacgcctcgg agggctcgca gcgtagcgtt 1320
tatgagggct acatcaggac gacgggtatc gacaacccga gagtgcagaa catcaacacc 1380
tatttgccag gcgagaacag cgacatcccg acgcccgaag actacaccca catcctcagc 1440
acaaccatca acctcacggg cgggctccgc caagttgcct cgaaccggcg gagcagcctc 1500
gttatgtacg gctggaccca caagtctctg gcgcgcaaca acaccatcaa tccagatcga 1560
atcacccaga taccactcac gaaggtggat acccgaggga ctggcgttag ttacgtcaac 1620
gatcctggat tcatcggcgg cgcgcttctc caacgcacgg accacgggtc gctgggcgtc 1680
cttcgggtac agtttccgct acacttgcgc cagcaatacc ggataagggt tcggtacgcc 1740
tcaacaacga acatcagact gtctgtcaac ggctccttcg gcaccatctc ccagaacctt 1800
ccctccacca tgcgcctcgg tgaggatctg cgctacggct ctttcgctat ccgcgagttt 1860
agcacttcaa tacgcccaac cgcgtcacct gaccagatac gcctgaccat tgaaccgtcc 1920
ttcatccggc aagaggtgta cgtggacaga atcgagttca taccagtcaa ctga 1974

<210> SEQ ID NO 10
<211> LENGTH: 657
<212> TYPE: PRT
<213> ORGANISM: Artificial
<220> FEATURE:
<223> OTHER INFORMATION: Amino acid sequence of TIC4064_4 wherein an additional alanine amino acid is inserted immediately following the initiating methionine and comprising a truncation of the protoxin domain and mutation at S95T.

<400> SEQUENCE: 10

Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

-continued

```
Ser Ile Val Tyr Asp Leu Ile Gly Lys Val Leu Gly Gly Ser Thr Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
```

```
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn
```

<210> SEQ ID NO 11
<211> LENGTH: 3474
<212> TYPE: DNA
<213> ORGANISM: Artificial
<220> FEATURE:
<223> OTHER INFORMATION: Plant synthetic coding sequence encoding a TIC4064_5 pesticidal protein designed for expression in a plant cell wherein an additional alanine codon is inserted immediately following the initiating methionine codon and a mutation at G88K.

<400> SEQUENCE: 11

```
atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180

gtgagcatcg ggacaaccat cgtttcgctt atcacagctc cctcgctgac gggcctcatc    240

tcaatcgttt atgacctcat taagaaggtg ctcggcggct cgtccggcca atccattagc    300

gacctttcca tctgcgatct gctctccata attgacctgc gggtgtcgca gtcggtcctg    360

aacgacggga tagcggactt caacggcagc gtcctcctgt accgcaacta cctggaggca    420

ctggactcct ggaacaagaa tcccaacagc gccagcgcgg aggagctgcg gacgcgcttt    480

cgcatcgctg attctgagtt tgaccgaatc ctgacacgcg gctcccttac caacggcggt    540

agcctggctc gccagaacgc ccagattctg ttgctgccca gtttcgcgtc agccgcattc    600

tttcacctac ttctccttcg ggacgcaacg cgctacggga ccaattgggg attgtacaac    660

gcgacgccct tcatcaacta tcagtctaag ctcgtcgaac tgatcgaact ctacacggac    720

tactgcgtcc actggtacaa tcgtggcttt aacgagttgc gtcaacgcgg aacttctgct    780

acggcgtggc ttgagtttca cagataccgt cgtgagatga cgctaatggt cctcgacatc    840

gtggcgtcgt tcagctcgct tgacatcacc aactacccta tcgagaccga ctttcaactt    900

agccgtgtga tctacactga cccaatcggc ttcgtccatc gaagttcact ccgtggcgag    960

tcctggttct cgttcgtgaa ccgcgccaac ttcagtgacc ttgagaatgc gatccctaac   1020

ccacgcccta gctggttcct gaacaacatg attatctcta cagggagcct gaccttaccc   1080
```

```
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg gcgcgcaaca acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggatctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagg aagaccttga ggctaccaag aaggcggtgg cgagcctgtt tacccgcact   2040
cgtgacggcc tccaagtaaa tgtcacggac taccaagtgg accaggcggc caacctcgta   2100
agctgcctat cagacgagca gtacgcccac gacaagaaga tgcttctgga agccgtcaga   2160
gccgccaaac ggctatcgcg cgagcgcaac ctgctccaag atcccgactt caacactatc   2220
aacagcaccg aggagaatgg ctggaaagcc agcaacggcg tgacgattag cgagggcggc   2280
ccgttctaca agggccgcgc actacagctt gcctccgcaa gggagaacta ccctacctac   2340
atctaccaga aggtcgatgc gtcggaactt aaaccataca cacggtatcg tctcgacggg   2400
ttcgtcaaat ccagccaaga cctagagatc gacctcatcc accatcacaa agtacatctc   2460
gtcaagaatg cgcccgacaa tcttgtctct gacacttacc cggacgattc ctgttcgggt   2520
attaacagat gccaggagca gcagatggtg aacgcccaac tcgaaaccga gcaccatcac   2580
ccaatggact gctgcggtgc ggctcagacc cacgagttta gcagttacat cgacaccggc   2640
gacctgaact cgacggtgga ccagggcatc tgggcgatct tcaaggttcg taccaccgac   2700
ggctacgcga ctctcgggaa tctggaactg gtcgagatcg gcccgttgag cggcgagtcg   2760
ctggagcggg agcagaggga caacgcaaag tggtctgccg agctgggccg aaagcgagcg   2820
gagactgacc gcgtgtacca ggatgctaag caaagtatca accacctctt cgtggactat   2880
caagatcaac agctcaaccc tgagatcggg atggctgaca tcatggacgc gcagaacctg   2940
gtggcgtcga tctccgatgt gtactccgac gccgtgctcc aaatccctgg cattaactac   3000
gagatctaca cggagctgtc gaaccgcctc caacaagcga gctaccttta cacgagccgg   3060
aacgccgtac agaacggcga cttcaactcc gggctcgact catggaacgc cactgcgggc   3120
gctaccgtcc aacaagacgg caacacccac tttctcgtcc ttagccactg ggacgcccaa   3180
gtctcgcagc agtttcgcgt tcagccgaac tgcaagtatg tcctgcgcgt gaccgccgag   3240
aaggtgggcg gtggtgacgg ctacgtcacc ataagggatg gtgcccacca cacggagacc   3300
ttaacgttta acgcctgtga ttatgacatc aacggcacct atgtgacgga caatacctac   3360
ctcactaagg aagtcgtgtt ctattcccat accgagcaca tgtgggtcga ggtttcggag   3420
```

```
acggagggcg tattccacat cgacagtgtg gagttcatgg agacccagca gtga        3474


<210> SEQ ID NO 12
<211> LENGTH: 1157
<212> TYPE: PRT
<213> ORGANISM: Artificial
<220> FEATURE:
<223> OTHER INFORMATION: Amino acid sequence of TIC4064_5  wherein an
      additional alanine amino acid is inserted immediately following
      the initiating methionine and comprising a mutation at G88K.

<400> SEQUENCE: 12

Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350
```

```
Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765
```

```
Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                 1015                 1020

Gln Asn  Gly Asp Phe Asn Ser  Gly Leu Asp Ser Trp  Asn Ala Thr
    1025                 1030                 1035

Ala Gly  Ala Thr Val Gln Gln  Asp Gly Asn Thr His  Phe Leu Val
    1040                 1045                 1050

Leu Ser  His Trp Asp Ala Gln  Val Ser Gln Gln Phe  Arg Val Gln
    1055                 1060                 1065

Pro Asn  Cys Lys Tyr Val Leu  Arg Val Thr Ala Glu  Lys Val Gly
    1070                 1075                 1080

Gly Gly  Asp Gly Tyr Val Thr  Ile Arg Asp Gly Ala  His His Thr
    1085                 1090                 1095

Glu Thr  Leu Thr Phe Asn Ala  Cys Asp Tyr Asp Ile  Asn Gly Thr
    1100                 1105                 1110

Tyr Val  Thr Asp Asn Thr Tyr  Leu Thr Lys Glu Val  Val Phe Tyr
    1115                 1120                 1125

Ser His  Thr Glu His Met Trp  Val Glu Val Ser Glu  Thr Glu Gly
    1130                 1135                 1140

Val Phe  His Ile Asp Ser Val  Glu Phe Met Glu Thr  Gln Gln
    1145                 1150                 1155
```

<210> SEQ ID NO 13
<211> LENGTH: 1974
<212> TYPE: DNA

<213> ORGANISM: Artificial
<220> FEATURE:
<223> OTHER INFORMATION: Plant synthetic coding sequence encoding a TIC4064_6 pesticidal protein with an additional alanine codon inserted immediately following the initiating methionine and comprising a protoxin truncation and G88K mutation.

<400> SEQUENCE: 13

```
atggctaacc agaacaagca cggcatcatt ggcgcatcca actgcgggtg taccagtgac     60
aacgtggcga aatacccgct cgccaataac ccatactcat cagccctgaa cctcaacagt    120
tgtcagaaca gctccatcct gaattggatc aacatcatcg gcgacgcggc gaaggaggcg    180
gtgagcatcg ggacaaccat cgtttcgctt atcacagctc cctcgctgac gggcctcatc    240
tcaatcgttt atgacctcat taagaaggtg ctcggcggct cgtccggcca atccattagc    300
gacctttcca tctgcgatct gctctccata attgacctgc gggtgtcgca gtcggtcctg    360
aacgacggga tagcggactt caacggcagc gtcctcctgt accgcaacta cctggaggca    420
ctggactcct ggaacaagaa tcccaacagc gccagcgcgg aggagctgcg gacgcgcttt    480
cgcatcgctg attctgagtt tgaccgaatc ctgacacgcg gctcccttac caacggcggt    540
agcctggctc gccagaacgc ccagattctg ttgctgccca gtttcgcgtc agccgcattc    600
tttcacctac ttctccttcg ggacgcaacg cgctacggga ccaattgggg attgtacaac    660
gcgacgccct tcatcaacta tcagtctaag ctcgtcgaac tgatcgaact ctacacggac    720
tactgcgtcc actggtacaa tcgtggcttt aacgagttgc gtcaacgcgg aacttctgct    780
acggcgtggc ttgagtttca cagataccgt cgtgagatga cgctaatggt cctcgacatc    840
gtggcgtcgt tcagctcgct tgacatcacc aactacccta tcgagaccga ctttcaactt    900
agccgtgtga tctacactga cccaatcggc ttcgtccatc gaagttcact ccgtggcgag    960
tcctggttct cgttcgtgaa ccgcgccaac ttcagtgacc ttgagaatgc gatccctaac   1020
ccacgcccta gctggttcct gaacaacatg attatctcta cagggagcct gaccttaccc   1080
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg gcgcgcaaca acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggatctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa ctga         1974
```

<210> SEQ ID NO 14
<211> LENGTH: 657
<212> TYPE: PRT

<213> ORGANISM: Artificial
<220> FEATURE:
<223> OTHER INFORMATION: Amino acid sequence of TIC4064_4 wherein an additional alanine amino acid is inserted immediately following the initiating methionine, and comprising a protoxin domain truncation and a G88K mutation.

<400> SEQUENCE: 14

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
```

```
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn
```

<210> SEQ ID NO 15
<211> LENGTH: 3474
<212> TYPE: DNA
<213> ORGANISM: Artificial
<220> FEATURE:
<223> OTHER INFORMATION: Plant synthetic coding sequence encoding a TIC4064_12_1 pesticidal protein designed for expression in a plant cell wherein an additional alanine codon is inserted and comprising mutations at D85A, S95T, A511H, N513D, and R605N.

<400> SEQUENCE: 15

```
atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180

gtgagcatcg ggacaaccat cgtttcgctt atcacagctc cctcgctgac gggcctcatc    240

tcaatcgttt atgcactcat tgggaaggtg ctcggcggct cgaccggcca atccattagc    300

gacctttcca tctgcgatct gctctccata attgacctgc gggtgtcgca gtcggtcctg    360
```

-continued

```
aacgacggga tagcggactt caacggcagc gtcctcctgt accgcaacta cctggaggca    420
ctggactcct ggaacaagaa tcccaacagc gccagcgcgg aggagctgcg gacgcgcttt    480
cgcatcgctg attctgagtt tgaccgaatc ctgacacgcg gctcccttac caacggcggt    540
agcctggctc gccagaacgc ccagattctg ttgctgccca gtttcgcgtc agccgcattc    600
tttcacctac ttctccttcg ggacgcaacg cgctacggga ccaattgggg attgtacaac    660
gcgacgccct tcatcaacta tcagtctaag ctcgtcgaac tgatcgaact ctacacggac    720
tactgcgtcc actggtacaa tcgtggcttt aacgagttgc gtcaacgcgg aacttctgct    780
acggcgtggc ttgagtttca cagataccgt cgtgagatga cgctaatggt cctcgacatc    840
gtggcgtcgt tcagctcgct tgacatcacc aactacccta tcgagaccga ctttcaactt    900
agccgtgtga tctacactga cccaatcggc ttcgtccatc gaagttcact ccgtggcgag    960
tcctggttct cgttcgtgaa ccgcgccaac ttcagtgacc ttgagaatgc gatccctaac   1020
ccacgcccta gctggttcct gaacaacatg attatctcta cagggagcct gaccttaccc   1080
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cggctccgc caagttgcct cgaaccggcg gagcagcctc   1500
gttatgtacg gctggaccca caagtctctg catcgcgata acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggctctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagg aagaccttga ggctaccaag aaggcggtgg cgagcctgtt tacccgcact   2040
cgtgacggcc tccaagtaaa tgtcacggac taccaagtgg accaggcggc caacctcgta   2100
agctgcctat cagacgagca gtacgcccac gacaagaaga tgcttctgga agccgtcaga   2160
gccgccaaac ggctatcgcg cgagcgcaac ctgctccaag atcccgactt caacactatc   2220
aacagcaccg aggagaatgg ctggaaagcc agcaacggcg tgacgattag cgagggcggc   2280
ccgttctaca agggccgcgc actacagctt gcctccgcaa gggagaacta ccctacctac   2340
atctaccaga aggtcgatgc gtcggaactt aaaccataca cacggtatcg tctcgacggg   2400
ttcgtcaaat ccagccaaga cctagagatc gacctcatcc accatcacaa agtacatctc   2460
gtcaagaatg cgcccgacaa tcttgtctct gacacttacc cggacgattc ctgttcgggt   2520
attaacagat gccaggagca gcagatggtg aacgcccaac tcgaaaccga gcaccatcac   2580
ccaatggact gctgcggtgc ggctcagacc cacgagttta gcagttacat cgacaccggc   2640
gacctgaact cgacggtgga ccagggcatc tgggcgatct tcaaggttcg taccaccgac   2700
```

ggctacgcga ctctcgggaa tctggaactg gtcgagatcg gcccgttgag cggcgagtcg 2760
ctggagcggg agcagaggga caacgcaaag tggtctgccg agctgggccg aaagcgagcg 2820
gagactgacc gcgtgtacca ggatgctaag caaagtatca accacctctt cgtggactat 2880
caagatcaac agctcaaccc tgagatcggg atggctgaca tcatggacgc gcagaacctg 2940
gtggcgtcga tctccgatgt gtactccgac gccgtgctcc aaatccctgg cattaactac 3000
gagatctaca cggagctgtc gaaccgcctc caacaagcga gctaccttta cacgagccgg 3060
aacgccgtac agaacggcga cttcaactcc gggctcgact catggaacgc cactgcgggc 3120
gctaccgtcc aacaagacgg caacacccac tttctcgtcc ttagccactg ggacgcccaa 3180
gtctcgcagc agtttcgcgt tcagccgaac tgcaagtatg tcctgcgcgt gaccgccgag 3240
aaggtgggcg gtggtgacgg ctacgtcacc ataagggatg gtgcccacca cacggagacc 3300
ttaacgttta acgcctgtga ttatgacatc aacggcacct atgtgacgga caatacctac 3360
ctcactaagg aagtcgtgtt ctattcccat accgagcaca tgtgggtcga ggtttcggag 3420
acggagggcg tattccacat cgacagtgtg gagttcatgg agacccagca gtga 3474

<210> SEQ ID NO 16
<211> LENGTH: 1157
<212> TYPE: PRT
<213> ORGANISM: Artificial
<220> FEATURE:
<223> OTHER INFORMATION: Amino acid sequence of TIC4064_12_1 with an additional alanine amino acid inserted immediately following the initiating methionine and comprising mutations at D85A, S95T, A511H, N513D, and R605N.

<400> SEQUENCE: 16

Met Ala Asn Gln Asn Lys His Gly Ile Ile Gly Ala Ser Asn Cys Gly
1 5 10 15

Cys Thr Ser Asp Asn Val Ala Lys Tyr Pro Leu Ala Asn Asn Pro Tyr
20 25 30

Ser Ser Ala Leu Asn Leu Asn Ser Cys Gln Asn Ser Ser Ile Leu Asn
35 40 45

Trp Ile Asn Ile Ile Gly Asp Ala Ala Lys Glu Ala Val Ser Ile Gly
50 55 60

Thr Thr Ile Val Ser Leu Ile Thr Ala Pro Ser Leu Thr Gly Leu Ile
65 70 75 80

Ser Ile Val Tyr Ala Leu Ile Gly Lys Val Leu Gly Gly Ser Thr Gly
85 90 95

Gln Ser Ile Ser Asp Leu Ser Ile Cys Asp Leu Leu Ser Ile Ile Asp
100 105 110

Leu Arg Val Ser Gln Ser Val Leu Asn Asp Gly Ile Ala Asp Phe Asn
115 120 125

Gly Ser Val Leu Leu Tyr Arg Asn Tyr Leu Glu Ala Leu Asp Ser Trp
130 135 140

Asn Lys Asn Pro Asn Ser Ala Ser Ala Glu Glu Leu Arg Thr Arg Phe
145 150 155 160

Arg Ile Ala Asp Ser Glu Phe Asp Arg Ile Leu Thr Arg Gly Ser Leu
165 170 175

Thr Asn Gly Gly Ser Leu Ala Arg Gln Asn Ala Gln Ile Leu Leu Leu
180 185 190

Pro Ser Phe Ala Ser Ala Ala Phe Phe His Leu Leu Leu Leu Arg Asp
195 200 205

Ala Thr Arg Tyr Gly Thr Asn Trp Gly Leu Tyr Asn Ala Thr Pro Phe

```
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu His Arg
            500                 505                 510

Asp Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Ala Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640
```

```
Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                 1005

Arg Leu  Gln Gln Ala Ser Tyr  Leu Tyr Thr Ser Arg  Asn Ala Val
    1010                 1015                 1020

Gln Asn  Gly Asp Phe Asn Ser  Gly Leu Asp Ser Trp  Asn Ala Thr
    1025                 1030                 1035

Ala Gly  Ala Thr Val Gln Gln  Asp Gly Asn Thr His  Phe Leu Val
    1040                 1045                 1050
```

-continued

```
Leu Ser  His Trp Asp Ala Gln  Val Ser Gln Gln Phe  Arg Val Gln
    1055                 1060                 1065

Pro Asn  Cys Lys Tyr Val Leu  Arg Val Thr Ala Glu  Lys Val Gly
    1070                 1075                 1080

Gly Gly  Asp Gly Tyr Val Thr  Ile Arg Asp Gly Ala  His His Thr
    1085                 1090                 1095

Glu Thr  Leu Thr Phe Asn Ala  Cys Asp Tyr Asp Ile  Asn Gly Thr
    1100                 1105                 1110

Tyr Val  Thr Asp Asn Thr Tyr  Leu Thr Lys Glu Val  Val Phe Tyr
    1115                 1120                 1125

Ser His  Thr Glu His Met Trp  Val Glu Val Ser Glu  Thr Glu Gly
    1130                 1135                 1140

Val Phe  His Ile Asp Ser Val  Glu Phe Met Glu Thr  Gln Gln
    1145                 1150                 1155
```

<210> SEQ ID NO 17
<211> LENGTH: 3474
<212> TYPE: DNA
<213> ORGANISM: Artificial
<220> FEATURE:
<223> OTHER INFORMATION: Plant synthetic coding sequence encoding a TIC4064_12_2 pesticidal protein designed for expression in a plant cell with an additional alanine codon inserted immediately following the initiating methionine and comprising mutations at D85A and S95T.

<400> SEQUENCE: 17

```
atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180

gtgagcatcg ggacaaccat cgtttcgctt atcacagctc cctcgctgac gggcctcatc    240

tcaatcgttt atgcactcat tgggaaggtg ctcggcggct cgaccggcca atccattagc    300

gacctttcca tctgcgatct gctctccata attgacctgc gggtgtcgca gtcggtcctg    360

aacgacggga tagcggactt caacggcagc gtcctcctgt accgcaacta cctggaggca    420

ctggactcct ggaacaagaa tcccaacagc gccagcgcgg aggagctgcg gacgcgcttt    480

cgcatcgctg attctgagtt tgaccgaatc ctgacacgcg gctcccttac caacggcggt    540

agcctggctc gccagaacgc ccagattctg ttgctgccca gtttcgcgtc agccgcattc    600

tttcacctac ttctccttcg ggacgcaacg cgctacggga ccaattgggg attgtacaac    660

gcgacgccct tcatcaacta tcagtctaag ctcgtcgaac tgatcgaact ctacacggac    720

tactgcgtcc actggtacaa tcgtggcttt aacgagttgc gtcaacgcgg aacttctgct    780

acggcgtggc ttgagtttca cagataccgt cgtgagatga cgctaatggt cctcgacatc    840

gtggcgtcgt tcagctcgct tgacatcacc aactacccta tcgagaccga ctttcaactt    900

agccgtgtga tctacactga cccaatcggc ttcgtccatc gaagttcact ccgtggcgag    960

tcctggttct cgttcgtgaa ccgcgccaac ttcagtgacc ttgagaatgc gatccctaac   1020

ccacgcccta gctggttcct gaacaacatg attatctcta cagggagcct gaccttaccc   1080

gtcagtccca gcacagatcg cgcgagagtc tggtacggga gtcgggaccg gatctcgccc   1140

gccaactctc agttcattac tgagcttatc tccgggcagc acaccaccgc cacccagaca   1200

atactcggtc gcaacatctt ccgcgtggat tcacaggcgt gcaacctaaa cgacaccacg   1260

tacggcgtca accgcgccgt gttctaccat gacgcctcgg agggctcgca gcgtagcgtt   1320
```

-continued

```
tatgagggct acatcaggac gacgggtatc gacaacccga gagtgcagaa catcaacacc   1380

tatttgccag gcgagaacag cgacatcccg acgcccgaag actacaccca catcctcagc   1440

acaaccatca acctcacggg cgggctccgc caagttgcct cgaaccggcg gagcagcctc   1500

gttatgtacg gctggaccca caagtctctg gcgcgcaaca acaccatcaa tccagatcga   1560

atcacccaga taccactcac gaaggtggat acccgaggga ctggcgttag ttacgtcaac   1620

gatcctggat tcatcggcgg cgcgcttctc caacgcacgg accacgggtc gctgggcgtc   1680

cttcgggtac agtttccgct acacttgcgc cagcaatacc ggataagggt tcggtacgcc   1740

tcaacaacga acatcagact gtctgtcaac ggctccttcg gcaccatctc ccagaacctt   1800

ccctccacca tgcgcctcgg tgaggatctg cgctacggct ctttcgctat ccgcgagttt   1860

agcacttcaa tacgcccaac cgcgtcacct gaccagatac gcctgaccat tgaaccgtcc   1920

ttcatccggc aagaggtgta cgtggacaga atcgagttca taccagtcaa cccgacgcgg   1980

gaggcgaagg aagaccttga ggctaccaag aaggcggtgg cgagcctgtt tacccgcact   2040

cgtgacggcc tccaagtaaa tgtcacggac taccaagtgg accaggcggc caacctcgta   2100

agctgcctat cagacgagca gtacgcccac gacaagaaga tgcttctgga agccgtcaga   2160

gccgccaaac ggctatcgcg cgagcgcaac ctgctccaag atcccgactt caacactatc   2220

aacagcaccg aggagaatgg ctggaaagcc agcaacggcg tgacgattag cgagggcggc   2280

ccgttctaca agggccgcgc actacagctt gcctccgcaa gggagaacta ccctacctac   2340

atctaccaga aggtcgatgc gtcggaactt aaaccataca cacggtatcg tctcgacggg   2400

ttcgtcaaat ccagccaaga cctagagatc gacctcatcc accatcacaa agtacatctc   2460

gtcaagaatg cgcccgacaa tcttgtctct gacacttacc cggacgattc ctgttcgggt   2520

attaacagat gccaggagca gcagatggtg aacgcccaac tcgaaaccga gcaccatcac   2580

ccaatggact gctgcggtgc ggctcagacc cacgagttta gcagttacat cgacaccggc   2640

gacctgaact cgacggtgga ccagggcatc tgggcgatct tcaaggttcg taccaccgac   2700

ggctacgcga ctctcgggaa tctggaactg gtcgagatcg gcccgttgag cggcgagtcg   2760

ctggagcggg agcagaggga caacgcaaag tggtctgccg agctgggccg aaagcgagcg   2820

gagactgacc gcgtgtacca ggatgctaag caaagtatca accacctctt cgtggactat   2880

caagatcaac agctcaaccc tgagatcggg atggctgaca tcatggacgc gcagaacctg   2940

gtggcgtcga tctccgatgt gtactccgac gccgtgctcc aaatccctgg cattaactac   3000

gagatctaca cggagctgtc gaaccgcctc caacaagcga gctaccttta cacgagccgg   3060

aacgccgtac agaacggcga cttcaactcc gggctcgact catggaacgc cactgcgggc   3120

gctaccgtcc aacaagacgg caacacccac tttctcgtcc ttagccactg ggacgcccaa   3180

gtctcgcagc agtttcgcgt tcagccgaac tgcaagtatg tcctgcgcgt gaccgccgag   3240

aaggtgggcg gtggtgacgg ctacgtcacc ataagggatg gtgcccacca cacggagacc   3300

ttaacgttta acgcctgtga ttatgacatc aacggcacct atgtgacgga caatacctac   3360

ctcactaagg aagtcgtgtt ctattcccat accgagcaca tgtgggtcga ggtttcggag   3420

acggagggcg tattccacat cgacagtgtg gagttcatgg agacccagca gtga         3474
```

<210> SEQ ID NO 18
<211> LENGTH: 1157
<212> TYPE: PRT
<213> ORGANISM: Artificial
<220> FEATURE:
<223> OTHER INFORMATION: Amino acid sequence of TIC4064_12_2 wherein an additional alanine amino acid is inserted immediately following the initiating methionine and comprising mutations at D85A and S95T.

<400> SEQUENCE: 18

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Ala Leu Ile Gly Lys Val Leu Gly Gly Ser Thr Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
```

```
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815
```

```
Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                1015                1020

Gln Asn  Gly Asp Phe Asn Ser  Gly Leu Asp Ser Trp  Asn Ala Thr
    1025                1030                1035

Ala Gly  Ala Thr Val Gln Gln  Asp Gly Asn Thr His  Phe Leu Val
    1040                1045                1050

Leu Ser  His Trp Asp Ala Gln  Val Ser Gln Gln Phe  Arg Val Gln
    1055                1060                1065

Pro Asn  Cys Lys Tyr Val Leu  Arg Val Thr Ala Glu  Lys Val Gly
    1070                1075                1080

Gly Gly  Asp Gly Tyr Val Thr  Ile Arg Asp Gly Ala  His His Thr
    1085                1090                1095

Glu Thr  Leu Thr Phe Asn Ala  Cys Asp Tyr Asp Ile  Asn Gly Thr
    1100                1105                1110

Tyr Val  Thr Asp Asn Thr Tyr  Leu Thr Lys Glu Val  Val Phe Tyr
    1115                1120                1125

Ser His  Thr Glu His Met Trp  Val Glu Val Ser Glu  Thr Glu Gly
    1130                1135                1140

Val Phe  His Ile Asp Ser Val  Glu Phe Met Glu Thr  Gln Gln
    1145                1150                1155
```

<210> SEQ ID NO 19
<211> LENGTH: 1992
<212> TYPE: DNA
<213> ORGANISM: Artificial
<220> FEATURE:
<223> OTHER INFORMATION: Plant synthetic coding sequence encoding a TIC4064_13 with an additional alanine codon inserted immediately following the initiating methionine, comprising mutations at D85A, S95T, A511H, N513D, and R605N and protoxin truncation.

<400> SEQUENCE: 19

```
atggctaacc agaacaagca cggcatcatt ggcgcatcca actgcgggtg taccagtgac     60
aacgtggcga aatacccgct cgccaataac ccatactcat cagccctgaa cctcaacagt    120
tgtcagaaca gctccatcct gaattggatc aacatcatcg gcgacgcggc gaaggaggcg    180
gtgagcatcg ggacaaccat cgtttcgctt atcacagctc cctcgctgac gggcctcatc    240
tcaatcgttt atgcactcat tgggaaggtg ctcggcggct cgaccggcca atccattagc    300
gacctttcca tctgcgatct gctctccata attgacctgc gggtgtcgca gtcggtcctg    360
aacgacggga tagcggactt caacggcagc gtcctcctgt accgcaacta cctggaggca    420
ctggactcct ggaacaagaa tcccaacagc gccagcgcgg aggagctgcg gacgcgcttt    480
cgcatcgctg attctgagtt tgaccgaatc ctgacacgcg gctcccttac caacggcggt    540
agcctggctc gccagaacgc ccagattctg ttgctgccca gtttcgcgtc agccgcattc    600
tttcacctac ttctccttcg ggacgcaacg cgctacggga ccaattgggg attgtacaac    660
gcgacgccct tcatcaacta tcagtctaag ctcgtcgaac tgatcgaact ctacacggac    720
tactgcgtcc actggtacaa tcgtggcttt aacgagttgc gtcaacgcgg aacttctgct    780
acggcgtggc ttgagtttca cagataccgt cgtgagatga cgctaatggt cctcgacatc    840
gtggcgtcgt tcagctcgct tgacatcacc aactacccta tcgagaccga ctttcaactt    900
agccgtgtga tctacactga cccaatcggc ttcgtccatc gaagttcact ccgtggcgag    960
tcctggttct cgttcgtgaa ccgcgccaac ttcagtgacc ttgagaatgc gatccctaac   1020
ccacgcccta gctggttcct gaacaacatg attatctcta cagggagcct gaccttaccc   1080
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg catcgcgata acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggctctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagt ga                                                       1992
```

<210> SEQ ID NO 20
<211> LENGTH: 663
<212> TYPE: PRT
<213> ORGANISM: Artificial
<220> FEATURE:
<223> OTHER INFORMATION: Amino acid sequence of TIC4064_13 with an additional alanine amino acid inserted immediately following the initiating methionine, and comprising mutations at D85A, S95T, A511H, N513D, and R605N and truncation of the protoxin domain.

<400> SEQUENCE: 20

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Ala Leu Ile Gly Lys Val Leu Gly Gly Ser Thr Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
```

-continued

```
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu His Arg
            500                 505                 510

Asp Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Ala Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys
            660
```

<210> SEQ ID NO 21
<211> LENGTH: 3474
<212> TYPE: DNA
<213> ORGANISM: Artificial
<220> FEATURE:
<223> OTHER INFORMATION: Plant synthetic coding sequence encoding a TIC4064_14 pesticidal protein with an additional alanine codon inserted immediately following the initiating methionine and comprising mutations at S95T, R169K, and S332A.

<400> SEQUENCE: 21

```
atggctaacc agaacaagca cggcatcatt ggcgcatcca actgcgggtg taccagtgac      60

aacgtggcga aatacccgct cgccaataac ccatactcat cagccctgaa cctcaacagt     120

tgtcagaaca gctccatcct gaattggatc aacatcatcg gcgacgcggc gaaggaggcg     180

gtgagcatcg ggacaaccat cgtttcgctt atcacagctc cctcgctgac gggcctcatc     240

tcaatcgttt atgacctcat tgggaaggtg ctcggcggct cgaccggcca atccattagc     300

gacctttcca tctgcgatct gctctccata attgacctgc gggtgtcgca gtcggtcctg     360

aacgacggga tagcggactt caacggcagc gtcctcctgt accgcaacta cctggaggca     420

ctggactcct ggaacaagaa tcccaacagc gccagcgcgg aggagctgcg gacgcgcttt     480
```

-continued

```
cgcatcgctg attctgagtt tgacaagatc ctgacacgcg gctcccttac caacggcggt    540
agcctggctc gccagaacgc ccagattctg ttgctgccca gtttcgcgtc agccgcattc    600
tttcacctac ttctccttcg ggacgcaacg cgctacggga ccaattgggg attgtacaac    660
gcgacgccct tcatcaacta tcagtctaag ctcgtcgaac tgatcgaact ctacacggac    720
tactgcgtcc actggtacaa tcgtggcttt aacgagttgc gtcaacgcgg aacttctgct    780
acggcgtggc ttgagtttca cagataccgt cgtgagatga cgctaatggt cctcgacatc    840
gtggcgtcgt tcagctcgct tgacatcacc aactacccta tcgagaccga ctttcaactt    900
agccgtgtga tctacactga cccaatcggc ttcgtccatc gaagttcact ccgtggcgag    960
tcctggttct cgttcgtgaa ccgcgccaac ttcgctgacc ttgagaatgc gatccctaac   1020
ccacgcccta gctggttcct gaacaacatg attatctcta cagggagcct gaccttaccc   1080
gtcagtccca gcacagatcg cgcgagagtc tggtacggga gtcgggaccg gatctcgccc   1140
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg gcgcgcaaca acaccatcaa tccagatcga   1560
atcacccaga taccactcac gaaggtggat acccgaggga ctggcgttag ttacgtcaac   1620
gatcctggat tcatcggcgg cgcgcttctc caacgcacgg accacgggtc gctgggcgtc   1680
cttcgggtac agtttccgct acacttgcgc cagcaatacc ggataagggt tcggtacgcc   1740
tcaacaacga acatcagact gtctgtcaac ggctccttcg gcaccatctc ccagaacctt   1800
ccctccacca tgcgcctcgg tgaggatctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagg aagaccttga ggctaccaag aaggcggtgg cgagcctgtt tacccgcact   2040
cgtgacggcc tccaagtaaa tgtcacggac taccaagtgg accaggcggc caacctcgta   2100
agctgcctat cagacgagca gtacgcccac gacaagaaga tgcttctgga agccgtcaga   2160
gccgccaaac ggctatcgcg cgagcgcaac ctgctccaag atcccgactt caacactatc   2220
aacagcaccg aggagaatgg ctggaaagcc agcaacggcg tgacgattag cgagggcggc   2280
ccgttctaca agggccgcgc actacagctt gcctccgcaa gggagaacta ccctacctac   2340
atctaccaga aggtcgatgc gtcggaactt aaaccataca cacggtatcg tctcgacggg   2400
ttcgtcaaat ccagccaaga cctagagatc gacctcatcc accatcacaa agtacatctc   2460
gtcaagaatg cgcccgacaa tcttgtctct gacacttacc cggacgattc ctgttcgggt   2520
attaacagat gccaggagca gcagatggtg aacgcccaac tcgaaaccga gcaccatcac   2580
ccaatggact gctgcggtgc ggctcagacc cacgagttta gcagttacat cgacaccggc   2640
gacctgaact cgacggtgga ccagggcatc tgggcgatct tcaaggttcg taccaccgac   2700
ggctacgcga ctctcgggaa tctggaactg gtcgagatcg gcccgttgag cggcgagtcg   2760
ctggagcggg agcagaggga caacgcaaag tggtctgccg agctgggccg aaagcgagcg   2820
gagactgacc gcgtgtacca ggatgctaag caaagtatca accacctctt cgtggactat   2880
```

```
caagatcaac agctcaaccc tgagatcggg atggctgaca tcatggacgc gcagaacctg   2940

gtggcgtcga tctccgatgt gtactccgac gccgtgctcc aaatccctgg cattaactac   3000

gagatctaca cggagctgtc gaaccgcctc caacaagcga gctaccttta cacgagccgg   3060

aacgccgtac agaacggcga cttcaactcc gggctcgact catggaacgc cactgcgggc   3120

gctaccgtcc aacaagacgg caacacccac tttctcgtcc ttagccactg ggacgcccaa   3180

gtctcgcagc agtttcgcgt tcagccgaac tgcaagtatg tcctgcgcgt gaccgccgag   3240

aaggtgggcg gtggtgacgg ctacgtcacc ataagggatg gtgcccacca cacggagacc   3300

ttaacgttta acgcctgtga ttatgacatc aacggcacct atgtgacgga caatacctac   3360

ctcactaagg aagtcgtgtt ctattcccat accgagcaca tgtgggtcga ggtttcggag   3420

acggagggcg tattccacat cgacagtgtg gagttcatgg agacccagca gtga         3474
```

```
<210> SEQ ID NO 22
<211> LENGTH: 1157
<212> TYPE: PRT
<213> ORGANISM: Artificial
<220> FEATURE:
<223> OTHER INFORMATION: Amino acid sequence of TIC4064_14 with an
      additional alanine amino acid inserted immediately following the
      initiating methionine and comprising mutations at S95T, R169K, and
      S332A.

<400> SEQUENCE: 22

Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Gly Lys Val Leu Gly Gly Ser Thr Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Lys Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240
```

-continued

```
Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ala Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
```

```
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                1015                1020

Gln Asn  Gly Asp Phe Asn Ser  Gly Leu Asp Ser Trp  Asn Ala Thr
    1025                1030                1035

Ala Gly  Ala Thr Val Gln Gln  Asp Gly Asn Thr His  Phe Leu Val
    1040                1045                1050

Leu Ser  His Trp Asp Ala Gln  Val Ser Gln Gln Phe  Arg Val Gln
    1055                1060                1065

Pro Asn  Cys Lys Tyr Val Leu  Arg Val Thr Ala Glu  Lys Val Gly
    1070                1075                1080
```

```
Gly Gly  Asp Gly Tyr Val Thr  Ile Arg Asp Gly Ala  His His Thr
    1085                 1090                 1095

Glu Thr  Leu Thr Phe Asn Ala  Cys Asp Tyr Asp Ile  Asn Gly Thr
    1100                 1105                 1110

Tyr Val  Thr Asp Asn Thr Tyr  Leu Thr Lys Glu Val  Val Phe Tyr
    1115                 1120                 1125

Ser His  Thr Glu His Met Trp  Val Glu Val Ser Glu  Thr Glu Gly
    1130                 1135                 1140

Val Phe  His Ile Asp Ser Val  Glu Phe Met Glu Thr  Gln Gln
    1145                 1150                 1155
```

<210> SEQ ID NO 23
<211> LENGTH: 1992
<212> TYPE: DNA
<213> ORGANISM: Artificial
<220> FEATURE:
<223> OTHER INFORMATION: Plant synthetic coding sequence encoding a TIC4064_15 pesticidal protein with an additional alanine codon inserted immediately following the initiating methionine and comprising a truncation of the protoxin domain and mutations at S95T, R169K, and S332A.

<400> SEQUENCE: 23

```
atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180

gtgagcatcg ggacaaccat cgtttcgctt atcacagctc cctcgctgac gggcctcatc    240

tcaatcgttt atgacctcat tgggaaggtg ctcggcggct cgaccggcca atccattagc    300

gacctttcca tctgcgatct gctctccata attgacctgc gggtgtcgca gtcggtcctg    360

aacgacggga tagcggactt caacggcagc gtcctcctgt accgcaacta cctggaggca    420

ctggactcct ggaacaagaa tcccaacagc gccagcgcgg aggagctgcg gacgcgcttt    480

cgcatcgctg attctgagtt tgacaagatc ctgacacgcg gctcccttac caacggcggt    540

agcctggctc gccagaacgc ccagattctg ttgctgccca gtttcgcgtc agccgcattc    600

tttcacctac ttctccttcg ggacgcaacg cgctacggga ccaattgggg attgtacaac    660

gcgacgccct tcatcaacta tcagtctaag ctcgtcgaac tgatcgaact ctacacggac    720

tactgcgtcc actggtacaa tcgtggcttt aacgagttgc gtcaacgcgg aacttctgct    780

acggcgtggc ttgagtttca cagataccgt cgtgagatga cgctaatggt cctcgacatc    840

gtggcgtcgt tcagctcgct tgacatcacc aactacccta tcgagaccga ctttcaactt    900

agccgtgtga tctacactga cccaatcggc ttcgtccatc gaagttcact ccgtggcgag    960

tcctggttct cgttcgtgaa ccgcgccaac ttcgctgacc ttgagaatgc gatccctaac   1020

ccacgcccta gctggttcct gaacaacatg attatctcta cagggagcct gaccttaccc   1080

gtcagtccca gcacagatcg cgcgagagtc tggtacggga gtcgggaccg gatctcgccc   1140

gccaactctc agttcattac tgagcttatc tccgggcagc acaccaccgc cacccagaca   1200

atactcggtc gcaacatctt ccgcgtggat tcacaggcgt gcaacctaaa cgacaccacg   1260

tacggcgtca accgcgccgt gttctaccat gacgcctcgg agggctcgca gcgtagcgtt   1320

tatgagggct acatcaggac gacgggtatc gacaacccga gagtgcagaa catcaacacc   1380

tatttgccag gcgagaacag cgacatcccg acgcccgaag actacaccca catcctcagc   1440

acaaccatca acctcacggg cgggctccgc caagttgcct cgaaccggcg gagcagcctc   1500
```

gttatgtacg gctggaccca caagtctctg gcgcgcaaca acaccatcaa tccagatcga 1560
atcacccaga taccactcac gaaggtggat acccgaggga ctggcgttag ttacgtcaac 1620
gatcctggat tcatcggcgg cgcgcttctc caacgcacgg accacgggtc gctgggcgtc 1680
cttcgggtac agtttccgct acacttgcgc cagcaatacc ggataagggt tcggtacgcc 1740
tcaacaacga acatcagact gtctgtcaac ggctccttcg gcaccatctc ccagaacctt 1800
ccctccacca tgcgcctcgg tgaggatctg cgctacggct ctttcgctat ccgcgagttt 1860
agcacttcaa tacgcccaac cgcgtcacct gaccagatac gcctgaccat tgaaccgtcc 1920
ttcatccggc aagaggtgta cgtggacaga atcgagttca taccagtcaa cccgacgcgg 1980
gaggcgaagt ga 1992

<210> SEQ ID NO 24
<211> LENGTH: 663
<212> TYPE: PRT
<213> ORGANISM: Artificial
<220> FEATURE:
<223> OTHER INFORMATION: Amino acid sequence of TIC4064_15 with an additional alanine amino acid inserted immediately following the initiating methionine, and comprising a truncation at the protoxin domain and mutations at S95T, R169K, and S332A.

<400> SEQUENCE: 24

Met Ala Asn Gln Asn Lys His Gly Ile Ile Gly Ala Ser Asn Cys Gly
1 5 10 15

Cys Thr Ser Asp Asn Val Ala Lys Tyr Pro Leu Ala Asn Asn Pro Tyr
20 25 30

Ser Ser Ala Leu Asn Leu Asn Ser Cys Gln Asn Ser Ser Ile Leu Asn
35 40 45

Trp Ile Asn Ile Ile Gly Asp Ala Ala Lys Glu Ala Val Ser Ile Gly
50 55 60

Thr Thr Ile Val Ser Leu Ile Thr Ala Pro Ser Leu Thr Gly Leu Ile
65 70 75 80

Ser Ile Val Tyr Asp Leu Ile Gly Lys Val Leu Gly Gly Ser Thr Gly
85 90 95

Gln Ser Ile Ser Asp Leu Ser Ile Cys Asp Leu Leu Ser Ile Ile Asp
100 105 110

Leu Arg Val Ser Gln Ser Val Leu Asn Asp Gly Ile Ala Asp Phe Asn
115 120 125

Gly Ser Val Leu Leu Tyr Arg Asn Tyr Leu Glu Ala Leu Asp Ser Trp
130 135 140

Asn Lys Asn Pro Asn Ser Ala Ser Ala Glu Glu Leu Arg Thr Arg Phe
145 150 155 160

Arg Ile Ala Asp Ser Glu Phe Asp Lys Ile Leu Thr Arg Gly Ser Leu
165 170 175

Thr Asn Gly Gly Ser Leu Ala Arg Gln Asn Ala Gln Ile Leu Leu Leu
180 185 190

Pro Ser Phe Ala Ser Ala Ala Phe Phe His Leu Leu Leu Leu Arg Asp
195 200 205

Ala Thr Arg Tyr Gly Thr Asn Trp Gly Leu Tyr Asn Ala Thr Pro Phe
210 215 220

Ile Asn Tyr Gln Ser Lys Leu Val Glu Leu Ile Glu Leu Tyr Thr Asp
225 230 235 240

Tyr Cys Val His Trp Tyr Asn Arg Gly Phe Asn Glu Leu Arg Gln Arg
245 250 255

-continued

```
Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ala Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys
            660
```

<210> SEQ ID NO 25
<211> LENGTH: 3474
<212> TYPE: DNA
<213> ORGANISM: Artificial
<220> FEATURE:
<223> OTHER INFORMATION: Plant synthetic coding sequence encoding a TIC4064_16 pesticidal protein with an additional alanine codon inserted immediately following the initiating methionine and comprising mutations at S34G, G88K, I386S, G403Q, and R605N.

<400> SEQUENCE: 25
atggctaacc agaacaagca cggcatcatt ggcgcatcca actgcgggtg taccagtgac 60
aacgtggcga aatacccgct cgccaataac ccatactcag gagccctgaa cctcaacagt 120
tgtcagaaca gctccatcct gaattggatc aacatcatcg gcgacgcggc gaaggaggcg 180
gtgagcatcg ggacaaccat cgtttcgctt atcacagctc cctcgctgac gggcctcatc 240
tcaatcgttt atgacctcat taagaaggtg ctcggcggct cgtccggcca atccattagc 300
gacctttcca tctgcgatct gctctccata attgacctgc gggtgtcgca gtcggtcctg 360
aacgacggga tagcggactt caacggcagc gtcctcctgt accgcaacta cctggaggca 420
ctggactcct ggaacaagaa tcccaacagc gccagcgcgg aggagctgcg gacgcgcttt 480
cgcatcgctg attctgagtt tgaccgaatc ctgacacgcg gctcccttac caacggcggt 540
agcctggctc gccagaacgc ccagattctg ttgctgccca gtttcgcgtc agccgcattc 600
tttcacctac ttctccttcg ggacgcaacg cgctacggga ccaattgggg attgtacaac 660
gcgacgccct tcatcaacta tcagtctaag ctcgtcgaac tgatcgaact ctacacggac 720
tactgcgtcc actggtacaa tcgtggcttt aacgagttgc gtcaacgcgg aacttctgct 780
acggcgtggc ttgagtttca cagataccgt cgtgagatga cgctaatggt cctcgacatc 840
gtggcgtcgt tcagctcgct tgacatcacc aactacccta tcgagaccga ctttcaactt 900
agccgtgtga tctacactga cccaatcggc ttcgtccatc gaagttcact ccgtggcgag 960
tcctggttct cgttcgtgaa ccgcgccaac ttcagtgacc ttgagaatgc gatccctaac 1020
ccacgcccta gctggttcct gaacaacatg attatctcta cagggagcct gaccttaccc 1080
gtcagtccca gcacagatcg cgcgagagtc tggtacggga gtcgggaccg gatctcgccc 1140
gccaactctc agttcagtac tgagcttatc tccgggcagc acaccaccgc cacccagaca 1200
atactccagc gcaacatctt ccgcgtggat tcacaggcgt gcaacctaaa cgacaccacg 1260
tacggcgtca accgcgccgt gttctaccat gacgcctcgg agggctcgca gcgtagcgtt 1320
tatgagggct acatcaggac gacgggtatc gacaacccga gagtgcagaa catcaacacc 1380
tatttgccag gcgagaacag cgacatcccg acgcccgaag actacaccca catcctcagc 1440
acaaccatca acctcacggg cgggctccgc caagttgcct cgaaccggcg gagcagcctc 1500
gttatgtacg gctggaccca caagtctctg gcgcgcaaca acaccatcaa tccagatcga 1560
atcacccaga taccactcac gaaggtggat acccgaggga ctggcgttag ttacgtcaac 1620
gatcctggat tcatcggcgg cgcgcttctc caacgcacgg accacgggtc gctgggcgtc 1680
cttcgggtac agtttccgct acacttgcgc cagcaatacc ggataagggt tcggtacgcc 1740
tcaacaacga acatcagact gtctgtcaac ggctccttcg gcaccatctc ccagaacctt 1800
ccctccacca tgaacctcgg tgaggatctg cgctacggct ctttcgctat ccgcgagttt 1860
agcacttcaa tacgcccaac cgcgtcacct gaccagatac gcctgaccat tgaaccgtcc 1920
ttcatccggc aagaggtgta cgtggacaga atcgagttca taccagtcaa cccgacgcgg 1980

-continued

```
gaggcgaagg aagaccttga ggctaccaag aaggcggtgg cgagcctgtt tacccgcact   2040

cgtgacggcc tccaagtaaa tgtcacggac taccaagtgg accaggcggc caacctcgta   2100

agctgcctat cagacgagca gtacgcccac gacaagaaga tgcttctgga agccgtcaga   2160

gccgccaaac ggctatcgcg cgagcgcaac ctgctccaag atcccgactt caacactatc   2220

aacagcaccg aggagaatgg ctggaaagcc agcaacggcg tgacgattag cgagggcggc   2280

ccgttctaca agggccgcgc actacagctt gcctccgcaa gggagaacta ccctacctac   2340

atctaccaga aggtcgatgc gtcggaactt aaaccataca cacggtatcg tctcgacggg   2400

ttcgtcaaat ccagccaaga cctagagatc gacctcatcc accatcacaa agtacatctc   2460

gtcaagaatg cgcccgacaa tcttgtctct gacacttacc cggacgattc ctgttcgggt   2520

attaacagat gccaggagca gcagatggtg aacgcccaac tcgaaaccga gcaccatcac   2580

ccaatggact gctgcggtgc ggctcagacc cacgagttta gcagttacat cgacaccggc   2640

gacctgaact cgacggtgga ccagggcatc tgggcgatct tcaaggttcg taccaccgac   2700

ggctacgcga ctctcgggaa tctggaactg gtcgagatcg gcccgttgag cggcgagtcg   2760

ctggagcggg agcagaggga caacgcaaag tggtctgccg agctgggccg aaagcgagcg   2820

gagactgacc gcgtgtacca ggatgctaag caaagtatca accacctctt cgtggactat   2880

caagatcaac agctcaaccc tgagatcggg atggctgaca tcatggacgc gcagaacctg   2940

gtggcgtcga tctccgatgt gtactccgac gccgtgctcc aaatccctgg cattaactac   3000

gagatctaca cggagctgtc gaaccgcctc caacaagcga gctaccttta cacgagccgg   3060

aacgccgtac agaacggcga cttcaactcc gggctcgact catggaacgc cactgcgggc   3120

gctaccgtcc aacaagacgg caacacccac tttctcgtcc ttagccactg ggacgcccaa   3180

gtctcgcagc agtttcgcgt tcagccgaac tgcaagtatg tcctgcgcgt gaccgccgag   3240

aaggtgggcg gtggtgacgg ctacgtcacc ataagggatg gtgcccacca cacggagacc   3300

ttaacgttta acgcctgtga ttatgacatc aacggcacct atgtgacgga caatacctac   3360

ctcactaagg aagtcgtgtt ctattcccat accgagcaca tgtgggtcga ggtttcggag   3420

acggagggcg tattccacat cgacagtgtg gagttcatgg agacccagca gtga         3474
```

```
<210> SEQ ID NO 26
<211> LENGTH: 1157
<212> TYPE: PRT
<213> ORGANISM: Artificial
<220> FEATURE:
<223> OTHER INFORMATION: Amino acid sequence of TIC4064_16 with an
      additional alanine amino acid inserted immediately following the
      initiating methionine and comprising mutations at S34G, G88K,
      I386S, G403Q, and R605N.

<400> SEQUENCE: 26

Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Gly Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
```

-continued

```
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ser Thr Glu Leu Ile Ser Gly Gln His Thr Thr Ala Thr Gln Thr
385                 390                 395                 400

Ile Leu Gln Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510
```

Asn Asn Thr Ile Asn Pro Asp Arg Ile Thr Gln Ile Pro Leu Thr Lys
515 520 525

Val Asp Thr Arg Gly Thr Gly Val Ser Tyr Val Asn Asp Pro Gly Phe
530 535 540

Ile Gly Gly Ala Leu Leu Gln Arg Thr Asp His Gly Ser Leu Gly Val
545 550 555 560

Leu Arg Val Gln Phe Pro Leu His Leu Arg Gln Gln Tyr Arg Ile Arg
565 570 575

Val Arg Tyr Ala Ser Thr Thr Asn Ile Arg Leu Ser Val Asn Gly Ser
580 585 590

Phe Gly Thr Ile Ser Gln Asn Leu Pro Ser Thr Met Asn Leu Gly Glu
595 600 605

Asp Leu Arg Tyr Gly Ser Phe Ala Ile Arg Glu Phe Ser Thr Ser Ile
610 615 620

Arg Pro Thr Ala Ser Pro Asp Gln Ile Arg Leu Thr Ile Glu Pro Ser
625 630 635 640

Phe Ile Arg Gln Glu Val Tyr Val Asp Arg Ile Glu Phe Ile Pro Val
645 650 655

Asn Pro Thr Arg Glu Ala Lys Glu Asp Leu Glu Ala Thr Lys Lys Ala
660 665 670

Val Ala Ser Leu Phe Thr Arg Thr Arg Asp Gly Leu Gln Val Asn Val
675 680 685

Thr Asp Tyr Gln Val Asp Gln Ala Ala Asn Leu Val Ser Cys Leu Ser
690 695 700

Asp Glu Gln Tyr Ala His Asp Lys Lys Met Leu Leu Glu Ala Val Arg
705 710 715 720

Ala Ala Lys Arg Leu Ser Arg Glu Arg Asn Leu Leu Gln Asp Pro Asp
725 730 735

Phe Asn Thr Ile Asn Ser Thr Glu Glu Asn Gly Trp Lys Ala Ser Asn
740 745 750

Gly Val Thr Ile Ser Glu Gly Gly Pro Phe Tyr Lys Gly Arg Ala Leu
755 760 765

Gln Leu Ala Ser Ala Arg Glu Asn Tyr Pro Thr Tyr Ile Tyr Gln Lys
770 775 780

Val Asp Ala Ser Glu Leu Lys Pro Tyr Thr Arg Tyr Arg Leu Asp Gly
785 790 795 800

Phe Val Lys Ser Ser Gln Asp Leu Glu Ile Asp Leu Ile His His His
805 810 815

Lys Val His Leu Val Lys Asn Ala Pro Asp Asn Leu Val Ser Asp Thr
820 825 830

Tyr Pro Asp Asp Ser Cys Ser Gly Ile Asn Arg Cys Gln Glu Gln Gln
835 840 845

Met Val Asn Ala Gln Leu Glu Thr Glu His His His Pro Met Asp Cys
850 855 860

Cys Gly Ala Ala Gln Thr His Glu Phe Ser Ser Tyr Ile Asp Thr Gly
865 870 875 880

Asp Leu Asn Ser Thr Val Asp Gln Gly Ile Trp Ala Ile Phe Lys Val
885 890 895

Arg Thr Thr Asp Gly Tyr Ala Thr Leu Gly Asn Leu Glu Leu Val Glu
900 905 910

Ile Gly Pro Leu Ser Gly Glu Ser Leu Glu Arg Glu Gln Arg Asp Asn
915 920 925

```
Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                 1015                 1020

Gln Asn  Gly Asp Phe Asn Ser  Gly Leu Asp Ser Trp  Asn Ala Thr
    1025                 1030                 1035

Ala Gly  Ala Thr Val Gln Gln  Asp Gly Asn Thr His  Phe Leu Val
    1040                 1045                 1050

Leu Ser  His Trp Asp Ala Gln  Val Ser Gln Gln Phe  Arg Val Gln
    1055                 1060                 1065

Pro Asn  Cys Lys Tyr Val Leu  Arg Val Thr Ala Glu  Lys Val Gly
    1070                 1075                 1080

Gly Gly  Asp Gly Tyr Val Thr  Ile Arg Asp Gly Ala  His His Thr
    1085                 1090                 1095

Glu Thr  Leu Thr Phe Asn Ala  Cys Asp Tyr Asp Ile  Asn Gly Thr
    1100                 1105                 1110

Tyr Val  Thr Asp Asn Thr Tyr  Leu Thr Lys Glu Val  Val Phe Tyr
    1115                 1120                 1125

Ser His  Thr Glu His Met Trp  Val Glu Val Ser Glu  Thr Glu Gly
    1130                 1135                 1140

Val Phe  His Ile Asp Ser Val  Glu Phe Met Glu Thr  Gln Gln
    1145                 1150                 1155
```

<210> SEQ ID NO 27
<211> LENGTH: 1992
<212> TYPE: DNA
<213> ORGANISM: Artificial
<220> FEATURE:
<223> OTHER INFORMATION: Plant synthetic coding sequence encoding a TIC4064_17 pesticidal protein with an additional alanine codon inserted immediately following the initiating methionine and comprising a protoxin domain truncation and mutations at S34G, G88K, I386S, G403Q, and

<400> SEQUENCE: 27

```
atggctaacc agaacaagca cggcatcatt ggcgcatcca actgcgggtg taccagtgac      60

aacgtggcga aatacccgct cgccaataac ccatactcag gagccctgaa cctcaacagt     120

tgtcagaaca gctccatcct gaattggatc aacatcatcg gcgacgcggc gaaggaggcg     180

gtgagcatcg ggacaaccat cgtttcgctt atcacagctc cctcgctgac gggcctcatc     240

tcaatcgttt atgacctcat taagaaggtg ctcggcggct cgtccggcca atccattagc     300

gacctttcca tctgcgatct gctctccata attgacctgc gggtgtcgca gtcggtcctg     360

aacgacggga tagcggactt caacggcagc gtcctcctgt accgcaacta cctggaggca     420

ctggactcct ggaacaagaa tcccaacagc gccagcgcgg aggagctgcg gacgcgcttt     480

cgcatcgctg attctgagtt tgaccgaatc ctgacacgcg gctcccttac caacggcggt     540

agcctggctc gccagaacgc ccagattctg ttgctgccca gtttcgcgtc agccgcattc     600
```

```
tttcacctac ttctccttcg ggacgcaacg cgctacggga ccaattgggg attgtacaac    660

gcgacgccct tcatcaacta tcagtctaag ctcgtcgaac tgatcgaact ctacacggac    720

tactgcgtcc actggtacaa tcgtggcttt aacgagttgc gtcaacgcgg aacttctgct    780

acggcgtggc ttgagtttca cagataccgt cgtgagatga cgctaatggt cctcgacatc    840

gtggcgtcgt tcagctcgct tgacatcacc aactacccta tcgagaccga ctttcaactt    900

agccgtgtga tctacactga cccaatcggc ttcgtccatc gaagttcact ccgtggcgag    960

tcctggttct cgttcgtgaa ccgcgccaac ttcagtgacc ttgagaatgc gatccctaac   1020

ccacgcccta gctggttcct gaacaacatg attatctcta cagggagcct gaccttaccc   1080

gtcagtccca gcacagatcg cgcgagagtc tggtacggga gtcgggaccg gatctcgccc   1140

gccaactctc agttcagtac tgagcttatc tccgggcagc acaccaccgc cacccagaca   1200

atactccagc gcaacatctt ccgcgtggat tcacaggcgt gcaacctaaa cgacaccacg   1260

tacggcgtca accgcgccgt gttctaccat gacgcctcgg agggctcgca gcgtagcgtt   1320

tatgagggct acatcaggac gacgggtatc gacaacccga gagtgcagaa catcaacacc   1380

tatttgccag gcgagaacag cgacatcccg acgcccgaag actacaccca catcctcagc   1440

acaaccatca acctcacggg cgggctccgc caagttgcct cgaaccggcg gagcagcctc   1500

gttatgtacg gctggaccca caagtctctg gcgcgcaaca acaccatcaa tccagatcga   1560

atcacccaga taccactcac gaaggtggat acccgaggga ctggcgttag ttacgtcaac   1620

gatcctggat tcatcggcgg cgcgcttctc caacgcacgg accacgggtc gctgggcgtc   1680

cttcgggtac agtttccgct acacttgcgc cagcaatacc ggataagggt tcggtacgcc   1740

tcaacaacga acatcagact gtctgtcaac ggctccttcg gcaccatctc ccagaacctt   1800

ccctccacca tgaacctcgg tgaggatctg cgctacggct ctttcgctat ccgcgagttt   1860

agcacttcaa tacgcccaac cgcgtcacct gaccagatac gcctgaccat tgaaccgtcc   1920

ttcatccggc aagaggtgta cgtggacaga atcgagttca taccagtcaa cccgacgcgg   1980

gaggcgaagt ga                                                       1992
```

<210> SEQ ID NO 28
<211> LENGTH: 663
<212> TYPE: PRT
<213> ORGANISM: Artificial
<220> FEATURE:
<223> OTHER INFORMATION: Amino acid sequence of TIC4064_15 with an additional alanine amino acid inserted immediately following the initiating methionine and comprising a protoxin domain truncation and mutations at S34G, G88K, I386S, G403Q, and R605N.

<400> SEQUENCE: 28

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Gly Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
                85                  90                  95
```

-continued

```
Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

Arg Val Trp Tyr Gly Ser Arg Asp Arg Ile Ser Pro Ala Asn Ser Gln
    370                 375                 380

Phe Ser Thr Glu Leu Ile Ser Gly Gln His Thr Thr Ala Thr Gln Thr
385                 390                 395                 400

Ile Leu Gln Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
```

```
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp His Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Arg Leu Ser Val Asn Gly Ser
            580                 585                 590

Phe Gly Thr Ile Ser Gln Asn Leu Pro Ser Thr Met Asn Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys
            660


<210> SEQ ID NO 29
<211> LENGTH: 3474
<212> TYPE: DNA
<213> ORGANISM: Artificial
<220> FEATURE:
<223> OTHER INFORMATION: Plant synthetic coding sequence encoding a
      TIC4064_18 pesticidal protein with an additional alanine codon
      inserted immediately following the initiating methionine and
      comprising mutations at G88K, W371L, H555N, and R586Q.

<400> SEQUENCE: 29

atggctaacc agaacaagca cggcatcatt ggcgcatcca actgcgggtg taccagtgac     60

aacgtggcga aatacccgct cgccaataac ccatactcat cagccctgaa cctcaacagt    120

tgtcagaaca gctccatcct gaattggatc aacatcatcg gcgacgcggc gaaggaggcg    180

gtgagcatcg ggacaaccat cgtttcgctt atcacagctc cctcgctgac gggcctcatc    240

tcaatcgttt atgacctcat taagaaggtg ctcggcggct cgtccggcca atccattagc    300

gacctttcca tctgcgatct gctctccata attgacctgc gggtgtcgca gtcggtcctg    360

aacgacggga tagcggactt caacggcagc gtcctcctgt accgcaacta cctggaggca    420

ctggactcct ggaacaagaa tcccaacagc gccagcgcgg aggagctgcg gacgcgcttt    480

cgcatcgctg attctgagtt tgaccgaatc ctgacacgcg gctcccttac caacggcggt    540

agcctggctc gccagaacgc ccagattctg ttgctgccca gtttcgcgtc agccgcattc    600

tttcacctac ttctccttcg ggacgcaacg cgctacggga ccaattgggg attgtacaac    660

gcgacgccct tcatcaacta tcagtctaag ctcgtcgaac tgatcgaact ctacacggac    720

tactgcgtcc actggtacaa tcgtggcttt aacgagttgc gtcaacgcgg aacttctgct    780

acggcgtggc ttgagtttca cagataccgt cgtgagatga cgctaatggt cctcgacatc    840

gtggcgtcgt tcagctcgct tgacatcacc aactacccta tcgagaccga ctttcaactt    900

agccgtgtga tctacactga cccaatcggc ttcgtccatc gaagttcact ccgtggcgag    960

tcctggttct cgttcgtgaa ccgcgccaac ttcagtgacc ttgagaatgc gatccctaac   1020

ccacgcccta gctggttcct gaacaacatg attatctcta cagggagcct gaccttaccc   1080

gtcagtccca gcacagatcg cgcgagagtc ttgtacggga gtcgggaccg gatctcgccc   1140
```

-continued

```
gccaactctc agttcattac tgagcttatc tccgggcagc acaccaccgc cacccagaca   1200
atactcggtc gcaacatctt ccgcgtggat tcacaggcgt gcaacctaaa cgacaccacg   1260
tacggcgtca accgcgccgt gttctaccat gacgcctcgg agggctcgca gcgtagcgtt   1320
tatgagggct acatcaggac gacgggtatc gacaacccga gagtgcagaa catcaacacc   1380
tatttgccag gcgagaacag cgacatcccg acgcccgaag actacaccca catcctcagc   1440
acaaccatca acctcacggg cgggctccgc caagttgcct cgaaccggcg gagcagcctc   1500
gttatgtacg gctggaccca caagtctctg gcgcgcaaca acaccatcaa tccagatcga   1560
atcacccaga taccactcac gaaggtggat acccgaggga ctggcgttag ttacgtcaac   1620
gatcctggat tcatcggcgg cgcgcttctc caacgcacgg acaacgggtc gctgggcgtc   1680
cttcgggtac agtttccgct acacttgcgc cagcaatacc ggataagggt tcggtacgcc   1740
tcaacaacga acatccaact gtctgtcaac ggctccttcg gcaccatctc ccagaacctt   1800
ccctccacca tgcgcctcgg tgaggatctg cgctacggct ctttcgctat ccgcgagttt   1860
agcacttcaa tacgcccaac cgcgtcacct gaccagatac gcctgaccat tgaaccgtcc   1920
ttcatccggc aagaggtgta cgtggacaga atcgagttca taccagtcaa cccgacgcgg   1980
gaggcgaagg aagaccttga ggctaccaag aaggcggtgg cgagcctgtt tacccgcact   2040
cgtgacggcc tccaagtaaa tgtcacggac taccaagtgg accaggcggc caacctcgta   2100
agctgcctat cagacgagca gtacgcccac gacaagaaga tgcttctgga agccgtcaga   2160
gccgccaaac ggctatcgcg cgagcgcaac ctgctccaag atcccgactt caacactatc   2220
aacagcaccg aggagaatgg ctggaaagcc agcaacggcg tgacgattag cgagggcggc   2280
ccgttctaca agggccgcgc actacagctt gcctccgcaa gggagaacta ccctacctac   2340
atctaccaga aggtcgatgc gtcggaactt aaaccataca cacggtatcg tctcgacggg   2400
ttcgtcaaat ccagccaaga cctagagatc gacctcatcc accatcacaa agtacatctc   2460
gtcaagaatg cgcccgacaa tcttgtctct gacacttacc cggacgattc ctgttcgggt   2520
attaacagat gccaggagca gcagatggtg aacgcccaac tcgaaaccga gcaccatcac   2580
ccaatggact gctgcggtgc ggctcagacc cacgagttta gcagttacat cgacaccggc   2640
gacctgaact cgacggtgga ccagggcatc tgggcgatct tcaaggttcg taccaccgac   2700
ggctacgcga ctctcgggaa tctggaactg gtcgagatcg gcccgttgag cggcgagtcg   2760
ctggagcggg agcagaggga caacgcaaag tggtctgccg agctgggccg aaagcgagcg   2820
gagactgacc gcgtgtacca ggatgctaag caaagtatca accacctctt cgtggactat   2880
caagatcaac agctcaaccc tgagatcggg atggctgaca tcatggacgc gcagaacctg   2940
gtggcgtcga tctccgatgt gtactccgac gccgtgctcc aaatccctgg cattaactac   3000
gagatctaca cggagctgtc gaaccgcctc caacaagcga gctaccttta cacgagccgg   3060
aacgccgtac agaacggcga cttcaactcc gggctcgact catggaacgc cactgcgggc   3120
gctaccgtcc aacaagacgg caacacccac tttctcgtcc ttagccactg ggacgcccaa   3180
gtctcgcagc agtttcgcgt tcagccgaac tgcaagtatg tcctgcgcgt gaccgccgag   3240
aaggtgggcg gtggtgacgg ctacgtcacc ataagggatg gtgcccacca cacggagacc   3300
ttaacgttta acgcctgtga ttatgacatc aacggcacct atgtgacgga caatacctac   3360
ctcactaagg aagtcgtgtt ctattcccat accgagcaca tgtgggtcga ggtttcggag   3420
acggagggcg tattccacat cgacagtgtg gagttcatgg agacccagca gtga         3474
```

<210> SEQ ID NO 30
<211> LENGTH: 1157
<212> TYPE: PRT
<213> ORGANISM: Artificial
<220> FEATURE:
<223> OTHER INFORMATION: Amino acid sequence of TIC4064_18 with an additional alanine amino acid inserted immediately following the initiating methionine and comprising mutations at G88K, W371L, H555N, and R586Q.

<400> SEQUENCE: 30

```
Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350
```

```
Ser Thr Gly Ser Leu Thr Leu Pro Val Ser Pro Ser Thr Asp Arg Ala
        355                 360                 365

Arg Val Leu Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp Asn Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Gln Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys Glu Asp Leu Glu Ala Thr Lys Lys Ala
            660                 665                 670

Val Ala Ser Leu Phe Thr Arg Thr Arg Asp Gly Leu Gln Val Asn Val
        675                 680                 685

Thr Asp Tyr Gln Val Asp Gln Ala Ala Asn Leu Val Ser Cys Leu Ser
    690                 695                 700

Asp Glu Gln Tyr Ala His Asp Lys Lys Met Leu Leu Glu Ala Val Arg
705                 710                 715                 720

Ala Ala Lys Arg Leu Ser Arg Glu Arg Asn Leu Leu Gln Asp Pro Asp
                725                 730                 735

Phe Asn Thr Ile Asn Ser Thr Glu Glu Asn Gly Trp Lys Ala Ser Asn
            740                 745                 750

Gly Val Thr Ile Ser Glu Gly Gly Pro Phe Tyr Lys Gly Arg Ala Leu
        755                 760                 765

Gln Leu Ala Ser Ala Arg Glu Asn Tyr Pro Thr Tyr Ile Tyr Gln Lys
```

```
    770                 775                 780

Val Asp Ala Ser Glu Leu Lys Pro Tyr Thr Arg Tyr Arg Leu Asp Gly
785                 790                 795                 800

Phe Val Lys Ser Ser Gln Asp Leu Glu Ile Asp Leu Ile His His His
                805                 810                 815

Lys Val His Leu Val Lys Asn Ala Pro Asp Asn Leu Val Ser Asp Thr
            820                 825                 830

Tyr Pro Asp Asp Ser Cys Ser Gly Ile Asn Arg Cys Gln Glu Gln Gln
        835                 840                 845

Met Val Asn Ala Gln Leu Glu Thr Glu His His His Pro Met Asp Cys
    850                 855                 860

Cys Gly Ala Ala Gln Thr His Glu Phe Ser Ser Tyr Ile Asp Thr Gly
865                 870                 875                 880

Asp Leu Asn Ser Thr Val Asp Gln Gly Ile Trp Ala Ile Phe Lys Val
                885                 890                 895

Arg Thr Thr Asp Gly Tyr Ala Thr Leu Gly Asn Leu Glu Leu Val Glu
            900                 905                 910

Ile Gly Pro Leu Ser Gly Glu Ser Leu Glu Arg Glu Gln Arg Asp Asn
        915                 920                 925

Ala Lys Trp Ser Ala Glu Leu Gly Arg Lys Arg Ala Glu Thr Asp Arg
    930                 935                 940

Val Tyr Gln Asp Ala Lys Gln Ser Ile Asn His Leu Phe Val Asp Tyr
945                 950                 955                 960

Gln Asp Gln Gln Leu Asn Pro Glu Ile Gly Met Ala Asp Ile Met Asp
                965                 970                 975

Ala Gln Asn Leu Val Ala Ser Ile Ser Asp Val Tyr Ser Asp Ala Val
            980                 985                 990

Leu Gln Ile Pro Gly Ile Asn Tyr  Glu Ile Tyr Thr Glu  Leu Ser Asn
        995                 1000                1005

Arg Leu  Gln Gln Ala Ser Tyr  Leu Tyr Thr Ser Arg  Asn Ala Val
    1010                1015                1020

Gln Asn  Gly Asp Phe Asn Ser  Gly Leu Asp Ser Trp  Asn Ala Thr
    1025                1030                1035

Ala Gly  Ala Thr Val Gln Gln  Asp Gly Asn Thr His  Phe Leu Val
    1040                1045                1050

Leu Ser  His Trp Asp Ala Gln  Val Ser Gln Gln Phe  Arg Val Gln
    1055                1060                1065

Pro Asn  Cys Lys Tyr Val Leu  Arg Val Thr Ala Glu  Lys Val Gly
    1070                1075                1080

Gly Gly  Asp Gly Tyr Val Thr  Ile Arg Asp Gly Ala  His His Thr
    1085                1090                1095

Glu Thr  Leu Thr Phe Asn Ala  Cys Asp Tyr Asp Ile  Asn Gly Thr
    1100                1105                1110

Tyr Val  Thr Asp Asn Thr Tyr  Leu Thr Lys Glu Val  Val Phe Tyr
    1115                1120                1125

Ser His  Thr Glu His Met Trp  Val Glu Val Ser Glu  Thr Glu Gly
    1130                1135                1140

Val Phe  His Ile Asp Ser Val  Glu Phe Met Glu Thr  Gln Gln
    1145                1150                1155
```

<210> SEQ ID NO 31
<211> LENGTH: 1992
<212> TYPE: DNA
<213> ORGANISM: Artificial
<220> FEATURE:
<223> OTHER INFORMATION: Plant synthetic coding sequence encoding a TIC4064_19 pesticidal protein with an additional alanine codon inserted immediately following the initiating methionine and comprising a protoxin doamin truncation and mutations at G88K, W371L, H555N, and R586Q.

<400> SEQUENCE: 31
atggctaacc agaacaagca cggcatcatt ggcgcatcca actgcgggtg taccagtgac 60
aacgtggcga aatacccgct cgccaataac ccatactcat cagccctgaa cctcaacagt 120
tgtcagaaca gctccatcct gaattggatc aacatcatcg gcgacgcggc gaaggaggcg 180
gtgagcatcg ggacaaccat cgtttcgctt atcacagctc cctcgctgac gggcctcatc 240
tcaatcgttt atgacctcat taagaaggtg ctcggcggct cgtccggcca atccattagc 300
gacctttcca tctgcgatct gctctccata attgacctgc gggtgtcgca gtcggtcctg 360
aacgacggga tagcggactt caacggcagc gtcctcctgt accgcaacta cctggaggca 420
ctggactcct ggaacaagaa tcccaacagc gccagcgcgg aggagctgcg gacgcgcttt 480
cgcatcgctg attctgagtt tgaccgaatc ctgacacgcg gctcccttac caacggcggt 540
agcctggctc gccagaacgc ccagattctg ttgctgccca gtttcgcgtc agccgcattc 600
tttcacctac ttctccttcg ggacgcaacg cgctacggga ccaattgggg attgtacaac 660
gcgacgccct tcatcaacta tcagtctaag ctcgtcgaac tgatcgaact ctacacggac 720
tactgcgtcc actggtacaa tcgtggcttt aacgagttgc gtcaacgcgg aacttctgct 780
acggcgtggc ttgagtttca cagataccgt cgtgagatga cgctaatggt cctcgacatc 840
gtggcgtcgt tcagctcgct tgacatcacc aactacccta tcgagaccga ctttcaactt 900
agccgtgtga tctacactga cccaatcggc ttcgtccatc gaagttcact ccgtggcgag 960
tcctggttct cgttcgtgaa ccgcgccaac ttcagtgacc ttgagaatgc gatccctaac 1020
ccacgcccta gctggttcct gaacaacatg attatctcta cagggagcct gaccttaccc 1080
gtcagtccca gcacagatcg cgcgagagtc ttgtacggga gtcgggaccg gatctcgccc 1140
gccaactctc agttcattac tgagcttatc tccgggcagc acaccaccgc cacccagaca 1200
atactcggtc gcaacatctt ccgcgtggat tcacaggcgt gcaacctaaa cgacaccacg 1260
tacggcgtca accgcgccgt gttctaccat gacgcctcgg agggctcgca gcgtagcgtt 1320
tatgagggct acatcaggac gacgggtatc gacaacccga gagtgcagaa catcaacacc 1380
tatttgccag gcgagaacag cgacatcccg acgcccgaag actacaccca catcctcagc 1440
acaaccatca acctcacggg cgggctccgc caagttgcct cgaaccggcg gagcagcctc 1500
gttatgtacg gctggaccca caagtctctg gcgcgcaaca acaccatcaa tccagatcga 1560
atcacccaga taccactcac gaaggtggat acccgaggga ctggcgttag ttacgtcaac 1620
gatcctggat tcatcggcgg cgcgcttctc caacgcacgg acaacgggtc gctgggcgtc 1680
cttcgggtac agtttccgct acacttgcgc cagcaatacc ggataagggt tcggtacgcc 1740
tcaacaacga acatccaact gtctgtcaac ggctccttcg gcaccatctc ccagaacctt 1800
ccctccacca tgcgcctcgg tgaggatctg cgctacggct ctttcgctat ccgcgagttt 1860
agcacttcaa tacgcccaac cgcgtcacct gaccagatac gcctgaccat tgaaccgtcc 1920
ttcatccggc aagaggtgta cgtggacaga atcgagttca taccagtcaa cccgacgcgg 1980
gaggcgaagt ga 1992

<210> SEQ ID NO 32

<211> LENGTH: 663
<212> TYPE: PRT
<213> ORGANISM: Artificial
<220> FEATURE:
<223> OTHER INFORMATION: Amino acid sequence of TIC4064_19 with an additional alanine amino acid inserted immediately following the initiating methionine and comprising a protoxin domain truncation and mutations at G88K, W371L, H555N, and R586Q.

<400> SEQUENCE: 32

Met Ala Asn Gln Asn Lys His Gly Ile Ile Gly Ala Ser Asn Cys Gly
1               5                   10                  15

Cys Thr Ser Asp Asn Val Ala Lys Tyr Pro Leu Ala Asn Asn Pro Tyr
            20                  25                  30

Ser Ser Ala Leu Asn Leu Asn Ser Cys Gln Asn Ser Ser Ile Leu Asn
        35                  40                  45

Trp Ile Asn Ile Ile Gly Asp Ala Ala Lys Glu Ala Val Ser Ile Gly
    50                  55                  60

Thr Thr Ile Val Ser Leu Ile Thr Ala Pro Ser Leu Thr Gly Leu Ile
65                  70                  75                  80

Ser Ile Val Tyr Asp Leu Ile Lys Lys Val Leu Gly Gly Ser Ser Gly
                85                  90                  95

Gln Ser Ile Ser Asp Leu Ser Ile Cys Asp Leu Leu Ser Ile Ile Asp
            100                 105                 110

Leu Arg Val Ser Gln Ser Val Leu Asn Asp Gly Ile Ala Asp Phe Asn
        115                 120                 125

Gly Ser Val Leu Leu Tyr Arg Asn Tyr Leu Glu Ala Leu Asp Ser Trp
    130                 135                 140

Asn Lys Asn Pro Asn Ser Ala Ser Ala Glu Glu Leu Arg Thr Arg Phe
145                 150                 155                 160

Arg Ile Ala Asp Ser Glu Phe Asp Arg Ile Leu Thr Arg Gly Ser Leu
                165                 170                 175

Thr Asn Gly Gly Ser Leu Ala Arg Gln Asn Ala Gln Ile Leu Leu Leu
            180                 185                 190

Pro Ser Phe Ala Ser Ala Ala Phe Phe His Leu Leu Leu Leu Arg Asp
        195                 200                 205

Ala Thr Arg Tyr Gly Thr Asn Trp Gly Leu Tyr Asn Ala Thr Pro Phe
    210                 215                 220

Ile Asn Tyr Gln Ser Lys Leu Val Glu Leu Ile Glu Leu Tyr Thr Asp
225                 230                 235                 240

Tyr Cys Val His Trp Tyr Asn Arg Gly Phe Asn Glu Leu Arg Gln Arg
                245                 250                 255

Gly Thr Ser Ala Thr Ala Trp Leu Glu Phe His Arg Tyr Arg Arg Glu
            260                 265                 270

Met Thr Leu Met Val Leu Asp Ile Val Ala Ser Phe Ser Ser Leu Asp
        275                 280                 285

Ile Thr Asn Tyr Pro Ile Glu Thr Asp Phe Gln Leu Ser Arg Val Ile
    290                 295                 300

Tyr Thr Asp Pro Ile Gly Phe Val His Arg Ser Ser Leu Arg Gly Glu
305                 310                 315                 320

Ser Trp Phe Ser Phe Val Asn Arg Ala Asn Phe Ser Asp Leu Glu Asn
                325                 330                 335

Ala Ile Pro Asn Pro Arg Pro Ser Trp Phe Leu Asn Asn Met Ile Ile
            340                 345                 350

Ser Thr Gly Ser Leu Thr Leu Pro Val Ser Pro Ser Thr Asp Arg Ala
        355                 360                 365

```
Arg Val Leu Tyr Gly Ser Arg Asp Arg Ile Ser Pro Ala Asn Ser Gln
    370                 375                 380

Phe Ile Thr Glu Leu Ile Ser Gly Gln His Thr Thr Ala Thr Gln Thr
385                 390                 395                 400

Ile Leu Gly Arg Asn Ile Phe Arg Val Asp Ser Gln Ala Cys Asn Leu
                405                 410                 415

Asn Asp Thr Thr Tyr Gly Val Asn Arg Ala Val Phe Tyr His Asp Ala
            420                 425                 430

Ser Glu Gly Ser Gln Arg Ser Val Tyr Glu Gly Tyr Ile Arg Thr Thr
        435                 440                 445

Gly Ile Asp Asn Pro Arg Val Gln Asn Ile Asn Thr Tyr Leu Pro Gly
    450                 455                 460

Glu Asn Ser Asp Ile Pro Thr Pro Glu Asp Tyr Thr His Ile Leu Ser
465                 470                 475                 480

Thr Thr Ile Asn Leu Thr Gly Gly Leu Arg Gln Val Ala Ser Asn Arg
                485                 490                 495

Arg Ser Ser Leu Val Met Tyr Gly Trp Thr His Lys Ser Leu Ala Arg
            500                 505                 510

Asn Asn Thr Ile Asn Pro Asp Arg Ile Thr Gln Ile Pro Leu Thr Lys
        515                 520                 525

Val Asp Thr Arg Gly Thr Gly Val Ser Tyr Val Asn Asp Pro Gly Phe
    530                 535                 540

Ile Gly Gly Ala Leu Leu Gln Arg Thr Asp Asn Gly Ser Leu Gly Val
545                 550                 555                 560

Leu Arg Val Gln Phe Pro Leu His Leu Arg Gln Gln Tyr Arg Ile Arg
                565                 570                 575

Val Arg Tyr Ala Ser Thr Thr Asn Ile Gln Leu Ser Val Asn Gly Ser
            580                 585                 590

Phe Gly Thr Ile Ser Gln Asn Leu Pro Ser Thr Met Arg Leu Gly Glu
        595                 600                 605

Asp Leu Arg Tyr Gly Ser Phe Ala Ile Arg Glu Phe Ser Thr Ser Ile
    610                 615                 620

Arg Pro Thr Ala Ser Pro Asp Gln Ile Arg Leu Thr Ile Glu Pro Ser
625                 630                 635                 640

Phe Ile Arg Gln Glu Val Tyr Val Asp Arg Ile Glu Phe Ile Pro Val
                645                 650                 655

Asn Pro Thr Arg Glu Ala Lys
            660
```

<210> SEQ ID NO 33
<211> LENGTH: 3471
<212> TYPE: DNA
<213> ORGANISM: Artificial
<220> FEATURE:
<223> OTHER INFORMATION: Synthetic bacterial coding sequence encoding TIC4064_20 comprising mutations at S94T, D84A, A510H, N512D, and D608A.

<400> SEQUENCE: 33

```
atgaatcaaa ataaacacgg aattattggc gcttccaatt gtggttgtac gtcagataat      60

gttgcgaaat atcctttagc caacaatcca tattcatctg ctttaaattt aaattcttgt     120

caaaatagta gtattctcaa ctggattaac ataataggcg atgcagcaaa agaagcagta     180

tctattggga caacaatagt ctctcttatc acagcacctt ctcttactgg attaatttca     240

atagtatatg cacttatagg taaagtacta ggaggtagta caggacaatc catatcagat     300
```

-continued

```
ttgtctatat gtgacttatt atctattatt gatttacggg taagtcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc aattggtttt gtacatcgta gtagtcttag gggagaaagt    960
tggtttagct ttgttaatag agctaatttc tcagatttag aaaatgcaat acctaatcct   1020
agaccgtctt ggtttttaaa taatatgatt atatctactg gttcacttac attgccggtt   1080
agcccaagta ctgatagagc gagggtatgg tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctgcat cgtgataata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggcattaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
```

-continued

```
ttaaattcga ctgtagacca gggaatctgg gcgatcttta aagttcgaac aacagatggt   2700

tatgcgacgt taggaaatct tgaattggta gagatcggac cgttatcggg tgaatctcta   2760

gaacgtgaac aaagggataa tgcaaaatgg agtgcagagc taggaagaaa gcgtgcagaa   2820

acagatcgcg tgtatcaaga tgccaaacaa tccatcaatc atttatttgt ggattatcaa   2880

gatcaacaat taaatccaga aatagggatg gcagatatta tggacgctca aaatcttgtc   2940

gcatcaattt cagatgtata tagcgatgca gtactgcaaa tccctggaat taactatgag   3000

atttacacag agctatccaa tcgcttacaa caagcatcgt atctgtatac gtctcgaaat   3060

gcggtgcaaa atggggactt taacagcggt ctagatagtt ggaatgcaac agcgggtgct   3120

acggtacaac aggatggtaa tacgcatttc ttagttcttt ctcattggga tgcacaagtt   3180

tctcaacaat ttagagtgca gccaaattgt aaatatgtat tacgtgtaac agcagagaaa   3240

gtaggcggcg gagacggata cgtgacaatc cgggatggtg ctcatcatac agaaacgctt   3300

acatttaatg catgtgatta tgatataaat ggcacgtacg tgactgataa tacgtatcta   3360

acaaaagaag tggtattcta ttcacataca gaacacatgt gggtagaggt aagtgaaaca   3420

gaaggtgttt tccatataga cagtgttgag ttcatggaaa cccaacagta g            3471
```

<210> SEQ ID NO 34
<211> LENGTH: 1156
<212> TYPE: PRT
<213> ORGANISM: Artificial
<220> FEATURE:
<223> OTHER INFORMATION: Amino acid sequence of TIC4064_20 comprising
      mutations at S94T, D84A, A510H, N512D, and D608A.

<400> SEQUENCE: 34

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Ala Leu Ile Gly Lys Val Leu Gly Gly Ser Thr Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
```

-continued

```
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu His Arg Asp
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Ala
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640
```

```
Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020

Asn Gly  Asp Phe Asn Ser Gly  Leu Asp Ser Trp Asn  Ala Thr Ala
    1025                1030                1035

Gly Ala  Thr Val Gln Gln Asp  Gly Asn Thr His Phe  Leu Val Leu
    1040                1045                1050
```

-continued

```
Ser His  Trp Asp Ala Gln Val  Ser Gln Gln Phe Arg  Val Gln Pro
    1055                 1060                 1065

Asn Cys  Lys Tyr Val Leu Arg  Val Thr Ala Glu Lys  Val Gly Gly
    1070                 1075                 1080

Gly Asp  Gly Tyr Val Thr Ile  Arg Asp Gly Ala His  His Thr Glu
    1085                 1090                 1095

Thr Leu  Thr Phe Asn Ala Cys  Asp Tyr Asp Ile Asn  Gly Thr Tyr
    1100                 1105                 1110

Val Thr  Asp Asn Thr Tyr Leu  Thr Lys Glu Val Val  Phe Tyr Ser
    1115                 1120                 1125

His Thr  Glu His Met Trp Val  Glu Val Ser Glu Thr  Glu Gly Val
    1130                 1135                 1140

Phe His  Ile Asp Ser Val Glu  Phe Met Glu Thr Gln  Gln
    1145                 1150                 1155
```

```
<210> SEQ ID NO 35
<211> LENGTH: 3471
<212> TYPE: DNA
<213> ORGANISM: Artificial
<220> FEATURE:
<223> OTHER INFORMATION: Synthetic bacterial coding sequence encoding
      TIC4064_21 comprising mutations at S94T, R168K, and S331A.

<400> SEQUENCE: 35

atgaatcaaa ataaacacgg aattattggc gcttccaatt gtggttgtac gtcagataat     60

gttgcgaaat atcctttagc caacaatcca tattcatctg ctttaaattt aaattcttgt    120

caaaatagta gtattctcaa ctggattaac ataataggcg atgcagcaaa agaagcagta    180

tctattggga caacaatagt ctctcttatc acagcacctt ctcttactgg attaatttca    240

atagtatatg cacttatagg taaagtacta ggaggtagta caggacaatc catatcagat    300

ttgtctatat gtgacttatt atctattatt gatttacggg taagtcagag tgttttaaat    360

gatgggattg cagattttaa tggttctgta ctcttataca ggaactattt agaggctctg    420

gatagctgga ataagaatcc taattctgct tctgctgaag aactccgtac tcgttttaga    480

atcgctgact cagaatttga tagaatttta acacgagggt ctttaacgaa tggtggctcg    540

ttagctagac aaaatgccca aatattatta ttaccttctt ttgcgagtgc tgcatttttc    600

catttattac tactaaggga tgctactaga tatggcacta attgggggct atacaatgct    660

acacctttta taaattatca atcaaaacta gtagagctta ttgaactata tactgattat    720

tgcgtacatt ggtataatcg aggtttcaac gaactaaggc aacgaggcac tagtgctaca    780

gcttggttag aatttcatag atatcgtaga gagatgacat tgatggtatt agatatagta    840

gcatcatttt caagtcttga tattactaat tacccaatag aaacagattt tcagttgagt    900

agggtcattt atacagatcc aattggtttt gtacatcgta gtagtcttag gggagaaagt    960

tggtttagct ttgttaatag agctaatttc tcagatttag aaaatgcaat acctaatcct   1020

agaccgtctt ggtttttaaa taatatgatt atatctactg gttcacttac attgccggtt   1080

agcccaagta ctgatagagc gagggtatgg tatggaagtc gagatcgaat ttcccctgct   1140

aattcacaat ttattactga actaatctct ggacaacata cgactgctac acaaactatt   1200

ttagggcgaa atatatttag agtagattct caagcttgta atttaaatga taccacatat   1260

ggagtgaata gggcggtatt ttatcatgat gcgagtgaag gttctcaaag atccgtgtac   1320

gaggggtata ttcgaacaac tgggatagat aaccctagag ttcaaaatat taacacttat   1380

ttacctggag aaaattcaga tatcccaact ccagaagact atactcatat attaagcaca   1440
```

```
acaataaatt taacaggagg acttagacaa gtagcatcta atcgccgttc atctttagta   1500

atgtatggtt ggacacataa aagtctgcat cgtgataata ccattaatcc agatagaatt   1560

acacagatac cattgacgaa ggttgatacc cgaggcacag gtgtttctta tgtgaatgat   1620

ccaggattta taggaggagc tctacttcaa aggactgacc atggttcgct tggagtattg   1680

agggtccaat ttccacttca cttaagacaa caatatcgca ttagagtccg ttatgcttct   1740

acaacaaata ttcgattgag tgtgaatggc agtttcggta ctatttctca aaatctccct   1800

agtacaatga gattaggaga ggcattaaga tacggatctt ttgctataag agagtttagt   1860

acttctatta gacccactgc aagtccggac caaattcgat tgacaataga accatctttt   1920

attagacaag aggtctatgt agatagaatt gagttcattc cagttaatcc gacgcgagag   1980

gcgaaagagg atctagaagc aacaaagaaa gcggtggcga gcttgtttac acgcacaagg   2040

gacggattac aagtaaatgt gacagattat caagtcgatc aagcggcaaa tttagtgtca   2100

tgcttatcag atgaacaata tgcgcatgat aaaaagatgt tattggaagc ggtacgcgcg   2160

gcaaaacgcc tcagccgaga acgcaactta cttcaggatc cagattttaa tacaatcaat   2220

agtacagaag aaaatggatg gaaagcaagt aacggcgtta ctattagcga aggcggtcca   2280

ttctataaag gccgtgcact tcagctagca agtgcacgag aaaattaccc aacatacatc   2340

tatcaaaaag tagatgcatc ggagttaaag ccgtatacac gttatagact ggatgggttc   2400

gtgaagagta gtcaagattt agaaattgat ctcattcacc atcataaagt ccatcttgtg   2460

aaaaatgcac cagataattt agtatctgat acttacccag atgattcttg tagtggaatc   2520

aatcgatgtc aggaacaaca gatggtaaat gcgcaactgg aaacagaaca tcatcatccg   2580

atggattgct gtggagcagc tcaaacacat gagttttctt cctatattga tacaggggat   2640

ttaaattcga ctgtagacca gggaatctgg gcgatcttta aagttcgaac aacagatggt   2700

tatgcgacgt taggaaatct tgaattggta gagatcggac cgttatcggg tgaatctcta   2760

gaacgtgaac aaagggataa tgcaaaatgg agtgcagagc taggaagaaa gcgtgcagaa   2820

acagatcgcg tgtatcaaga tgccaaacaa tccatcaatc atttatttgt ggattatcaa   2880

gatcaacaat taaatccaga aatagggatg gcagatatta tggacgctca aaatcttgtc   2940

gcatcaattt cagatgtata tagcgatgca gtactgcaaa tccctggaat taactatgag   3000

atttacacag agctatccaa tcgcttacaa caagcatcgt atctgtatac gtctcgaaat   3060

gcggtgcaaa atggggactt taacagcggt ctagatagtt ggaatgcaac agcgggtgct   3120

acggtacaac aggatggtaa tacgcatttc ttagttcttt ctcattggga tgcacaagtt   3180

tctcaacaat ttagagtgca gccaaattgt aaatatgtat tacgtgtaac agcagagaaa   3240

gtaggcggcg gagacggata cgtgacaatc cgggatggtg ctcatcatac agaaacgctt   3300

acatttaatg catgtgatta tgatataaat ggcacgtacg tgactgataa tacgtatcta   3360

acaaaagaag tggtattcta ttcacataca gaacacatgt gggtagaggt aagtgaaaca   3420

gaaggtgttt tccatataga cagtgttgag ttcatggaaa cccaacagta g            3471
```

<210> SEQ ID NO 36
<211> LENGTH: 1156
<212> TYPE: PRT
<213> ORGANISM: Artificial
<220> FEATURE:
<223> OTHER INFORMATION: Amino acid sequence of TIC4064_21 comprising mutations at S94T, R168K, and S331A.

<400> SEQUENCE: 36

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Ala Leu Ile Gly Lys Val Leu Gly Gly Ser Thr Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415
```

-continued

```
Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu His Arg Asp
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Ala
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
```

```
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020

Asn Gly  Asp Phe Asn Ser Gly  Leu Asp Ser Trp Asn  Ala Thr Ala
    1025                1030                1035

Gly Ala  Thr Val Gln Gln Asp  Gly Asn Thr His Phe  Leu Val Leu
    1040                1045                1050

Ser His  Trp Asp Ala Gln Val  Ser Gln Gln Phe Arg  Val Gln Pro
    1055                1060                1065

Asn Cys  Lys Tyr Val Leu Arg  Val Thr Ala Glu Lys  Val Gly Gly
    1070                1075                1080

Gly Asp  Gly Tyr Val Thr Ile  Arg Asp Gly Ala His  His Thr Glu
    1085                1090                1095

Thr Leu  Thr Phe Asn Ala Cys  Asp Tyr Asp Ile Asn  Gly Thr Tyr
    1100                1105                1110

Val Thr  Asp Asn Thr Tyr Leu  Thr Lys Glu Val Val  Phe Tyr Ser
    1115                1120                1125

His Thr  Glu His Met Trp Val  Glu Val Ser Glu Thr  Glu Gly Val
    1130                1135                1140

Phe His  Ile Asp Ser Val Glu  Phe Met Glu Thr Gln  Gln
    1145                1150                1155


<210> SEQ ID NO 37
<211> LENGTH: 3471
<212> TYPE: DNA
<213> ORGANISM: Artificial
<220> FEATURE:
<223> OTHER INFORMATION: Synthetic bacterial coding sequence encoding
      TIC4064_22 comprising mutations at S33G and S94T.

<400> SEQUENCE: 37

atgaatcaaa ataaacacgg aattattggc gcttccaatt gtggttgtac gtcagataat      60

gttgcgaaat atcctttagc caacaatcca tattcaggag ctttaaattt aaattcttgt     120

caaaatagta gtattctcaa ctggattaac ataataggcg atgcagcaaa agaagcagta     180
```

-continued

```
tctattggga caacaatagt ctctcttatc acagcacctt ctcttactgg attaatttca    240
atagtatatg accttatagg taaagtacta ggaggtagta caggacaatc catatcagat    300
ttgtctatat gtgacttatt atctattatt gatttacggg taagtcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc aattggtttt gtacatcgta gtagtcttag gggagaaagt    960
tggtttagct ttgttaatag agctaatttc tcagatttag aaaatgcaat acctaatcct   1020
agaccgtctt ggtttttaaa taatatgatt atatctactg gttcacttac attgccggtt   1080
agcccaagta ctgatagagc gagggtatgg tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
```

-continued atggattgct gtggagcagc tcaaacacat gagttttctt cctatattga tacaggggat 2640
ttaaattcga ctgtagacca gggaatctgg gcgatcttta aagttcgaac aacagatggt 2700
tatgcgacgt taggaaatct tgaattggta gagatcggac cgttatcggg tgaatctcta 2760
gaacgtgaac aaagggataa tgcaaaatgg agtgcagagc taggaagaaa gcgtgcagaa 2820
acagatcgcg tgtatcaaga tgccaaacaa tccatcaatc atttatttgt ggattatcaa 2880
gatcaacaat taaatccaga aatagggatg gcagatatta tggacgctca aaatcttgtc 2940
gcatcaattt cagatgtata tagcgatgca gtactgcaaa tccctggaat taactatgag 3000
atttacacag agctatccaa tcgcttacaa caagcatcgt atctgtatac gtctcgaaat 3060
gcggtgcaaa atggggactt taacagcggt ctagatagtt ggaatgcaac agcgggtgct 3120
acggtacaac aggatggtaa tacgcatttc ttagttcttt ctcattggga tgcacaagtt 3180
tctcaacaat ttagagtgca gccaaattgt aaatatgtat tacgtgtaac agcagagaaa 3240
gtaggcggcg gagacggata cgtgacaatc cgggatggtg ctcatcatac agaaacgctt 3300
acatttaatg catgtgatta tgatataaat ggcacgtacg tgactgataa tacgtatcta 3360
acaaaagaag tggtattcta ttcacataca gaacacatgt gggtagaggt aagtgaaaca 3420
gaaggtgttt tccatataga cagtgttgag ttcatggaaa cccaacagta g 3471

<210> SEQ ID NO 38
<211> LENGTH: 1156
<212> TYPE: PRT
<213> ORGANISM: Artificial
<220> FEATURE:
<223> OTHER INFORMATION: Amino acid sequence of TIC4064_22 comprising
mutations at S33G and S94T.

<400> SEQUENCE: 38

Met Asn Gln Asn Lys His Gly Ile Ile Gly Ala Ser Asn Cys Gly Cys
1 5 10 15

Thr Ser Asp Asn Val Ala Lys Tyr Pro Leu Ala Asn Asn Pro Tyr Ser
20 25 30

Gly Ala Leu Asn Leu Asn Ser Cys Gln Asn Ser Ser Ile Leu Asn Trp
35 40 45

Ile Asn Ile Ile Gly Asp Ala Ala Lys Glu Ala Val Ser Ile Gly Thr
50 55 60

Thr Ile Val Ser Leu Ile Thr Ala Pro Ser Leu Thr Gly Leu Ile Ser
65 70 75 80

Ile Val Tyr Asp Leu Ile Gly Lys Val Leu Gly Gly Ser Thr Gly Gln
85 90 95

Ser Ile Ser Asp Leu Ser Ile Cys Asp Leu Leu Ser Ile Ile Asp Leu
100 105 110

Arg Val Ser Gln Ser Val Leu Asn Asp Gly Ile Ala Asp Phe Asn Gly
115 120 125

Ser Val Leu Leu Tyr Arg Asn Tyr Leu Glu Ala Leu Asp Ser Trp Asn
130 135 140

Lys Asn Pro Asn Ser Ala Ser Ala Glu Glu Leu Arg Thr Arg Phe Arg
145 150 155 160

Ile Ala Asp Ser Glu Phe Asp Arg Ile Leu Thr Arg Gly Ser Leu Thr
165 170 175

Asn Gly Gly Ser Leu Ala Arg Gln Asn Ala Gln Ile Leu Leu Leu Pro
180 185 190

Ser Phe Ala Ser Ala Ala Phe Phe His Leu Leu Leu Leu Arg Asp Ala

-continued

```
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620
```

```
Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020

Asn Gly  Asp Phe Asn Ser Gly  Leu Asp Ser Trp Asn  Ala Thr Ala
    1025                1030                1035
```

-continued

```
Gly Ala  Thr Val Gln Gln Asp  Gly Asn Thr His Phe  Leu Val Leu
    1040                 1045                 1050

Ser His  Trp Asp Ala Gln Val  Ser Gln Gln Phe Arg  Val Gln Pro
    1055                 1060                 1065

Asn Cys  Lys Tyr Val Leu Arg  Val Thr Ala Glu Lys  Val Gly Gly
    1070                 1075                 1080

Gly Asp  Gly Tyr Val Thr Ile  Arg Asp Gly Ala His  His Thr Glu
    1085                 1090                 1095

Thr Leu  Thr Phe Asn Ala Cys  Asp Tyr Asp Ile Asn  Gly Thr Tyr
    1100                 1105                 1110

Val Thr  Asp Asn Thr Tyr Leu  Thr Lys Glu Val Val  Phe Tyr Ser
    1115                 1120                 1125

His Thr  Glu His Met Trp Val  Glu Val Ser Glu Thr  Glu Gly Val
    1130                 1135                 1140

Phe His  Ile Asp Ser Val Glu  Phe Met Glu Thr Gln  Gln
    1145                 1150                 1155
```

<210> SEQ ID NO 39
<211> LENGTH: 3471
<212> TYPE: DNA
<213> ORGANISM: Artificial
<220> FEATURE:
<223> OTHER INFORMATION: Synthetic bacterial coding sequence encoding TIC4064_23 comprising mutations at S94T, E153D, Q436I, and S596Q.

<400> SEQUENCE: 39

```
atgaatcaaa ataaacacgg aattattggc gcttccaatt gtggttgtac gtcagataat     60

gttgcgaaat atcctttagc caacaatcca tattcatctg ctttaaattt aaattcttgt    120

caaaatagta gtattctcaa ctggattaac ataataggcg atgcagcaaa agaagcagta    180

tctattggga caacaatagt ctctcttatc acagcacctt ctcttactgg attaatttca    240

atagtatatg accttatagg taaagtacta ggaggtagta caggacaatc catatcagat    300

ttgtctatat gtgacttatt atctattatt gatttacggg taagtcagag tgttttaaat    360

gatgggattg cagattttaa tggttctgta ctcttataca ggaactattt agaggctctg    420

gatagctgga ataagaatcc taattctgct tctgctgatg aactccgtac tcgttttaga    480

atcgctgact cagaatttga tagaatttta acacgagggt ctttaacgaa tggtggctcg    540

ttagctagac aaaatgccca aatattatta ttaccttctt ttgcgagtgc tgcatttttc    600

catttattac tactaaggga tgctactaga tatggcacta attgggggct atacaatgct    660

acacctttta taaattatca atcaaaacta gtagagctta ttgaactata tactgattat    720

tgcgtacatt ggtataatcg aggtttcaac gaactaaggc aacgaggcac tagtgctaca    780

gcttggttag aatttcatag atatcgtaga gagatgacat tgatggtatt agatatagta    840

gcatcatttt caagtcttga tattactaat tacccaatag aaacagattt tcagttgagt    900

agggtcattt atacagatcc aattggtttt gtacatcgta gtagtcttag gggagaaagt    960

tggtttagct ttgttaatag agctaatttc tcagatttag aaaatgcaat acctaatcct   1020

agaccgtctt ggtttttaaa taatatgatt atatctactg gttcacttac attgccggtt   1080

agcccaagta ctgatagagc gagggtatgg tatggaagtc gagatcgaat ttcccctgct   1140

aattcacaat ttattactga actaatctct ggacaacata cgactgctac acaaactatt   1200

ttagggcgaa atatatttag agtagattct caagcttgta atttaaatga taccacatat   1260

ggagtgaata gggcggtatt ttatcatgat gcgagtgaag gttctattag atccgtgtac   1320
```

-continued

```
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctattcaaca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
ttaaattcga ctgtagacca gggaatctgg gcgatcttta aagttcgaac aacagatggt   2700
tatgcgacgt taggaaatct tgaattggta gagatcggac cgttatcggg tgaatctcta   2760
gaacgtgaac aaagggataa tgcaaaatgg agtgcagagc taggaagaaa gcgtgcagaa   2820
acagatcgcg tgtatcaaga tgccaaacaa tccatcaatc atttatttgt ggattatcaa   2880
gatcaacaat taaatccaga aatagggatg gcagatatta tggacgctca aaatcttgtc   2940
gcatcaattt cagatgtata tagcgatgca gtactgcaaa tccctggaat taactatgag   3000
atttacacag agctatccaa tcgcttacaa caagcatcgt atctgtatac gtctcgaaat   3060
gcggtgcaaa atggggactt taacagcggt ctagatagtt ggaatgcaac agcgggtgct   3120
acggtacaac aggatggtaa tacgcatttc ttagttcttt ctcattggga tgcacaagtt   3180
tctcaacaat ttagagtgca gccaaattgt aaatatgtat tacgtgtaac agcagagaaa   3240
gtaggcggcg gagacggata cgtgacaatc cgggatggtg ctcatcatac agaaacgctt   3300
acatttaatg catgtgatta tgatataaat ggcacgtacg tgactgataa tacgtatcta   3360
acaaaagaag tggtattcta ttcacataca gaacacatgt gggtagaggt aagtgaaaca   3420
gaaggtgttt tccatataga cagtgttgag ttcatggaaa cccaacagta g            3471
```

<210> SEQ ID NO 40
<211> LENGTH: 1156
<212> TYPE: PRT
<213> ORGANISM: Artificial
<220> FEATURE:
<223> OTHER INFORMATION: Amino acid sequence of TIC4064_23 comprising mutations at S94T, E153D, Q436I, and S596Q.

<400> SEQUENCE: 40

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Thr Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Asp Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400
```

```
Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Ile Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Gln Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
```

```
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                 1015                1020

Asn Gly  Asp Phe Asn Ser Gly  Leu Asp Ser Trp Asn  Ala Thr Ala
    1025                 1030                1035

Gly Ala  Thr Val Gln Gln Asp  Gly Asn Thr His Phe  Leu Val Leu
    1040                 1045                1050

Ser His  Trp Asp Ala Gln Val  Ser Gln Gln Phe Arg  Val Gln Pro
    1055                 1060                1065

Asn Cys  Lys Tyr Val Leu Arg  Val Thr Ala Glu Lys  Val Gly Gly
    1070                 1075                1080

Gly Asp  Gly Tyr Val Thr Ile  Arg Asp Gly Ala His  His Thr Glu
    1085                 1090                1095

Thr Leu  Thr Phe Asn Ala Cys  Asp Tyr Asp Ile Asn  Gly Thr Tyr
    1100                 1105                1110

Val Thr  Asp Asn Thr Tyr Leu  Thr Lys Glu Val Val  Phe Tyr Ser
    1115                 1120                1125

His Thr  Glu His Met Trp Val  Glu Val Ser Glu Thr  Glu Gly Val
    1130                 1135                1140

Phe His  Ile Asp Ser Val Glu  Phe Met Glu Thr Gln  Gln
    1145                 1150                1155


<210> SEQ ID NO 41
<211> LENGTH: 3471
<212> TYPE: DNA
<213> ORGANISM: Artificial
<220> FEATURE:
<223> OTHER INFORMATION: Synthetic bacterial coding sequence encoding
      TIC4064_24 comprising mutations at G87K, W370L, H554N, and R585Q.

<400> SEQUENCE: 41

atgaatcaaa ataaacacgg aattattggc gcttccaatt gtggttgtac gtcagataat      60

gttgcgaaat atcctttagc caacaatcca tattcatctg ctttaaattt aaattcttgt     120
```

-continued

```
caaaatagta gtattctcaa ctggattaac ataataggcg atgcagcaaa agaagcagta    180
tctattggga caacaatagt ctctcttatc acagcacctt ctcttactgg attaatttca    240
atagtatatg accttataaa aaaagtacta ggaggtagta gtggacaatc catatcagat    300
ttgtctatat gtgacttatt atctattatt gatttacggg taagtcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc aattggtttt gtacatcgta gtagtcttag gggagaaagt    960
tggtttagct ttgttaatag agctaatttc tcagatttag aaaatgcaat acctaatcct   1020
agaccgtctt ggtttttaaa taatatgatt atatctactg gttcacttac attgccggtt   1080
agcccaagta ctgatagagc gagggtatta tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgaca atggttcgct tggagtattg   1680
agggtccaat ttccacttca cttaagacaa caatatcgca ttagagtccg ttatgcttct   1740
acaacaaata ttcaattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
```

```
aaaaatgcac cagataattt agtatctgat acttacccag atgattcttg tagtggaatc   2520

aatcgatgtc aggaacaaca gatggtaaat gcgcaactgg aaacagaaca tcatcatccg   2580

atggattgct gtggagcagc tcaaacacat gagttttctt cctatattga tacaggggat   2640

ttaaattcga ctgtagacca gggaatctgg gcgatcttta aagttcgaac aacagatggt   2700

tatgcgacgt taggaaatct tgaattggta gagatcggac cgttatcggg tgaatctcta   2760

gaacgtgaac aaagggataa tgcaaaatgg agtgcagagc taggaagaaa gcgtgcagaa   2820

acagatcgcg tgtatcaaga tgccaaacaa tccatcaatc atttatttgt ggattatcaa   2880

gatcaacaat taaatccaga aatagggatg gcagatatta tggacgctca aaatcttgtc   2940

gcatcaattt cagatgtata tagcgatgca gtactgcaaa tccctggaat taactatgag   3000

atttacacag agctatccaa tcgcttacaa caagcatcgt atctgtatac gtctcgaaat   3060

gcggtgcaaa atggggactt taacagcggt ctagatagtt ggaatgcaac agcgggtgct   3120

acggtacaac aggatggtaa tacgcatttc ttagttcttt ctcattggga tgcacaagtt   3180

tctcaacaat ttagagtgca gccaaattgt aaatatgtat tacgtgtaac agcagagaaa   3240

gtaggcggcg gagacggata cgtgacaatc cgggatggtg ctcatcatac agaaacgctt   3300

acatttaatg catgtgatta tgatataaat ggcacgtacg tgactgataa tacgtatcta   3360

acaaaagaag tggtattcta ttcacataca gaacacatgt gggtagaggt aagtgaaaca   3420

gaaggtgttt tccatataga cagtgttgag ttcatggaaa cccaacagta g            3471
```

```
<210> SEQ ID NO 42
<211> LENGTH: 1156
<212> TYPE: PRT
<213> ORGANISM: Artificial
<220> FEATURE:
<223> OTHER INFORMATION: Amino acid sequence of TIC4064_24 comprising
      mutations at G87K, W370L, H554N, and R585Q.

<400> SEQUENCE: 42

Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Lys Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
```

```
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Leu Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp Asn Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Gln Leu Ser Val Asn Gly Ser Phe
            580                 585                 590

Gly Thr Ile Ser Gln Asn Leu Pro Ser Thr Met Arg Leu Gly Glu Asp
        595                 600                 605
```

```
Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020
```

-continued

```
Asn Gly  Asp Phe Asn Ser Gly  Leu Asp Ser Trp Asn  Ala Thr Ala
    1025                1030                1035

Gly Ala  Thr Val Gln Gln Asp  Gly Asn Thr His Phe  Leu Val Leu
    1040                1045                1050

Ser His  Trp Asp Ala Gln Val  Ser Gln Gln Phe Arg  Val Gln Pro
    1055                1060                1065

Asn Cys  Lys Tyr Val Leu Arg  Val Thr Ala Glu Lys  Val Gly Gly
    1070                1075                1080

Gly Asp  Gly Tyr Val Thr Ile  Arg Asp Gly Ala His  His Thr Glu
    1085                1090                1095

Thr Leu  Thr Phe Asn Ala Cys  Asp Tyr Asp Ile Asn  Gly Thr Tyr
    1100                1105                1110

Val Thr  Asp Asn Thr Tyr Leu  Thr Lys Glu Val Val  Phe Tyr Ser
    1115                1120                1125

His Thr  Glu His Met Trp Val  Glu Val Ser Glu Thr  Glu Gly Val
    1130                1135                1140

Phe His  Ile Asp Ser Val Glu  Phe Met Glu Thr Gln  Gln
    1145                1150                1155
```

<210> SEQ ID NO 43
<211> LENGTH: 3471
<212> TYPE: DNA
<213> ORGANISM: Artificial
<220> FEATURE:
<223> OTHER INFORMATION: Synthetic bacterial coding sequence encoding TIC4064_25 comprising mutations at S33G, G87K, I385S, G402Q, and R604N.

<400> SEQUENCE: 43

```
atgaatcaaa ataaacacgg aattattggc gcttccaatt gtggttgtac gtcagataat     60

gttgcgaaat atcctttagc caacaatcca tattcaggag ctttaaattt aaattcttgt    120

caaaatagta gtattctcaa ctggattaac ataataggcg atgcagcaaa agaagcagta    180

tctattggga caacaatagt ctctcttatc acagcacctt ctcttactgg attaatttca    240

atagtatatg accttataaa aaaagtacta ggaggtagta gtggacaatc catatcagat    300

ttgtctatat gtgacttatt atctattatt gatttacggg taagtcagag tgttttaaat    360

gatgggattg cagattttaa tggttctgta ctcttataca ggaactattt agaggctctg    420

gatagctgga ataagaatcc taattctgct tctgctgaag aactccgtac tcgttttaga    480

atcgctgact cagaatttga tagaatttta acacgagggt ctttaacgaa tggtggctcg    540

ttagctagac aaaatgccca aatattatta ttaccttctt ttgcgagtgc tgcatttttc    600

catttattac tactaaggga tgctactaga tatggcacta attgggggct atacaatgct    660

acacctttta taaattatca atcaaaacta gtagagctta ttgaactata tactgattat    720

tgcgtacatt ggtataatcg aggtttcaac gaactaaggc aacgaggcac tagtgctaca    780

gcttggttag aatttcatag atatcgtaga gagatgacat tgatggtatt agatatagta    840

gcatcatttt caagtcttga tattactaat tacccaatag aaacagattt tcagttgagt    900

agggtcattt atacagatcc aattggtttt gtacatcgta gtagtcttag gggagaaagt    960

tggtttagct ttgttaatag agctaatttc tcagatttag aaaatgcaat acctaatcct   1020

agaccgtctt ggtttttaaa taatatgatt atatctactg gttcacttac attgccggtt   1080

agcccaagta ctgatagagc gagggtatgg tatggaagtc gagatcgaat ttcccctgct   1140

aattcacaat tttctactga actaatctct ggacaacata cgactgctac acaaactatt   1200
```

-continued

```
ttacaacgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga atttaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
ttaaattcga ctgtagacca gggaatctgg gcgatcttta aagttcgaac aacagatggt   2700
tatgcgacgt taggaaatct tgaattggta gagatcggac cgttatcggg tgaatctcta   2760
gaacgtgaac aaagggataa tgcaaaatgg agtgcagagc taggaagaaa gcgtgcagaa   2820
acagatcgcg tgtatcaaga tgccaaacaa tccatcaatc atttatttgt ggattatcaa   2880
gatcaacaat taaatccaga aatagggatg gcagatatta tggacgctca aaatcttgtc   2940
gcatcaattt cagatgtata tagcgatgca gtactgcaaa tccctggaat taactatgag   3000
atttacacag agctatccaa tcgcttacaa caagcatcgt atctgtatac gtctcgaaat   3060
gcggtgcaaa atggggactt taacagcggt ctagatagtt ggaatgcaac agcgggtgct   3120
acggtacaac aggatggtaa tacgcatttc ttagttcttt ctcattggga tgcacaagtt   3180
tctcaacaat ttagagtgca gccaaattgt aaatatgtat tacgtgtaac agcagagaaa   3240
gtaggcggcg gagacggata cgtgacaatc cgggatggtg ctcatcatac agaaacgctt   3300
acatttaatg catgtgatta tgatataaat ggcacgtacg tgactgataa tacgtatcta   3360
acaaaagaag tggtattcta ttcacataca gaacacatgt gggtagaggt aagtgaaaca   3420
gaaggtgttt tccatataga cagtgttgag ttcatggaaa cccaacagta g            3471
```

<210> SEQ ID NO 44
<211> LENGTH: 1156

<212> TYPE: PRT
<213> ORGANISM: Artificial
<220> FEATURE:
<223> OTHER INFORMATION: Amino acid sequence of TIC4064_25 comprising mutations at S33G, G87K, I385S, G402Q, and R604N.

<400> SEQUENCE: 44

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Gly Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Lys Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380
```

-continued

```
Ser Thr Glu Leu Ile Ser Gly Gln His Thr Thr Ala Thr Gln Thr Ile
385                 390                 395                 400

Leu Gln Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Asn Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800
```

```
Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                 1015                 1020

Asn Gly  Asp Phe Asn Ser Gly  Leu Asp Ser Trp Asn  Ala Thr Ala
    1025                 1030                 1035

Gly Ala  Thr Val Gln Gln Asp  Gly Asn Thr His Phe  Leu Val Leu
    1040                 1045                 1050

Ser His  Trp Asp Ala Gln Val  Ser Gln Gln Phe Arg  Val Gln Pro
    1055                 1060                 1065

Asn Cys  Lys Tyr Val Leu Arg  Val Thr Ala Glu Lys  Val Gly Gly
    1070                 1075                 1080

Gly Asp  Gly Tyr Val Thr Ile  Arg Asp Gly Ala His  His Thr Glu
    1085                 1090                 1095

Thr Leu  Thr Phe Asn Ala Cys  Asp Tyr Asp Ile Asn  Gly Thr Tyr
    1100                 1105                 1110

Val Thr  Asp Asn Thr Tyr Leu  Thr Lys Glu Val Val  Phe Tyr Ser
    1115                 1120                 1125

His Thr  Glu His Met Trp Val  Glu Val Ser Glu Thr  Glu Gly Val
    1130                 1135                 1140

Phe His  Ile Asp Ser Val Glu  Phe Met Glu Thr Gln  Gln
    1145                 1150                 1155
```

<210> SEQ ID NO 45
<211> LENGTH: 3471
<212> TYPE: DNA
<213> ORGANISM: Artificial
<220> FEATURE:
<223> OTHER INFORMATION: Synthetic bacterial coding sequence encoding TIC4064_26 comprising mutations at G87K, F199Y, V325A, S331A, and Q631T.

<400> SEQUENCE: 45
atgaatcaaa ataaacacgg aattattggc gcttccaatt gtggttgtac gtcagataat 60
gttgcgaaat atcctttagc caacaatcca tattcatctg ctttaaattt aaattcttgt 120
caaaatagta gtattctcaa ctggattaac ataataggcg atgcagcaaa agaagcagta 180
tctattggga caacaatagt ctctcttatc acagcacctt ctcttactgg attaatttca 240
atagtatatg accttataaa aaaagtacta ggaggtagta gtggacaatc catatcagat 300
ttgtctatat gtgacttatt atctattatt gatttacggg taagtcagag tgttttaaat 360
gatgggattg cagattttaa tggttctgta ctcttataca ggaactattt agaggctctg 420
gatagctgga ataagaatcc taattctgct tctgctgaag aactccgtac tcgttttaga 480
atcgctgact cagaatttga tagaatttta acacgagggt ctttaacgaa tggtggctcg 540
ttagctagac aaaatgccca aatattatta ttaccttctt ttgcgagtgc tgcatatttc 600
catttattac tactaaggga tgctactaga tatggcacta attgggggct atacaatgct 660
acacctttta taaattatca atcaaaacta gtagagctta ttgaactata tactgattat 720
tgcgtacatt ggtataatcg aggtttcaac gaactaaggc aacgaggcac tagtgctaca 780
gcttggttag aatttcatag atatcgtaga gagatgacat tgatggtatt agatatagta 840
gcatcatttt caagtcttga tattactaat tacccaatag aaacagattt tcagttgagt 900
agggtcattt atacagatcc aattggtttt gtacatcgta gtagtcttag gggagaaagt 960
tggtttagct ttgcaaatag agctaatttc gcagatttag aaaatgcaat acctaatcct 1020
agaccgtctt ggtttttaaa taatatgatt atatctactg gttcacttac attgccggtt 1080
agcccaagta ctgatagagc gagggtatgg tatggaagtc gagatcgaat ttcccctgct 1140
aattcacaat ttattactga actaatctct ggacaacata cgactgctac acaaactatt 1200
ttagggcgaa atatatttag agtagattct caagcttgta atttaaatga taccacatat 1260
ggagtgaata gggcggtatt ttatcatgat gcgagtgaag gttctcaaag atccgtgtac 1320
gaggggtata ttcgaacaac tgggatagat aaccctagag ttcaaaatat taacacttat 1380
ttacctggag aaaattcaga tatcccaact ccagaagact atactcatat attaagcaca 1440
acaataaatt taacaggagg acttagacaa gtagcatcta atcgccgttc atctttagta 1500
atgtatggtt ggacacataa aagtctggct cgtaacaata ccattaatcc agatagaatt 1560
acacagatac cattgacgaa ggttgatacc cgaggcacag gtgtttctta tgtgaatgat 1620
ccaggattta taggaggagc tctacttcaa aggactgacc atggttcgct tggagtattg 1680
agggtccaat ttccacttca cttaagacaa caatatcgca ttagagtccg ttatgcttct 1740
acaacaaata ttcgattgag tgtgaatggc agtttcggta ctatttctca aaatctccct 1800
agtacaatga gattaggaga ggatttaaga tacggatctt ttgctataag agagtttagt 1860
acttctatta gacccactgc aagtccggac acaattcgat tgacaataga accatctttt 1920
attagacaag aggtctatgt agatagaatt gagttcattc cagttaatcc gacgcgagag 1980
gcgaaagagg atctagaagc aacaaagaaa gcggtggcga gcttgtttac acgcacaagg 2040
gacggattac aagtaaatgt gacagattat caagtcgatc aagcggcaaa tttagtgtca 2100
tgcttatcag atgaacaata tgcgcatgat aaaaagatgt tattggaagc ggtacgcgcg 2160
gcaaaacgcc tcagccgaga acgcaactta cttcaggatc cagattttaa tacaatcaat 2220
agtacagaag aaaatggatg gaaagcaagt aacggcgtta ctattagcga aggcggtcca 2280
ttctataaag gccgtgcact tcagctagca agtgcacgag aaaattaccc aacatacatc 2340

```
tatcaaaaag tagatgcatc ggagttaaag ccgtatacac gttatagact ggatgggttc   2400

gtgaagagta gtcaagattt agaaattgat ctcattcacc atcataaagt ccatcttgtg   2460

aaaaatgcac cagataattt agtatctgat acttacccag atgattcttg tagtggaatc   2520

aatcgatgtc aggaacaaca gatggtaaat gcgcaactgg aaacagaaca tcatcatccg   2580

atggattgct gtggagcagc tcaaacacat gagttttctt cctatattga tacaggggat   2640

ttaaattcga ctgtagacca gggaatctgg gcgatcttta aagttcgaac aacagatggt   2700

tatgcgacgt taggaaatct tgaattggta gagatcggac cgttatcggg tgaatctcta   2760

gaacgtgaac aaagggataa tgcaaaatgg agtgcagagc taggaagaaa gcgtgcagaa   2820

acagatcgcg tgtatcaaga tgccaaacaa tccatcaatc atttatttgt ggattatcaa   2880

gatcaacaat taaatccaga aatagggatg gcagatatta tggacgctca aaatcttgtc   2940

gcatcaattt cagatgtata tagcgatgca gtactgcaaa tccctggaat taactatgag   3000

atttacacag agctatccaa tcgcttacaa caagcatcgt atctgtatac gtctcgaaat   3060

gcggtgcaaa atggggactt taacagcggt ctagatagtt ggaatgcaac agcgggtgct   3120

acggtacaac aggatggtaa tacgcatttc ttagttcttt ctcattggga tgcacaagtt   3180

tctcaacaat ttagagtgca gccaaattgt aaatatgtat tacgtgtaac agcagagaaa   3240

gtaggcggcg gagacggata cgtgacaatc cgggatggtg ctcatcatac agaaacgctt   3300

acatttaatg catgtgatta tgatataaat ggcacgtacg tgactgataa tacgtatcta   3360

acaaaagaag tggtattcta ttcacataca gaacacatgt gggtagaggt aagtgaaaca   3420

gaaggtgttt tccatataga cagtgttgag ttcatggaaa cccaacagta g            3471
```

<210> SEQ ID NO 46
<211> LENGTH: 1156
<212> TYPE: PRT
<213> ORGANISM: Artificial
<220> FEATURE:
<223> OTHER INFORMATION: Amino acid sequence of TIC4064_26 comprising
      mutations at G87K, F199Y, V325A, S331A, and Q631T.

<400> SEQUENCE: 46

```
Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Lys Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160
```

-continued

```
Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Tyr Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Ala Asn Arg Ala Asn Phe Ala Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575
```

```
Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Thr Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
```

```
        995                 1000                1005

Leu Gln  Gln Ala Ser Tyr Leu  Tyr Thr Ser Arg Asn  Ala Val Gln
    1010                 1015                 1020

Asn Gly  Asp Phe Asn Ser Gly  Leu Asp Ser Trp Asn  Ala Thr Ala
    1025                 1030                 1035

Gly Ala  Thr Val Gln Gln Asp  Gly Asn Thr His Phe  Leu Val Leu
    1040                 1045                 1050

Ser His  Trp Asp Ala Gln Val  Ser Gln Gln Phe Arg  Val Gln Pro
    1055                 1060                 1065

Asn Cys  Lys Tyr Val Leu Arg  Val Thr Ala Glu Lys  Val Gly Gly
    1070                 1075                 1080

Gly Asp  Gly Tyr Val Thr Ile  Arg Asp Gly Ala His  His Thr Glu
    1085                 1090                 1095

Thr Leu  Thr Phe Asn Ala Cys  Asp Tyr Asp Ile Asn  Gly Thr Tyr
    1100                 1105                 1110

Val Thr  Asp Asn Thr Tyr Leu  Thr Lys Glu Val Val  Phe Tyr Ser
    1115                 1120                 1125

His Thr  Glu His Met Trp Val  Glu Val Ser Glu Thr  Glu Gly Val
    1130                 1135                 1140

Phe His  Ile Asp Ser Val Glu  Phe Met Glu Thr Gln  Gln
    1145                 1150                 1155
```

<210> SEQ ID NO 47
<211> LENGTH: 3471
<212> TYPE: DNA
<213> ORGANISM: Artificial
<220> FEATURE:
<223> OTHER INFORMATION: Synthetic bacterial coding sequence encoding TIC4064_27 comprising mutations at G87S, I308C, V325A, S331A, and Q631T.

<400> SEQUENCE: 47

```
atgaatcaaa ataaacacgg aattattggc gcttccaatt gtggttgtac gtcagataat     60
gttgcgaaat atcctttagc caacaatcca tattcatctg ctttaaattt aaattcttgt    120
caaaatagta gtattctcaa ctggattaac ataataggcg atgcagcaaa agaagcagta    180
tctattggga caacaatagt ctctcttatc acagcacctt ctcttactgg attaatttca    240
atagtatatg accttatatc taaagtacta ggaggtagta gtggacaatc catatcagat    300
ttgtctatat gtgacttatt atctattatt gatttacggg taagtcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc atgtggtttt gtacatcgta gtagtcttag gggagaaagt    960
tggtttagct ttgcaaatag agctaatttc gcagatttag aaaatgcaat acctaatcct   1020
agaccgtctt ggtttttaaa taatatgatt atatctactg gttcacttac attgccggtt   1080
```

```
agcccaagta ctgatagagc gagggtatgg tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac acaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
ttaaattcga ctgtagacca gggaatctgg gcgatcttta aagttcgaac aacagatggt   2700
tatgcgacgt taggaaatct tgaattggta gagatcggac cgttatcggg tgaatctcta   2760
gaacgtgaac aaagggataa tgcaaaatgg agtgcagagc taggaagaaa gcgtgcagaa   2820
acagatcgcg tgtatcaaga tgccaaacaa tccatcaatc atttatttgt ggattatcaa   2880
gatcaacaat taaatccaga aatagggatg gcagatatta tggacgctca aaatcttgtc   2940
gcatcaattt cagatgtata tagcgatgca gtactgcaaa tccctggaat taactatgag   3000
atttacacag agctatccaa tcgcttacaa caagcatcgt atctgtatac gtctcgaaat   3060
gcggtgcaaa atggggactt taacagcggt ctagatagtt ggaatgcaac agcgggtgct   3120
acggtacaac aggatggtaa tacgcatttc ttagttcttt ctcattggga tgcacaagtt   3180
tctcaacaat ttagagtgca gccaaattgt aaatatgtat tacgtgtaac agcagagaaa   3240
gtaggcggcg gagacggata cgtgacaatc cgggatggtg ctcatcatac agaaacgctt   3300
acatttaatg catgtgatta tgatataaat ggcacgtacg tgactgataa tacgtatcta   3360
acaaaagaag tggtattcta ttcacataca gaacacatgt gggtagaggt aagtgaaaca   3420
```

-continued

```
gaaggtgttt tccatataga cagtgttgag ttcatggaaa cccaacagta g           3471


<210> SEQ ID NO 48
<211> LENGTH: 1156
<212> TYPE: PRT
<213> ORGANISM: Artificial
<220> FEATURE:
<223> OTHER INFORMATION: Amino acid sequence of TIC4064_27 comprising
      mutations at G87S, I308C, V325A, S331A, and Q631T.

<400> SEQUENCE: 48

Met Asn Gln Asn Lys His Gly Ile Ile Gly Ala Ser Asn Cys Gly Cys
1               5                   10                  15

Thr Ser Asp Asn Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Ser Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Cys Gly Phe Val His Arg Ser Ser Leu Arg Gly Glu Ser
305                 310                 315                 320

Trp Phe Ser Phe Ala Asn Arg Ala Asn Phe Ala Asp Leu Glu Asn Ala
                325                 330                 335

Ile Pro Asn Pro Arg Pro Ser Trp Phe Leu Asn Asn Met Ile Ile Ser
            340                 345                 350
```

```
Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Thr Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
```

```
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                1015                1020

Asn Gly  Asp Phe Asn Ser Gly  Leu Asp Ser Trp Asn  Ala Thr Ala
    1025                1030                1035

Gly Ala  Thr Val Gln Gln Asp  Gly Asn Thr His Phe  Leu Val Leu
    1040                1045                1050

Ser His  Trp Asp Ala Gln Val  Ser Gln Gln Phe Arg  Val Gln Pro
    1055                1060                1065

Asn Cys  Lys Tyr Val Leu Arg  Val Thr Ala Glu Lys  Val Gly Gly
    1070                1075                1080

Gly Asp  Gly Tyr Val Thr Ile  Arg Asp Gly Ala His  His Thr Glu
    1085                1090                1095

Thr Leu  Thr Phe Asn Ala Cys  Asp Tyr Asp Ile Asn  Gly Thr Tyr
    1100                1105                1110

Val Thr  Asp Asn Thr Tyr Leu  Thr Lys Glu Val Val  Phe Tyr Ser
    1115                1120                1125

His Thr  Glu His Met Trp Val  Glu Val Ser Glu Thr  Glu Gly Val
    1130                1135                1140

Phe His  Ile Asp Ser Val Glu  Phe Met Glu Thr Gln  Gln
    1145                1150                1155
```

<210> SEQ ID NO 49
<211> LENGTH: 3471
<212> TYPE: DNA
<213> ORGANISM: Artificial
<220> FEATURE:
<223> OTHER INFORMATION: Synthetic bacterial coding sequence encoding
TIC4064_10 comprising a mutation at S94T.

<400> SEQUENCE: 49

```
atgaatcaaa ataaacacgg aattattggc gcttccaatt gtggttgtac gtcagataat     60
gttgcgaaat atcctttagc caacaatcca tattcatctg ctttaaattt aaattcttgt    120
caaaatagta gtattctcaa ctggattaac ataataggcg atgcagcaaa agaagcagta    180
tctattggga caacaatagt ctctcttatc acagcacctt ctcttactgg attaatttca    240
atagtatatg accttatagg taaagtacta ggaggtagta caggacaatc catatcagat    300
ttgtctatat gtgacttatt atctattatt gatttacggg taagtcagag tgttttaaat    360
gatgggattg cagattttaa tggttctgta ctcttataca ggaactattt agaggctctg    420
gatagctgga ataagaatcc taattctgct tctgctgaag aactccgtac tcgttttaga    480
atcgctgact cagaatttga tagaatttta acacgagggt ctttaacgaa tggtggctcg    540
ttagctagac aaaatgccca aatattatta ttaccttctt ttgcgagtgc tgcatttttc    600
catttattac tactaaggga tgctactaga tatggcacta attgggggct atacaatgct    660
acacctttta taaattatca atcaaaacta gtagagctta ttgaactata tactgattat    720
tgcgtacatt ggtataatcg aggtttcaac gaactaaggc aacgaggcac tagtgctaca    780
gcttggttag aatttcatag atatcgtaga gagatgacat tgatggtatt agatatagta    840
gcatcatttt caagtcttga tattactaat tacccaatag aaacagattt tcagttgagt    900
agggtcattt atacagatcc aattggtttt gtacatcgta gtagtcttag gggagaaagt    960
tggtttagct ttgttaatag agctaatttc tcagatttag aaaatgcaat acctaatcct   1020
agaccgtctt ggtttttaaa taatatgatt atatctactg gttcacttac attgccggtt   1080
agcccaagta ctgatagagc gagggtatgg tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
```

agtacagaag aaaatggatg gaaagcaagt aacggcgtta ctattagcga aggcggtcca 2280
ttctataaag gccgtgcact tcagctagca agtgcacgag aaaattaccc aacatacatc 2340
tatcaaaaag tagatgcatc ggagttaaag ccgtatacac gttatagact ggatgggttc 2400
gtgaagagta gtcaagattt agaaattgat ctcattcacc atcataaagt ccatcttgtg 2460
aaaaatgcac cagataattt agtatctgat acttacccag atgattcttg tagtggaatc 2520
aatcgatgtc aggaacaaca gatggtaaat gcgcaactgg aaacagaaca tcatcatccg 2580
atggattgct gtggagcagc tcaaacacat gagttttctt cctatattga tacaggggat 2640
ttaaattcga ctgtagacca gggaatctgg gcgatcttta aagttcgaac aacagatggt 2700
tatgcgacgt taggaaatct tgaattggta gagatcggac cgttatcggg tgaatctcta 2760
gaacgtgaac aaagggataa tgcaaaatgg agtgcagagc taggaagaaa gcgtgcagaa 2820
acagatcgcg tgtatcaaga tgccaaacaa tccatcaatc atttatttgt ggattatcaa 2880
gatcaacaat taaatccaga aatagggatg gcagatatta tggacgctca aaatcttgtc 2940
gcatcaattt cagatgtata tagcgatgca gtactgcaaa tccctggaat taactatgag 3000
atttacacag agctatccaa tcgcttacaa caagcatcgt atctgtatac gtctcgaaat 3060
gcggtgcaaa atggggactt taacagcggt ctagatagtt ggaatgcaac agcgggtgct 3120
acggtacaac aggatggtaa tacgcatttc ttagttcttt ctcattggga tgcacaagtt 3180
tctcaacaat ttagagtgca gccaaattgt aaatatgtat tacgtgtaac agcagagaaa 3240
gtaggcggcg gagacggata cgtgacaatc cgggatggtg ctcatcatac agaaacgctt 3300
acatttaatg catgtgatta tgatataaat ggcacgtacg tgactgataa tacgtatcta 3360
acaaaagaag tggtattcta ttcacataca gaacacatgt gggtagaggt aagtgaaaca 3420
gaaggtgttt tccatataga cagtgttgag ttcatggaaa cccaacagta g 3471

<210> SEQ ID NO 50
<211> LENGTH: 1156
<212> TYPE: PRT
<213> ORGANISM: Artificial
<220> FEATURE:
<223> OTHER INFORMATION: Amino acid sequence of TIC4064_10 comprising a mutation at S94T.

<400> SEQUENCE: 50

Met Asn Gln Asn Lys His Gly Ile Ile Gly Ala Ser Asn Cys Gly Cys
1 5 10 15

Thr Ser Asp Asn Val Ala Lys Tyr Pro Leu Ala Asn Asn Pro Tyr Ser
20 25 30

Ser Ala Leu Asn Leu Asn Ser Cys Gln Asn Ser Ser Ile Leu Asn Trp
35 40 45

Ile Asn Ile Ile Gly Asp Ala Ala Lys Glu Ala Val Ser Ile Gly Thr
50 55 60

Thr Ile Val Ser Leu Ile Thr Ala Pro Ser Leu Thr Gly Leu Ile Ser
65 70 75 80

Ile Val Tyr Asp Leu Ile Gly Lys Val Leu Gly Gly Ser Thr Gly Gln
85 90 95

Ser Ile Ser Asp Leu Ser Ile Cys Asp Leu Leu Ser Ile Ile Asp Leu
100 105 110

Arg Val Ser Gln Ser Val Leu Asn Asp Gly Ile Ala Asp Phe Asn Gly
115 120 125

Ser Val Leu Leu Tyr Arg Asn Tyr Leu Glu Ala Leu Asp Ser Trp Asn

-continued

```
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560
```

```
Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975
```

-continued

```
Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                 1015                1020

Asn Gly  Asp Phe Asn Ser Gly  Leu Asp Ser Trp Asn  Ala Thr Ala
    1025                 1030                1035

Gly Ala  Thr Val Gln Gln Asp  Gly Asn Thr His Phe  Leu Val Leu
    1040                 1045                1050

Ser His  Trp Asp Ala Gln Val  Ser Gln Gln Phe Arg  Val Gln Pro
    1055                 1060                1065

Asn Cys  Lys Tyr Val Leu Arg  Val Thr Ala Glu Lys  Val Gly Gly
    1070                 1075                1080

Gly Asp  Gly Tyr Val Thr Ile  Arg Asp Gly Ala His  His Thr Glu
    1085                 1090                1095

Thr Leu  Thr Phe Asn Ala Cys  Asp Tyr Asp Ile Asn  Gly Thr Tyr
    1100                 1105                1110

Val Thr  Asp Asn Thr Tyr Leu  Thr Lys Glu Val Val  Phe Tyr Ser
    1115                 1120                1125

His Thr  Glu His Met Trp Val  Glu Val Ser Glu Thr  Glu Gly Val
    1130                 1135                1140

Phe His  Ile Asp Ser Val Glu  Phe Met Glu Thr Gln  Gln
    1145                 1150                1155
```

<210> SEQ ID NO 51
<211> LENGTH: 3471
<212> TYPE: DNA
<213> ORGANISM: Artificial
<220> FEATURE:
<223> OTHER INFORMATION: Synthetic bacterial coding sequence encoding TIC4064_11 comprising a mutation at G87K.

<400> SEQUENCE: 51

```
atgaatcaaa ataaacacgg aattattggc gcttccaatt gtggttgtac gtcagataat     60

gttgcgaaat atcctttagc caacaatcca tattcatctg ctttaaattt aaattcttgt    120

caaaatagta gtattctcaa ctggattaac ataataggcg atgcagcaaa agaagcagta    180

tctattggga caacaatagt ctctcttatc acagcacctt ctcttactgg attaatttca    240

atagtatatg accttataaa aaaagtacta ggaggtagta gtggacaatc catatcagat    300

ttgtctatat gtgacttatt atctattatt gatttacggg taagtcagag tgttttaaat    360

gatgggattg cagattttaa tggttctgta ctcttataca ggaactattt agaggctctg    420

gatagctgga ataagaatcc taattctgct tctgctgaag aactccgtac tcgttttaga    480

atcgctgact cagaatttga tagaatttta acacgagggt ctttaacgaa tggtggctcg    540

ttagctagac aaaatgccca aatattatta ttaccttctt ttgcgagtgc tgcatttttc    600

catttattac tactaaggga tgctactaga tatggcacta attgggggct atacaatgct    660

acacctttta taaattatca atcaaaacta gtagagctta ttgaactata tactgattat    720

tgcgtacatt ggtataatcg aggtttcaac gaactaaggc aacgaggcac tagtgctaca    780

gcttggttag aatttcatag atatcgtaga gagatgacat tgatggtatt agatatagta    840

gcatcatttt caagtcttga tattactaat tacccaatag aaacagattt tcagttgagt    900

agggtcattt atacagatcc aattggtttt gtacatcgta gtagtcttag gggagaaagt    960
```

-continued

```
tggtttagct ttgttaatag agctaatttc tcagatttag aaaatgcaat acctaatcct   1020
agaccgtctt ggtttttaaa taatatgatt atatctactg gttcacttac attgccggtt   1080
agcccaagta ctgatagagc gagggtatgg tatggaagtc gagatcgaat ttcccctgct   1140
aattcacaat ttattactga actaatctct ggacaacata cgactgctac acaaactatt   1200
ttagggcgaa atatatttag agtagattct caagcttgta atttaaatga taccacatat   1260
ggagtgaata gggcggtatt ttatcatgat gcgagtgaag gttctcaaag atccgtgtac   1320
gaggggtata ttcgaacaac tgggatagat aaccctagag ttcaaaatat taacacttat   1380
ttacctggag aaaattcaga tatcccaact ccagaagact atactcatat attaagcaca   1440
acaataaatt taacaggagg acttagacaa gtagcatcta atcgccgttc atctttagta   1500
atgtatggtt ggacacataa aagtctggct cgtaacaata ccattaatcc agatagaatt   1560
acacagatac cattgacgaa ggttgatacc cgaggcacag gtgtttctta tgtgaatgat   1620
ccaggattta taggaggagc tctacttcaa aggactgacc atggttcgct tggagtattg   1680
agggtccaat ttccacttca cttaagacaa caatatcgca ttagagtccg ttatgcttct   1740
acaacaaata ttcgattgag tgtgaatggc agtttcggta ctatttctca aaatctccct   1800
agtacaatga gattaggaga ggatttaaga tacggatctt ttgctataag agagtttagt   1860
acttctatta gacccactgc aagtccggac caaattcgat tgacaataga accatctttt   1920
attagacaag aggtctatgt agatagaatt gagttcattc cagttaatcc gacgcgagag   1980
gcgaaagagg atctagaagc aacaaagaaa gcggtggcga gcttgtttac acgcacaagg   2040
gacggattac aagtaaatgt gacagattat caagtcgatc aagcggcaaa tttagtgtca   2100
tgcttatcag atgaacaata tgcgcatgat aaaaagatgt tattggaagc ggtacgcgcg   2160
gcaaaacgcc tcagccgaga acgcaactta cttcaggatc cagattttaa tacaatcaat   2220
agtacagaag aaaatggatg gaaagcaagt aacggcgtta ctattagcga aggcggtcca   2280
ttctataaag gccgtgcact tcagctagca agtgcacgag aaaattaccc aacatacatc   2340
tatcaaaaag tagatgcatc ggagttaaag ccgtatacac gttatagact ggatgggttc   2400
gtgaagagta gtcaagattt agaaattgat ctcattcacc atcataaagt ccatcttgtg   2460
aaaaatgcac cagataattt agtatctgat acttacccag atgattcttg tagtggaatc   2520
aatcgatgtc aggaacaaca gatggtaaat gcgcaactgg aaacagaaca tcatcatccg   2580
atggattgct gtggagcagc tcaaacacat gagttttctt cctatattga tacaggggat   2640
ttaaattcga ctgtagacca gggaatctgg gcgatcttta aagttcgaac aacagatggt   2700
tatgcgacgt taggaaatct tgaattggta gagatcggac cgttatcggg tgaatctcta   2760
gaacgtgaac aaagggataa tgcaaaatgg agtgcagagc taggaagaaa gcgtgcagaa   2820
acagatcgcg tgtatcaaga tgccaaacaa tccatcaatc atttatttgt ggattatcaa   2880
gatcaacaat taaatccaga aatagggatg gcagatatta tggacgctca aaatcttgtc   2940
gcatcaattt cagatgtata tagcgatgca gtactgcaaa tccctggaat taactatgag   3000
atttacacag agctatccaa tcgcttacaa caagcatcgt atctgtatac gtctcgaaat   3060
gcggtgcaaa atggggactt taacagcggt ctagatagtt ggaatgcaac agcgggtgct   3120
acggtacaac aggatggtaa tacgcatttc ttagttcttt ctcattggga tgcacaagtt   3180
tctcaacaat ttagagtgca gccaaattgt aaatatgtat tacgtgtaac agcagagaaa   3240
gtaggcggcg gagacggata cgtgacaatc cgggatggtg ctcatcatac agaaacgctt   3300
acatttaatg catgtgatta tgatataaat ggcacgtacg tgactgataa tacgtatcta   3360
```

acaaaagaag tggtattcta ttcacataca gaacacatgt gggtagaggt aagtgaaaca 3420
gaaggtgttt tccatataga cagtgttgag ttcatggaaa cccaacagta g 3471

<210> SEQ ID NO 52
<211> LENGTH: 1156
<212> TYPE: PRT
<213> ORGANISM: Artificial
<220> FEATURE:
<223> OTHER INFORMATION: Amino acid sequence of TIC4064_11 comprising a mutation at G87K.

<400> SEQUENCE: 52

Met Asn Gln Asn Lys His Gly Ile Ile Gly Ala Ser Asn Cys Gly Cys
1 5 10 15

Thr Ser Asp Asn Val Ala Lys Tyr Pro Leu Ala Asn Asn Pro Tyr Ser
20 25 30

Ser Ala Leu Asn Leu Asn Ser Cys Gln Asn Ser Ser Ile Leu Asn Trp
35 40 45

Ile Asn Ile Ile Gly Asp Ala Ala Lys Glu Ala Val Ser Ile Gly Thr
50 55 60

Thr Ile Val Ser Leu Ile Thr Ala Pro Ser Leu Thr Gly Leu Ile Ser
65 70 75 80

Ile Val Tyr Asp Leu Ile Lys Lys Val Leu Gly Gly Ser Ser Gly Gln
85 90 95

Ser Ile Ser Asp Leu Ser Ile Cys Asp Leu Leu Ser Ile Ile Asp Leu
100 105 110

Arg Val Ser Gln Ser Val Leu Asn Asp Gly Ile Ala Asp Phe Asn Gly
115 120 125

Ser Val Leu Leu Tyr Arg Asn Tyr Leu Glu Ala Leu Asp Ser Trp Asn
130 135 140

Lys Asn Pro Asn Ser Ala Ser Ala Glu Glu Leu Arg Thr Arg Phe Arg
145 150 155 160

Ile Ala Asp Ser Glu Phe Asp Arg Ile Leu Thr Arg Gly Ser Leu Thr
165 170 175

Asn Gly Gly Ser Leu Ala Arg Gln Asn Ala Gln Ile Leu Leu Leu Pro
180 185 190

Ser Phe Ala Ser Ala Ala Phe Phe His Leu Leu Leu Leu Arg Asp Ala
195 200 205

Thr Arg Tyr Gly Thr Asn Trp Gly Leu Tyr Asn Ala Thr Pro Phe Ile
210 215 220

Asn Tyr Gln Ser Lys Leu Val Glu Leu Ile Glu Leu Tyr Thr Asp Tyr
225 230 235 240

Cys Val His Trp Tyr Asn Arg Gly Phe Asn Glu Leu Arg Gln Arg Gly
245 250 255

Thr Ser Ala Thr Ala Trp Leu Glu Phe His Arg Tyr Arg Arg Glu Met
260 265 270

Thr Leu Met Val Leu Asp Ile Val Ala Ser Phe Ser Ser Leu Asp Ile
275 280 285

Thr Asn Tyr Pro Ile Glu Thr Asp Phe Gln Leu Ser Arg Val Ile Tyr
290 295 300

Thr Asp Pro Ile Gly Phe Val His Arg Ser Ser Leu Arg Gly Glu Ser
305 310 315 320

Trp Phe Ser Phe Val Asn Arg Ala Asn Phe Ser Asp Leu Glu Asn Ala
325 330 335

-continued

```
Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
    370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
    450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
        515                 520                 525

Asp Thr Arg Gly Thr Gly Val Ser Tyr Val Asn Asp Pro Gly Phe Ile
    530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
        595                 600                 605

Leu Arg Tyr Gly Ser Phe Ala Ile Arg Glu Phe Ser Thr Ser Ile Arg
    610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Thr Lys Lys Ala Val
            660                 665                 670

Ala Ser Leu Phe Thr Arg Thr Arg Asp Gly Leu Gln Val Asn Val Thr
        675                 680                 685

Asp Tyr Gln Val Asp Gln Ala Ala Asn Leu Val Ser Cys Leu Ser Asp
    690                 695                 700

Glu Gln Tyr Ala His Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Leu Gln
```

-continued

```
        755                 760                 765

Leu Ala Ser Ala Arg Glu Asn Tyr Pro Thr Tyr Ile Tyr Gln Lys Val
    770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Ala Pro Asp Asn Leu Val Ser Asp Thr Tyr
            820                 825                 830

Pro Asp Asp Ser Cys Ser Gly Ile Asn Arg Cys Gln Glu Gln Gln Met
        835                 840                 845

Val Asn Ala Gln Leu Glu Thr Glu His His His Pro Met Asp Cys Cys
    850                 855                 860

Gly Ala Ala Gln Thr His Glu Phe Ser Ser Tyr Ile Asp Thr Gly Asp
865                 870                 875                 880

Leu Asn Ser Thr Val Asp Gln Gly Ile Trp Ala Ile Phe Lys Val Arg
                885                 890                 895

Thr Thr Asp Gly Tyr Ala Thr Leu Gly Asn Leu Glu Leu Val Glu Ile
            900                 905                 910

Gly Pro Leu Ser Gly Glu Ser Leu Glu Arg Glu Gln Arg Asp Asn Ala
        915                 920                 925

Lys Trp Ser Ala Glu Leu Gly Arg Lys Arg Ala Glu Thr Asp Arg Val
    930                 935                 940

Tyr Gln Asp Ala Lys Gln Ser Ile Asn His Leu Phe Val Asp Tyr Gln
945                 950                 955                 960

Asp Gln Gln Leu Asn Pro Glu Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu  Ile Tyr Thr Glu Leu  Ser Asn Arg
        995                 1000                1005

Leu Gln  Gln Ala Ser Tyr Leu  Tyr Thr Ser Arg Asn  Ala Val Gln
    1010                 1015                1020

Asn Gly  Asp Phe Asn Ser Gly  Leu Asp Ser Trp Asn  Ala Thr Ala
    1025                 1030                1035

Gly Ala  Thr Val Gln Gln Asp  Gly Asn Thr His Phe  Leu Val Leu
    1040                 1045                1050

Ser His  Trp Asp Ala Gln Val  Ser Gln Gln Phe Arg  Val Gln Pro
    1055                 1060                1065

Asn Cys  Lys Tyr Val Leu Arg  Val Thr Ala Glu Lys  Val Gly Gly
    1070                 1075                1080

Gly Asp  Gly Tyr Val Thr Ile  Arg Asp Gly Ala His  His Thr Glu
    1085                 1090                1095

Thr Leu  Thr Phe Asn Ala Cys  Asp Tyr Asp Ile Asn  Gly Thr Tyr
    1100                 1105                1110

Val Thr  Asp Asn Thr Tyr Leu  Thr Lys Glu Val Val  Phe Tyr Ser
    1115                 1120                1125

His Thr  Glu His Met Trp Val  Glu Val Ser Glu Thr  Glu Gly Val
    1130                 1135                1140

Phe His  Ile Asp Ser Val Glu  Phe Met Glu Thr Gln  Gln
    1145                 1150                1155
```